US006322962B1

(12) United States Patent
Brown et al.

(10) Patent No.: US 6,322,962 B1
(45) Date of Patent: Nov. 27, 2001

(54) STEROL-REGULATED SITE-1 PROTEASE AND ASSAYS OF MODULATORS THEREOF

(75) Inventors: Michael S. Brown; Dong Cheng; Peter J. Espenshade; Joseph L. Goldstein, all of Dallas; Robert B. Rawson, Lewisville, all of TX (US); Juro Sakai, Tamatsukuri Miyagi (JP)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/360,237

(22) Filed: Jul. 23, 1999

Related U.S. Application Data

(60) Provisional application No. 60/096,571, filed on Aug. 14, 1998.

(51) Int. Cl.[7] .............................. C12Q 1/00; C12Q 1/68; C12N 15/00; C12N 15/09; C12N 15/63

(52) U.S. Cl. ............................... 435/4; 435/6; 435/320.1; 435/325; 435/455; 530/350; 536/23.1; 536/23.4

(58) Field of Search ................................ 536/23.1, 23.4; 435/320.1, 325, 6, 455, 4; 530/350

(56) References Cited

U.S. PATENT DOCUMENTS 5,215,910 6/1993 Brown et al. .................... 435/240.2

FOREIGN PATENT DOCUMENTS

WO 89/01967 3/1989 (WO) .
WO 90/02580 3/1990 (WO) .
WO 90/15637 12/1990 (WO) .
WO 91/09939 7/1991 (WO) .
WO 91/10425 7/1991 (WO) .
WO 91/10470 7/1991 (WO) .
WO 94/26922 11/1994 (WO) .
WO 95/29989 11/1995 (WO) .
WO 97/26321 7/1997 (WO) .
WO 97/26334 7/1997 (WO) .
WO 98/11238 3/1998 (WO) .

OTHER PUBLICATIONS

Sakai et al., "Molecular identification of the sterol–regulated luminal protease that cleaves SREBPs and controls lipid composition of animal cells," Abstract, *Mol. Cell*, 2:505–514, 1998.

Nomura et al., "Prediction of the coding sequences of unidentified human genes. I. The coding sequences of 40 new genes (KIAA0001–KIAA0040) deduced by analysis of randomly sampled cDNA clones from immature myeloid cell lines KG–1," Abstract, *DNA Research*, 1(1):27–35, 1994.

EMBL Database Accession No. Q9Z2A8.

EMBL Database Accession No. AF078105.

Nagase et al., "Prediction the coding sequences of unidentified human genes. III. The coding sequences of 40 new genes (KIAA0081–KIAA0120) deduced by analysis of cDNA clones from human cell line KG–1," *DNA Research*, 2:37–43, 1995.

Nagase et al., "Human mRNA for KIAA0091 gene," In: Prediction the coding sequences of unidentified human genes. III. The coding sequences of 40 new genes (KIAA0081–KIAA0120) deduced by analysis of cDNA clones from human cell line KG–1, EMBL Sequence Database D42053, Nov. 23, 1994.

Nagase et al., "Human mRNA for KIAA0091 gene," In: Prediction the coding sequences of unidentified human genes. III. The coding sequences of 40 new genes (KIAA081–KIAA0120) deduced by analysis of cDNA clones from human cell line KG–1, EMBL Sequence Database Q14703, Nov. 1, 1996.

Anderson et al., "Activation of the furin endoprotease is a multiple step process: requirements for acidification and internal propeptide cleavage," *EMBO*, 16:1508–1518, 1997.

Brown and Goldstein, "The SREBP pathway: Regulation of cholesterol metabolism by proteolysis of a membrane–bound transciption factor," *Cell*, 89:331–340, 1997.

Cao et al., "Complementation of mutation in acyl–CoA: cholesterol acyltransferase (ACAT) fails to restore sterol regulation in ACAT–defective sterol–resistant hamster cells," *J. Biol. Chem.*, 271:14642–14648, 1996.

Chen et al., cDNA cloning and expression of the peptide–binding β subunit of rat p21$^{ras}$ farnesyltransferase, the counterpart of yeast DPR1/RAM1, *Cell*, 66:327–334, 1991.

Duncan et al., "Cleavage site for sterol–regulated protease localized to a Leu–Ser bond in lumenal loop of sterol regulatory element binding protein–2," *J. Biol. Chem.*, 272:12778–12785, 1997.

Duncan et al., "Second–site cleavage in sterol regulatory element–binding protein occurs at transmembrane junction as determined by cysteine panning," *J. Biol. Chem.*, 273:17801–17809, 1998.

Goldstein et al., "Receptor–mediated endocytosis of Low–Density Lipoprotein in cultured cells," *Meth. Enzymol.*, 98:241–260, 1983.

Hasan et al., "Somatic cell genetic and biochemical characterization of cell lines resulting from human genomic DNA transfections of Chinese hamster ovary cell mutants defective in sterol–dependent activation of sterol synthesis and LDL receptor expression," *Somatic Cell Mol. Genet.*, 20:183–194, 1994.

(List continued on next page.)

*Primary Examiner*—Jill D. Martin
*Assistant Examiner*—Peter Paras, Jr.
(74) *Attorney, Agent, or Firm*—Fulbright & Jaworski5

(57) ABSTRACT

The invention provides assays for the identification of modulators of Site-1 protease. Further provided by the invention are expression constructs and the transgenic cells useful for the development of such assays for Site-1 specific protease. The cells allow the implementation of in vitro assays for potential modulators of Site-specific proteases. Still further provided by the invention are in vitro assays employing Site-1 protease which has been isolated from cells.

28 Claims, 31 Drawing Sheets

OTHER PUBLICATIONS

Hebert et al., "Calnexin, calreticulin, and Bip/Kar2p in protein folding," *Cold Spring Harbor Symp. Quant. Biol.*, 60:405–415, 1995.

Hua et al., "Sterol resistance in CHO cells traced to point mutation in SREBP cleavage activating–protein (SCAP)," *Cell*, 87:415–426, 1996.

Hua et al., "Regulated cleavage of sterol regulatory element binding proteins (SREBPs) requires sequences on both sides of the endoplasmic reticulum membrane," *J. Biol. Chem.*, 271:10379–10384, 1996.

Hua et al., "Hairpin orientation of sterol regulatory element–binding protein–2 in cell membranes as determined by protease protection," *J. Biol. Chem.*, 270:29422–29427, 1995.

Loftus et al., "Murine model of Niemann–Pick C disease: Mutation in a cholesterol homeostasis gene," *Science*, 277:232–235, 1997.

Metherall et al., "Loss of transcriptional repression of three sterol–regulated genes in mutant hamster cells,", *J. Biol. Chem.*, 264:15634–15641, 1989.

Molloy et al., "Human furin is a calcium–dependent serine endoprotease that recognizes the sequence Arg–X–X–Arg and efficiently cleaves anthrax toxin protective antigen," *J. Biol. Chem.*, 267:16396–16402, 1992.

Nohturfft et al., "Topology of SREBP cleavage–activating protein, a polytopic membrane protein with a sterol–sensing domain," *J. Biol. Chem.*, 273:17243–17250. 1998.

Nohturfft et al., "Sterols regulate processing of carbohydrate chains of wild–type SREBP cleavage–activating protein (SCAP), but not sterol–resistant mutants Y298C or D443N," *Proc. Natl. Acad. Sci. USA*, 95:12848–12853, 1998.

Nohturfft et al., "Recurrent G–to–A substitution in a single codon of SREBP cleavage–activating protein causes sterol resistance in three mutant CHO cell lines," *Proc. Natl. Acad. Sci. USA*, 93:13709–13714, 1996.

Rawson et al., "Isolation of cholesterol–requiting mutant CHO cells with defects in cleavage of sterol regulatory element binding proteins at Site–1," *J. Biol. Chem.*, 273:28261–28269, 1998.

Rawson et al., "Complementation cloning of S2P, a gene encoding a putative metallaprotease required for intramembrane cleavage of SREBPs," *Molecular Cell*, 1:47–57, 1997.

Sakai et al., "Sterol–regulated release of SREBP–2 from cell membranes requires two sequential cleavages, one within a transmembrane segment," *Cell*, 85:1037–1046, 1996.

Sakai et al., "Idnetification of complexes between the COOH–terminal domains of sterol regulatory element binding proteins (SREBPs) and SREBP Cleavage–Activating Protein (SCAP)," *J. Biol. Chem.*, 272:20213–20221, 1997.

Sakai et al., "Cleavage of sterol regulatory element binding proteins (SREBPs) at site–1 requires interaction with SREBP cleavage–activating protein. Evidence from in vivo competition studies," *J. Biol. Chem.*, 273:5785–5793, 1998.

Sakai et al., "Molecular identification of the sterol–regulated luminal protease that cleaves SREBPs and controls lipid composition of animal cells," *Mol. Cell*, 2:505–514, 1998.

Seidah et al., "Mammalian subtilisin/kexin isozyme SKI–1: a widely expressed proprotein convertase with a unique cleavage specificty and cellular localization," *Proc. Natl. Acad. Sci. USA*, 96:1321–1326, 1999.

Sørensen et al., "Mutational replacements of the amino acid residues forming the hydrophobic S4 binding pocket of subtilisin 309 from *Bacilus lentus,"Biochem.*, 32:8994–8999, 1993.

Tolleshaug et al., "Posttranslational processing of the LDL receptor and its genetic disruption in familial hypercholesterolemia," *Cell*, 30:715–724, 1982.

Wang et al., "SREBP–1, a membrane–bound transcription factor released by sterol–regulated proteolysis," *Cell*, 77:53–62, 1994.

Yang et al., "Three different rearrangements in a single intron truncate sterol regulatory element binding protein–2 and produce sterol–resistant phenotype in three cell lines," *J. Biol. Chem.*, 270:12152–12161, 1995.

```
HAMSTER  MKLINIWLLLLVVLLCGKKHLGDRLGKKAFEKASCPSCSHLTLKV   45
HUMAN    MKLVNIWLLLLVVLLCGKKHLGDRLEKKSFEKAPCPGCSHLTLKV

HAMSTER  EFSSTVVEYEYIVAFNGYFTAKARNSFISSALKSSEVDNWRIIPR   90
HUMAN    EFSSTVVEYEYIVAFNGYFTAKARNSFISSALKSSEVDNWRIIPR

HAMSTER  NNPSSDYPSDFEVIQIKEKQKAGLLTLEDHPNIKRVTPQRKVFRS  135
HUMAN    NNPSSDYPSDFEVIQIKEKQKAGLLTLEDHPNIKRVTPQRKVFRS

HAMSTER  LKFAESDPIVPCNETRWSQKWQSSRPLRRASLSLGSGFWHATGRH  180
HUMAN    LKYAESDPTVPCNETRWSQKWQSSRPLRRASLSLGSGFWHATGRH

HAMSTER  SSRRLLRAIPRQVAQTLQADVLWQMGYTGANVRVAVFDTGLSEKH  225
HUMAN    SSRRLLRAIPRQVAQTLQADVLWQMGYTGANVRVAVFDTGLSEKH

HAMSTER  PHFKNVKERTNWTNERTLDDGLGHGTFVAGVIASMRECQGFAPDA  270
HUMAN    PHFKNVKERTNWTNERTLDDGLGHGTFVAGVIASMRECQGFAPDA

HAMSTER  ELHIFRVFTNNQVSYTSWFLDAFNYAILKKIDVLNLSIGGPDFMD  315
HUMAN    ELHIFRVFTNNQVSYTSWFLDAFNYAILKKIDVLNLSIGGPDFMD

HAMSTER  HPFVDKVWELTANNVIMVSAIGNDGPLYGTLNNPADQMDVIGVGG  360
HUMAN    HPFVDKVWELTANNVIMVSAIGNDGPLYGTLNNPADQMDVIGVGG

HAMSTER  IDFEDNIARFSSRGMTTWELPGGYGRVKPDIVTYGAGVRGSGVKG  405
HUMAN    IDFEDNIARFSSRGMTTWELPGGYGRMKPDIVTYGAGVRGSGVKG

HAMSTER  GCRALSGTSVASPVVAGAVTLLVSTVQKRELVNPASVKQALIASA  450
HUMAN    GCRALSGTSVASPVVAGAVTLLVSTVQKRELVNPASMKQALIASA

HAMSTER  RRLPGVNMFEQGHGKLDLLRAYQILSSYKPQASLSPSYIDLTECP  495
HUMAN    RRLPGVNMFEQGHGKLDLLRAYQILNSYKPQASLSPSYIDLTECP

HAMSTER  YMWPYCSQPIYYGGMPTIVNVTILNGMGVTGRIVDKPEWRPYLPQ  540
HUMAN    YMWPYCSQPIYYGGMPTVVNVTILNGMGVTGRIVDKPDWQPYLPQ
```

*FIG. 4A*

```
HAMSTER  NGDNIEVAFSYSSVLWPWSGYLAISISVTKKAASWEGIAQGHIMI    585
HUMAN    NGDNIEVAFSYSSVLWPWSGYLAISISVTKKAASWEGIAQGHVMI

HAMSTER  TVASPAETEAKNGAEHTSTVKLPIKVKIIPTPPRSKRVLWDQYHN    630
HUMAN    TVASPAETESKNGAEQTSTVKLPIKVKIIPTPPRSKRVLWDQYHN

HAMSTER  LRYPPGYFPRDNLRMKNDPLDWNGDHVHTNFRDMYQHLRSMGYFV    675
HUMAN    LRYPPGYFPRDNLRMKNDPLDWNGDHIHTNFRDMYQHLRSMGYFV

HAMSTER  EVLGAPFTCFDATQYGTLLMVDSEEEYFPEEIAKLRRDVDNGLSL    720
HUMAN    EVLGAPFTCFDASQYGTLLMVDSEEEYFPEEIAKLRRDVDNGLSL

HAMSTER  VIFSDWYNTSVMRKVKFYDENTRQWWMPDTGGANIPALNELLSVW    765
HUMAN    VIFSDWYNTSVMRKVKFYDENTRQWWMPDTGGANIPALNELLSVW

HAMSTER  NMGFSDGLYEGEFALANHDMYYASGCSIAKFPEDGVVITQTFKDQ    810
HUMAN    NMGFSDGLYEGEFTLANHDMYYASGCSIAKFPEDGVVITQTFKDQ

HAMSTER  GLEVLKQETAVVENVPILGLYQIPAEGGGRIVLYGDSNCLDDSHR    855
HUMAN    GLEVLKQETAVVENVPILGLYQIPAEGGGRIVLYGDSNCLDDSHR

HAMSTER  QKDCFWLLDALLQYTSYGVNPPSLSHSGNRQRPPSGAGLAPPERM    900
HUMAN    QKDCFWLLDALLQYTSYGVTPPSLSHSGNRQRPPSGAGSVTPERM

HAMSTER  EGNHLHRYSKVLEAHLGDPKPRPLPACPHLSWAKPQPLNETAPSN    945
HUMAN    EGNHLHRYSKVLEAHLGDPKPRPLPACPRLSWAKPQPLNETAPSN

HAMSTER  LWKHQKLLSIDLDKVVLPNFRSNRPQVRPLSPGESGAWDIPGGIM    990
HUMAN    LWKHQKLLSIDLDKVVLPNFRSNRPQVRPLSPGESGAWDIPGGIM

HAMSTER  PGRYNQEVGQTIPVFAFLGAMVALAFFVVQISKAKSRPKRRRPRA   1035
HUMAN    PGRYNQEVGQTIPVFAFLGAMVVLAFFVVQINKAKSRPKRRKPRV

HAMSTER  KRPQLTQQTHPPRTPSV                               1052
HUMAN    KRPQLMQQVHPPKTPSV
```

FIG. 4B

| | | | | | | | Transfected Cells | | | | | |
|---|---|---|---|---|---|---|---|---|---|---|---|---|
| Cell Line | CHO-7 | | | SRD-12B | | | S1P(1052) | | | S1P(983) | | |
| Sterols | - | - | + | - | - | + | - | - | + | - | - | + |
| Compactin | - | + | + | - | + | + | - | + | + | - | + | + |
| Lane | 1 | 2 | 3 | 4 | 5 | 6 | 7 | 8 | 9 | 10 | 11 | 12 |

| Cell Line | S1P(1052) | | | | S1P(983) | | | | | | | |
|---|---|---|---|---|---|---|---|---|---|---|---|---|
| Fraction | Cell Lysate | | | | Cell Lysate | | | | Medium | | | |
| EndoH | - | - | + | - | - | - | + | - | - | - | + | - |
| PNGaseF | - | + | - | - | - | + | - | - | - | + | - | - |
| Lane | 1 | 2 | 3 | 4 | 5 | 6 | 7 | 8 | 9 | 10 | 11 | 12 |

STEROL-REGULATED SITE-1 PROTEASE AND ASSAYS OF MODULATORS THEREOF

This application claims the benefit of U.S. Provisional Application, Ser. No. 60/096,571, filed Aug. 14, 1998. The government owns rights in the present invention pursuant to grants number HL-20948 from the National Institutes of Health, NIH Research Science Fellowship Award number HL09993, and NIH Medical Scientist Training Grant GM08014.

BACKGROUND OF THE INVENTION

1. Field of the Invention

The present invention relates generally to the fields of medicine. More particularly, it concerns assays for the identification of modulators of cholesterol and fatty acid metabolism.

2. Description of Related Art

Cholesterol and fatty acids are the hydrophobic building blocks of cell membranes. Their synthesis and uptake must be coordinated so as to supply sufficient amounts for new membrane synthesis while avoiding over accumulation. Coordination is achieved by a family of transcription factors designated sterol regulatory element binding proteins (SREBPs) that are bound to membranes of the endoplasmic reticulum (ER) and nuclear envelope (Brown and Goldstein, 1997). When cells are deprived of sterols, a two-step proteolytic process releases the active portions of the SREBPs from cell membranes, allowing them to translocate to the nucleus where they activate transcription of more than a dozen genes encoding enzymes required for biosynthesis and uptake of cholesterol and unsaturated fatty acids. When sterols build up in cells, the proteolytic release process is blocked, the SREBPs remain membrane-bound, and transcription of the target genes declines. A crucial component in this regulatory pathway is the Site-1 protease (S1P), which makes the first cut in the SREBPs, thereby initiating release (Sakai et al., 1996; Duncan et al.,1997). S1P is the target of feedback regulation: its activity is extinguished in sterol-overloaded cells. So far, nothing is known about the structure or properties of S1P.

SREBPs are bound to the ER membrane and nuclear envelope in a hairpin orientation. The $NH_2$-terminal and COOH-terminal domains, each about 500 amino acids in length, project into the cytosol. They are linked by a pair of membrane-spanning sequences that flank a short 31-amino acid hydrophilic loop that projects into the lumen of the ER and nuclear envelope (Brown and Goldstein, 1997). When cells are depleted of sterols, S1P cleaves the SREBPs at a leucine-serine bond in the luminal loop, thereby separating the proteins into halves, each with a single membrane spanning sequence (Duncan et al., 1997). The $NH_2$-terminal half is called the "intermediate" form of SREBP. Next, a second protease, designated Site-2 protease (S2P), cleaves the $NH_2$-terminal intermediate at a leucine-cysteine bond that is located just within the first membrane spanning segment (Duncan et al., 1998). This liberates the $NH_2$-terminal fragment, which dissociates from the membrane with three hydrophobic residues at its COOH-terminus. This fragment, designated nuclear SREBP (nSREBP) enters the nucleus and activates gene transcription.

The Site-1 cleavage reaction requires the participation of a membrane-bound regulatory protein designated SREBP cleavage-activating protein (SCAP) (Hua et al., 1996a). SCAP has two domains: a hydrophobic $NH_2$-terminal membrane domain consisting of eight membrane spanning sequences and a hydrophilic COOH-terminal domain containing five "WD" repeats that projects into the cytosol (Nohturfft et al., 1998). The COOH-terminal domain of SCAP forms a tight complex with the COOH-terminal domain of the SREBPs (Sakai et al., 1997; Sakai et al., 1998a). Disruption of this complex by overexpression of truncated dominant negative versions of SCAP or SREBP blocks Site-1 cleavage of SREBPs, indicating that the SCAP/SREBP complex is absolutely required for cleavage. Moreover, truncated versions of SREBPs, which lack the COOH-terminal domain, fail to form complexes with SCAP and fail to undergo Site-1 cleavage (Sakai et al., 1998a).

Although the SCAP/SREBP complex is created by interactions on the cytosolic side of the membrane, the complex activates S1P. which cuts the SREBPs on the opposite (luminal) side (Sakai et al., 1998a). The protease cuts between the leucine and serine of the sequence RSVLS (SEQ ID NO:10). Recognition requires only the arginine and leucine: the other residues can be replaced with alanines without reducing cleavage (Duncan et al., 1997).

The Site-1 processing reaction is the target for feedback regulation of lipid biosynthesis and uptake in animal cells. When sterols accumulate in cells, the Site-1 cleavage reaction is blocked (Brown and Goldstein, 1997). The Site-2 cleavage reaction is blocked secondarily since it requires prior cleavage by S1P. The sterol effect appears to be mediated by five of the eight membrane spanning sequences of SCAP, which are designated as the sterol sensor (Hua et al., 1996a). Point mutations at two positions within the sterol sensor render SCAP constitutively active and prevent sterol-mediated suppression of Site-1 cleavage (Nohturfft et al., 1996). Sequences that resemble the sterol-sensing domain are found in three other proteins that are postulated to interact with sterols (Loftus et all., 1997; Nohturfft et al., 1998).

The human gene for S2P has recently been cloned by complementation of the growth defect in a mutant line of Chinese hamster ovary (CHO) cells that fails to synthesize cholesterol owing to a deletion of the S2P gene (Rawson et al., 1997). This gene encodes a unique hydrophobic zinc metalloprotease that cleaves the intermediate forms of SREBPs within their transmembrane sequences.

A similar approach to complementation cloning of S1P has been unavailable up to now because of the difficulty which has been associated with isolating a mutant cell line that fails to carry out Site-1 cleavage. This inability has represented a significant obstacle in the pursuit of further knowledge regarding the regulation of cholesterol and fatty acid metabolism. There is, therefore, a great need in the art for obtaining further information regarding S1P and more specifically, for cloning S1P. Once S1P is cloned, there will be a great need to identify efficient assays which may be employed for the identification of inhibitors of S1P, the inhibitors potentially having great therapeutic value for the treatment of hypercholsterolemia or other lipid metabolism associated conditions.

SUMMARY OF THE INVENTION

In one aspect, the invention provides a method of preparing a candidate modulator of cholesterol biosynthesis in a target cell comprising identifying an agent capable of down regulating Site-1 protease activity in said cell and formulating a composition comprising said agent. In particular embodiments, the modulator is identified by a method comprising the steps of: (a) providing a cell comprising a Site-1 protease; (b) contacting said cell with a candidate modulator; and (c) monitoring said cell for an effect that is not present in the absence of said candidate modulator. The cell may be a mammalian cell, and may be a human cell a hamster cell, a cow cell, a goat cell, a sheep cell, a rat cell or a mouse cell. In one embodiment the mammalian cell is a hamster cell and said Site-1 protease comprises the amino acid sequence of SEQ ID NO:1, or is a human cell and said Site-1 protease comprises the amino acid sequence of SEQ ID NO:3. In another embodiment, the Site-1 protease is encoded by a transgene comprising the nucleotide sequence of SEQ ID NO:2.

In the method, the mammalian cell may be a human cell and said Site-1 protease may comprise the amino acid sequence of SEQ ID NO:3. The Site-1 protease may be encoded by a transgene comprising the nucleotide sequence of SEQ ID NO:4. In particular embodiments of the method, the effect is cholesterol or fatty acid biosynthesis or lipid uptake.

In another aspect, the invention provides a method for preparing a modulator of Site-1 protease comprising the steps of (a) preparing a solution comprising a candidate modulator, Site-1 protease, and a polypeptide target sequence capable of being cleaved by said Site-1 protease; (b) monitoring the rate cleavage of said target sequence in the presence of the candidate modulator relative to the rate of cleavage in the absence of the candidate: and (c) preparing a composition comprising said identified modulator. In other embodiments, the solution further comprises SREBP cleavage activating protein. In one embodiment, the Site-1 protease is a mammalian Site-1 protease, and may be further selected from the group consisting of human, hamster, rat and mouse. In another embodiment of the invention, the Site-1 protease is a hamster Site-1 protease comprising the amino acid sequence of SEQ ID NO:1, or is a human Site-1 protease comprising the amino acid sequence of SEQ ID NO:3.

Another aspect of the invention provides a method for preparing a modulator of Site-1 protease activity comprising the steps of: (a) providing a cell comprising a transgene encoding a fusion protein between a reporter polypeptide and a polypeptide comprising a Site-1 protease target sequence, wherein said transgene is operably linked to a promoter functional in said cell, and wherein said cell comprises Site-1 protease activity; (b) contacting the cell with a candidate modulator; (c) monitoring the activity of said Site-1 protease by detecting said reporter polypeptide; and (d) preparing a composition comprising said identified modulator. In one embodiment of the invention, the fusion polypeptide comprising a Site-1 protease target site is an SREBP. In further embodiments, the cell may comprise a transgene encoding an SREBP cleavage activating protein. The reporter polypeptide may comprise a transit peptide, which peptide may direct excretion of said reporter polypeptide following cleavage of said Site-1 protease target sequence by said Site-1 protease activity.

Monitoring may comprise detecting said reporter polypeptide in the media in which said cell is grown. The Site-1 protease activity of the cell may be endogenous or may be provided by expression of a transgene encoding a Site-1 protease. The subject cell may be a prokaryotic or eukaryotic cell. Where the cell is eukaryotic, the cell will preferably be a mammalian cell selected from the group consisting of a human cell, a hamster cell. a sheep cell, a cow cell, a goat cell, a rat cell and a mouse cell. In particular embodiments, the mammalian cell is a hamster cell and said Site-1 protease comprises the amino acid sequence of SEQ ID NO:1, or the mammalian cell is a human cell and said Site-1 protease comprises the amino acid sequence of SEQ ID NO:3. In one embodiment of the invention, the cell is located in a transgenic, non-human mammal. Where the cell is contained in an animal, monitoring can comprise detecting said reporter polypeptide in extracellular fluid obtained from said animal. The reporter polypeptide used in accordance with the invention may comprise any detectable polypeptide, for example, an enzyme such as alkaline phosphatase, a visually detectable polypeptide, and an immunologically detectable polypeptide. In one embodiment of the invention, a candidate modulator of Site-1 protease is an antisense construct, is from a small molecule library, or is an antibody. Where the modulator is an antibody, the antibody may be a single chain antibody.

Other aspects of the invention provide an isolated nucleic acid sequence encoding a hamster Site-1 protease. In one embodiment of the invention, the hamster Site-1 protease comprises the amino acid sequence of SEQ ID NO:1. The isolated nucleic acid sequence may comprising the nucleotide sequence of SEQ ID NO:2 or be a genomic DNA clone corresponding thereto. Alternatively, the nucleic acid sequence could comprise a codon-modified variant of this sequence.

The invention also provides an expression construct comprising a promoter operably linked to a nucleic acid encoding a Site-1 protease. In one embodiment of the invention, the Site-1 protease is a hamster Site-1 protease comprising the amino acid sequence of SEQ ID NO:1. In this instance, the nucleic acid may comprises the nucleotide sequence of SEQ ID NO:2. In another embodiment of the invention, the Site-1 protease is a human Site-1 protease comprising the amino acid sequence of SEQ ID NO:3. In this instance the nucleic acid may comprises the nucleotide sequence of SEQ ID NO:4. The promoter used may be operable in eukaryotes and/or prokaryotcs.

Another embodiment of the invention provides an expression construct comprising a promoter operably linked to a nucleic acid sequence encoding a polypeptide comprising a reporter polypeptide and a polypeptide comprising a Site-1 protease target sequence. The Site-1 protease target sequence need not be separate from said reporter polypeptide, as it could potentially be located within the reporter polypeptide. The reporter polypeptide will preferably comprise a transit peptide directing the expression of said reporter polypeptide following cleavage of said target site by the Site-1 protease. In this respect, the site-1 protease target site will preferably be membrane bound, thereby preventing the excretion of said reporter polypeptide in the absence of Site-1 protease activity. In further embodiments, the Site-1 protease target site is an SREBP. A reporter polypeptide employed with the invention may comprise potentially any detectable molecule. In exemplary embodiments of the invention the reporter polypeptide is an enzyme, for example, alkaline phosphatase or a visually detectable polypeptide.

Other embodiments of the invention provide a transgenic cell comprising a selected DNA encoding a Site-1 protease, wherein said Site-1 protease is operably linked to a heterologous promoter functional in said cell. In one embodiment of the invention, the Site-1 protease is a hamster Site-1 protease comprising the amino acid sequence of SEQ ID NO:1 or the Site-1 protease is a human Site-1 protease comprising the amino acid sequence of SEQ ID NO:3. In further embodiments of the invention, the selected DNA comprises the nucleotide sequence of SEQ ID NO:2, or the nucleotide sequence of SEQ ID NO:4. The cell may be a prokaryotic or eukaryotic cell. Where the cell is a eukaryotic cell, it will preferably be a mammalian cell. The cell may comprise an mammalian cell, for example, a human cell, a goat cell, a dog cell, a cow cell, a hamster cell, a rat cell and a mouse cell.

The invention also describes a transgenic cell comprising a transgene encoding a fusion protein between a reporter polypeptide and a polypeptide comprising a Site-1 protease target sequence, wherein said transgene is operably linked to a promoter operable in said cell. In particular embodiments of the invention, the polypeptide comprising a Site-1 protease target site is an SREBP. In further embodiments of the invention, the reporter polypeptide comprises a transit peptide which can direct the reporter gene product outside the cell where it can be detected. The transgenic cell may further be defined as comprising a transgene encoding an SREBP cleavage activating protein.

Further embodiments of the invention describe a non-human transgenic animal comprising a transgenic cell comprising a selected DNA encoding a Site-1 protease, wherein said Site-1 protease is operably linked to a heterologous promoter functional in said cell. The animal may be further defined as a mammal selected from the group consisting of a rat, mouse or hamster.

A particular aspect of the invention describes a non-human transgenic animal comprising a transgenic cell comprising a transgene encoding a fusion protein between a reporter polypeptide and a polypeptide comprising a Site-1 protease target sequence, wherein said transgene is operably linked to a promoter operable in said cell. The animal may be further defined as a mammal selected from the group consisting of a rat, mouse or hamster.

The invention also provides a method of reducing serum cholesterol in a patient comprising administering to said patient a pharmaceutical composition comprising a Site-1 protease inhibitor. In particular embodiments of the invention, said administering further comprises treating the patient with an IIMG-CoA reductase inhibitor. In one embodiment of the invention, the Site-1 protease inhibitor is further defined as prepared by a method comprising the steps of: (a) providing a cell comprising a Site-1 protease; (b) contacting said cell with a candidate modulator; (c) monitoring said cell for an effect that is not present in the absence of said candidate modulator; and (d) preparing said modulator. In another embodiment of the invention, the Site-1 protease inhibitor is further defined as prepared by a method comprising the steps of: (a) preparing a solution comprising a candidate modulator, Site-1 protease, and a polypeptide target sequence capable of being cleaved by said Site-1 protease; (b) monitoring the rate cleavage of said target sequence in the presence of the candidate modulator relative to the rate of cleavage in the absence of the candidate; and (c) preparing said modulator. In other embodiments, the solution further comprises SREBP cleavage activating protein. In still further embodiments of the invention, the Site-1 protease inhibitor is further defined as prepared by a method comprising the steps of: (a) providing a cell comprising a transgene encoding a fusion protein between a reporter polypeptide and a polypeptide comprising a Site-1 protease target sequence, wherein said transgene is operably linked to a promoter functional in said cell, and wherein said cell comprises Site-1 protease activity; (b) contacting the cell with a candidate modulator; (c) monitoring the activity of said Site-1 protease by detecting said reporter polypeptide; and (d) preparing said modulator.

The present invention is also directed to an isolated Site-1 protease. Soluble Site-1 proteases will generally be preferred in that the soluble protein is easier to handle, easier to purify without the use of detergents, and thus easier to employ in cell-free assay systems. One means of generating or preparing a soluble Site-1 protease will be through the removal of regions from the transmembrane domain, so-called truncated Site-1 proteases, which are generally more lipophilic than other regions of the protein. Thus, removal of a portion or all of the transmembrane domain facilitates the solubilization of the protein, for example, without the use of detergents or other solubilizing agents. In preferred aspects of the invention, the truncated Site-1 protease will be essentially free of the transmembrane domain. However, there is no absolute requirement to remove the entire transmembrane domain in order to prepare a truncated Site-1 protease having some or all of the advantages in accordance with the present invention.

In the context of the hamster Site-1 protease as given in SEQ ID NO:1, or human Site-1 protease as given in SEQ ID NO:3, an exemplary truncation would be reflected by the absence of all or a portion of the region between about amino acid 900 and about amino acid 1020 of SEQ ID NO:1 or SEQ ID NO:3. For example, the soluble Site-1 protease protein may be truncated between about amino acid 925 and about amino acid 1010 of SEQ ID NO:1 or SEQ ID NO:3. Alternatively, the soluble Site-1 protease protein may be truncated between about amino acid 950 and about amino acid 1000 of SEQ ID NO:1 or SEQ ID NO:3. In preferred embodiments, the soluble Site-1 protease protein may be truncated between about amino acid 960 and about amino acid 990 of SEQ ID NO:1 or SEQ ID NO:3. Even more preferred is a soluble Site-1 protease protein truncated between about amino acid 970 and about amino acid 990 of SEQ ID NO:1 or SEQ ID NO:3. Even more preferred is a soluble Site-1 protease protein truncated between about amino acid 980 and about amino acid 990 of SEQ ID NO:1 or SEQ ID NO:3. The soluble Site-1 protease may be truncated at amino acid 983 of SEQ ID NO:1 or SEQ ID NO:3.

An alternative approach to generating a soluble Site-1 protease would be a site-directed deletion of all or part of the transmembrane region rather than a truncation of the protein. A soluble Site-1 protease may be generated by deleting from about amino acid 950 to about amino acid 1050 of SEQ ID NO:1 or SEQ ID NO:3. In preferred embodiments, a soluble Site-1 protease may be generated by deleting from about amino acid 960 to about amino acid 1040 of SEQ ID NO:1 or SEQ ID NO:3. Alternatively, a soluble Site-1 protease may be generated by deleting from about amino acid 970 to about amino acid 1030 of SEQ ID NO:1 or SEQ ID NO:3. In more preferred embodiments, a soluble Site-1 protease may be Generated by deleting from about amino acid 980 to about amino acid 1030 of SEQ ID NO:1 or SEQ ID NO:3. Even more preferred would be a soluble Site-1 protease generated by deleting from about amino acid 990 to about amino acid 1030 of SEQ ID NO:1 or SEQ ID NO:3. Still even more preferred would be a soluble Site-1 protease generated by deleting from about amino acid 995 to about amino acid 1025 of SEQ ID NO:1 or SEQ ID NO:3.

Other aspects of the invention are directed to a DNA segment which encodes a soluble Site-1 protease. The DNA segment is further defined as encoding a truncated Site-1 protease essentially free of the transmembrane domain. The DNA segment encoding a soluble Site-1 protease may be a truncation of the DNA encoding hamster Site-1 protease as given in SEQ ID NO:2 or a truncation of the DNA encoding human Site-1 protease as given in SEQ ID NO:4. Also described is a cell which expresses the DNA segment encoding a truncated Site-1 protease.

The present invention is further directed to methods of purifying a Site-1 protease, comprising the steps of: (a) obtaining a cell which expresses a Site-1 protease; (b) culturing said cell under conditions to express said Site-1 protease; and (c) purifying the expressed Site-1 protease. In certain aspects of the invention, the Site-1 protease is a soluble Site-1 protease, and the Site-1 protease is purified from culture media in which the cells are growing. In preferred embodiments of the invention, the Site-1 protease is purified by methods including chromatography. The purified Site-1 protease may be expressed by recombinant means or the Site-1 protease may be naturally occuring Site-1 protease.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3(A–D). Alkaline Phosphatase Activity in Medium from SRD-12B Cells Transfected with Pooled cDNAs from a CHO Cell Expression Library. Pools, subpools, and single clones of cDNA plasmids were transfected into SRD-12B cells together with pCMV-PLAP-BP2(513–1141), pCMV-SCAP, and pCMVβ-gal as described in Experimental Procedures. All transfections were performed in duplicate wells (closed and open bars) of 12-well plates.

FIG. 4. Amino Acid Sequence of Hamster and Human S1P (SEQ ID NO:1 and SEQ ID NO:3, respectively). Amino acid residue numbers are shown on the right. Identical residues are highlighted in black. The putative signal sequence is denoted by the dotted overline. The putative membrane-spanning sequence is denoted by the solid overbar. Potential N-linked glycosylation sites are denoted by three dots (●●●). The sequence corresponding to the catalytic triad for subtilisin-like serine proteases (Siezen and Leunissen, 1997) is denoted by asterisks (*). The vertical arrow denotes the site of insertion of 3 tandem copies of the c-Myc epitope in the expression vector pCMV-Myc-S1P. GenBank accession numbers for hamster and human S1P are AF078105 and D42053, respectively.

FIGS. 5(A–C). Hydropathy Plot and Cellular Localization of Hamster S1P.

FIGS. 6(A–B). Expression of S1P mRNA in Wild-type and Mutant Cultured Hamster Cells (FIG. 6A) and in Multiple Human Tissues (FIG. 6B).

FIGS. 9(A–B). Site-1 Cleavage of SREBP-2 in SRD-12B Cells Transfected with Wild-type or Mutant S1P cDNAs.

FIGS. 11(A–D). Domain map and membrane topology of S1P as determined by protease protection.

FIGS. 12(A–B). Processing of Myc-S1P in transfected SRD-12B and HEK-293 cells.

FIGS. 14(A–B). $NH_2$-terminal sequences of proteins precipitated by anti-Myc in cells expressing Myc-tagged S1P.

FIGS. 15(A–B). Processing of Myc-S1P with mutations at cleavage Sites-B and -C.

FIGS. 16(A–D). Cleavage of epitope-tagged SREBP-2 in SRD-12B cells transfected with increasing amounts of plasmid encoding wild-type or mutant Myc-S1P.

FIGS. 18(A–B). S1P processes catalytically inactive S1P (S414A) in trans at Site-C, but not at Site-B, in transfected SRD-12B cells.

FIGS. 19(A–B). Effect of sterols on the processing of S1P in transfected SRD-12B cells. Each dish of SRD-12B cells was transfected with 0.5 μg of either pcDNA3 (lane 1) or pCMV-Myc-S1P (lanes 2 and 3) plus 3 μg of either pTK mock vector (lane 1) or pTK-HSV-BP2 (lanes 2 and 3). After transfection, cells were refed with 5 ml of medium C (medium B containing 5% newborn calf lipoprotein-deficient serum, 50 μM sodium compactin and 50 μM sodium mevalonate) in the absence (lanes 1 and 2) or presence (lane 3) of sterols (1 μg/ml 25-hydroxycholesterol plus 10 μg/ml cholesterol added in a final concentration of 0.2% (v/v) ethanol). After 18 h, cells were harvested, and $10^5$ g membrane fractions and nuclear extracts were prepared.

FIGS. 20(A–C). Sterol-regulated cleavage of SREBP-2 in SRD-12B cells expressing full-length or truncated S1P. FIG. 20B. Aliquots of the $10^5$ g membrane fraction (10 μg protein) were subjected to SDS-PAGE and immunoblotted with 0.5 μg/ml of anti-Myc monoclonal antibody 9E10. The filters were exposed to Kodak X-Omat Blue XB-1 film for 1 s at room temperature. FIG. 20C. Aliquots of nuclear extracts (150 μg protein) and the $10^5$ g membrane fraction (200 μg protein) were subjected to SDS-PAGE and immunoblotted with 5 μg/ml anti-SREBP-2 monoclonal antibody IgG-7D4. the filters for nuclear extracts and membranes were exposed to film for 2 min and 20 s, respectively. P and N denote the uncleaved precursor and cleaved nuclear mature forms of SREBP-2, respectively. Molecular mass standards are expressed in kDa.

Figure 1:
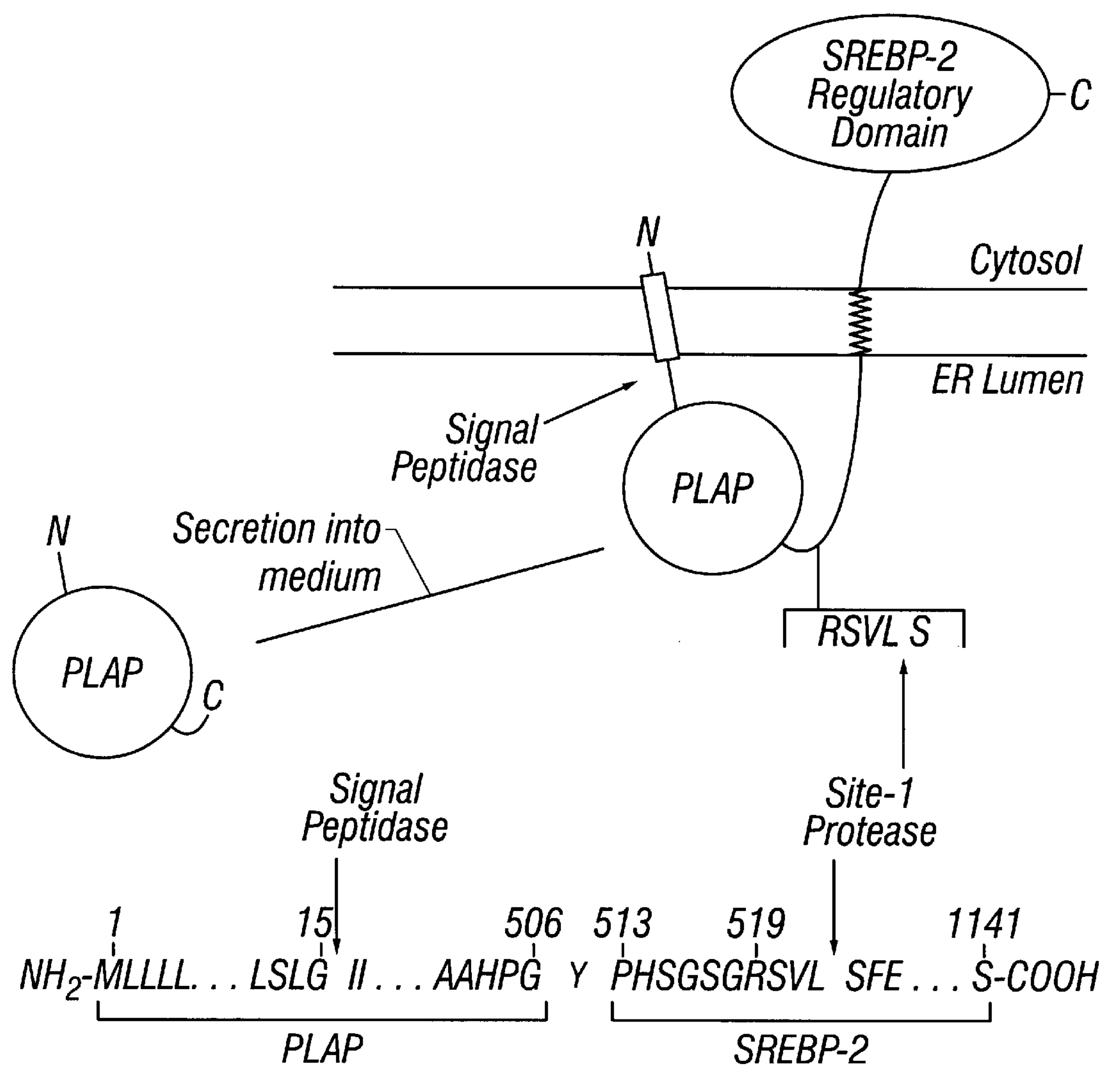
FIG. 1. Proteolytic processing and secretion of the PLAP-BP2(513–1141) Fusion Protein. The plasmid was generated by fusing the sequence encoding the signal peptide and soluble catalytic domain of human placental alkaline phosphatase (amino acids 1–506, SEQ ID NO:59) with the sequence encoding amino acids 513–1141 of human SREBP-2 (SEQ ID NO:60). The one novel amino acid (Y) between the two proteins was generated by blunt ligation during the construction of the plasmid. Secretion of the catalytic domain of PLAP requires cleavage by signal peptidase and Site-1 protease.

21C. Coomassie blue stain of purified S1P(983)-C. On day 0, 10 roller bottles of S1P(983) cells were set up. On day 2, the medium was switched to serum-free CHO-S-SFM II medium. The pooled medium collected from day 3 to day 7 was loaded onto Ni-NTA agarose columns, and chromatography was performed. The eluted protein was concentrated to 2 ml, and 10 μl-aliquots were subjected to SDS-PAGE and Coomassie blue staining. The band in a parallel gel corresponding to the Coomassie blue-stained protein was transferred to a poly(vinylidene fluoride) membrane, cut from the membrane, and subjected to $NH_2$-terminal sequencing by Edman degradation. Molecular mass standards are expressed in kDa.

FIGS. 22(A–C). Cleavage of MCA-conjugated peptides by S1P(983)-C in vitro. FIG. 22A. Time course. Fluorogenic peptide Ac-VFRSLK-MCA (SEQ ID NO:13, 100 μM) was incubated with 1.5 pg purified S1P(983)-C for the indicated time at 37° C. FIG. 22B. Substrate saturation curve. Varying concentrations of the indicated peptide-MCA (corresponding to SEQ ID NO:13, SEQ ID NO:39, and SEQ ID NO:41) were incubated with 3 μg of purified S1P(983)-C at 37° C. for 4 h. A blank consisting of fluorescence measured in parallel reactions lacking S1P was subtracted from each value. FIG. 22C, Inset, shows the Lineweaver-Burk analysis for the cleavage of Ac-VFRSLK-MCA, SEQ ID NO:13, r=0.99). FIG. 22C. pH curve. The indicated peptide-MCA was incubated with 1.5 μg purified S1P (983)-C at the indicated pH. The pH of the assay buffer (containing the ternary buffer system 25 mM Tris, 25 mM Mes, and 25 mM acetic acid) was varied by adjustments with concentrated HCl or NaOH. Each value in FIG. 22A, FIG. 22B, and FIG. 22C represents the average of duplicate incubations, which consistently varied from each other by <10%.

Figure 23A:
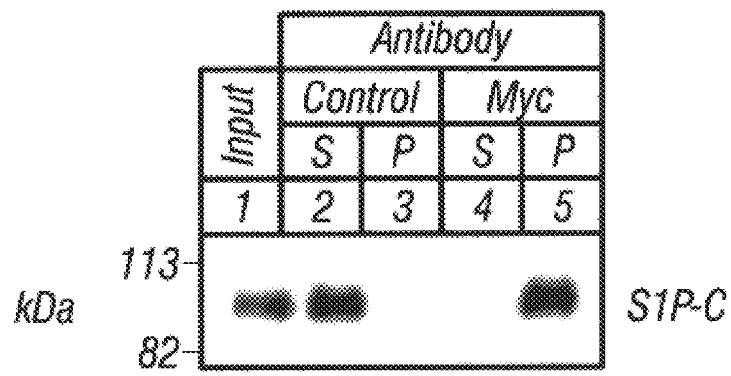
Figure 23B:
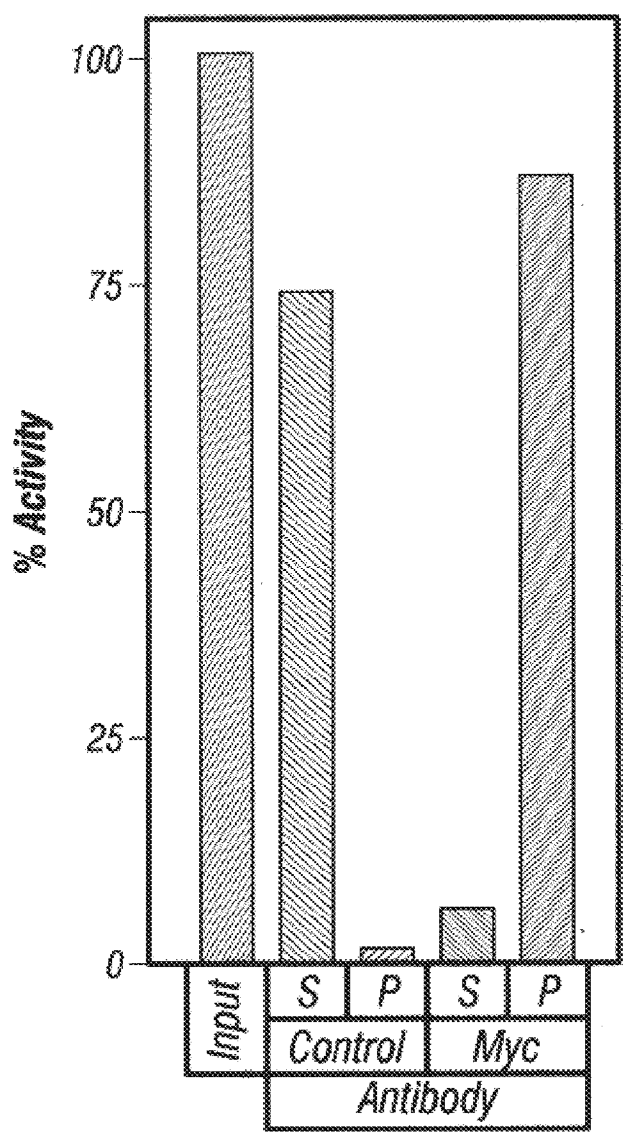
Figure 24A:
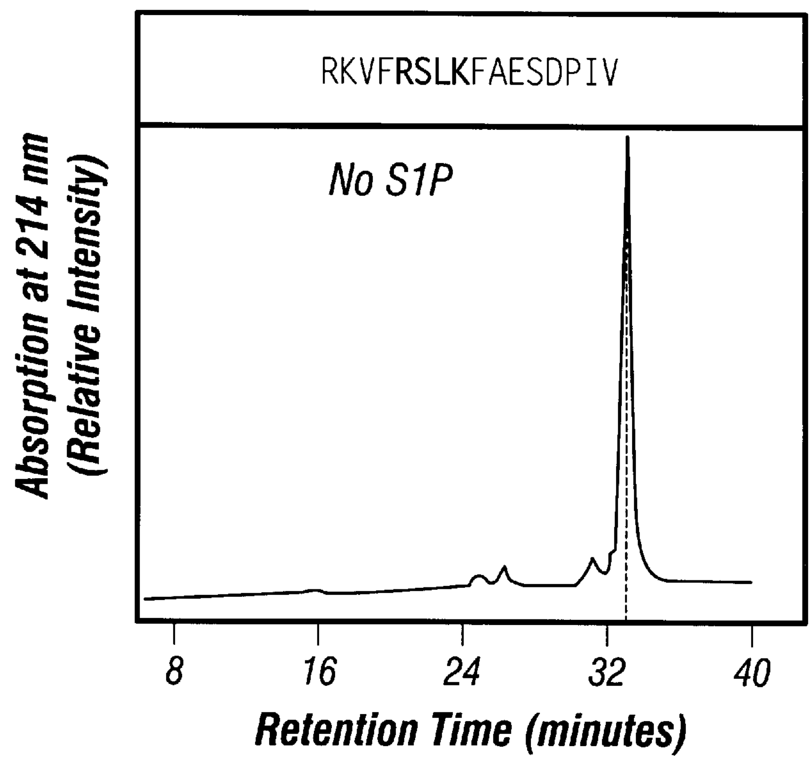
Figure 24B:
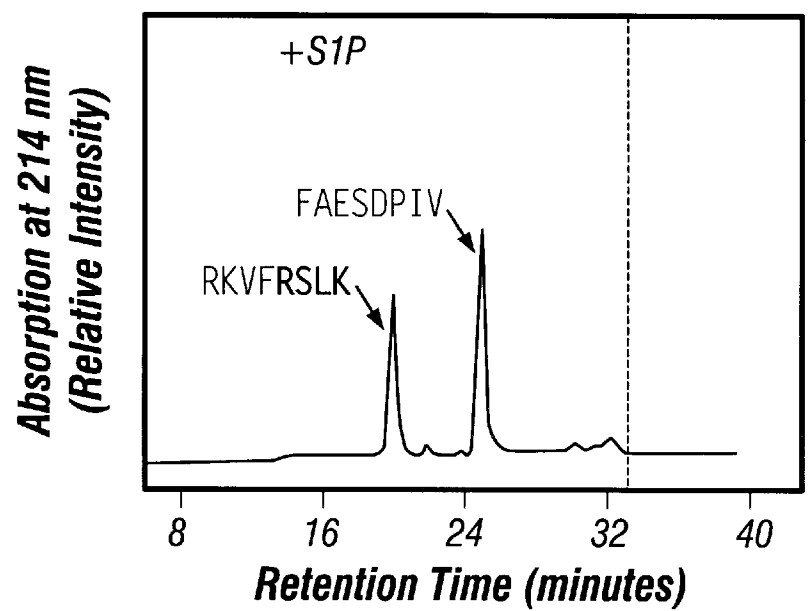
Figure 24C:
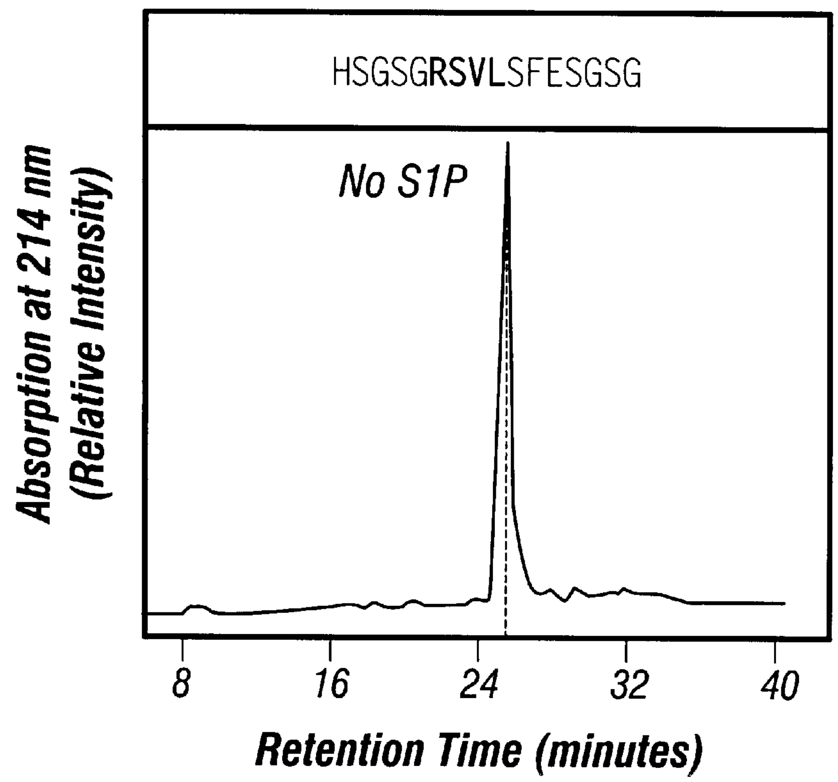
Figure 24D:
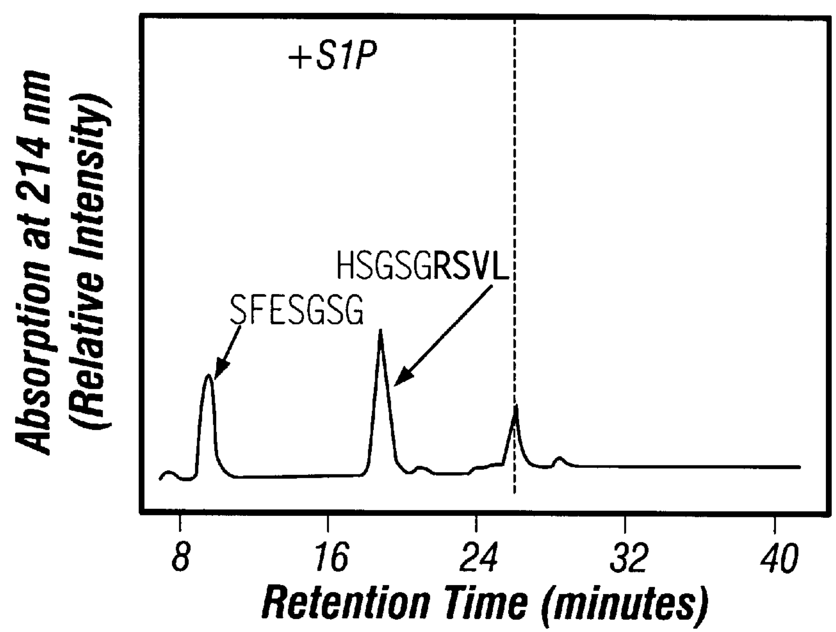

FIG. 23A and FIG. 23B. Immunoprecipitation of S1P (983)-C cleavage activity. FIG. 23A. Immunoblot analysis of S1P(983)-C after immunoprecipitation. Aliquots (200 μg protein) of monoclonal 9E10 anti-Myc antibody or an irrelevant IgG-2001 (Tolleshaug et al., 1982) were each incubated with 100 μl of Protein A/G plus-agarose beads (Santa Cruz Biotechnology, Inc.) for 2 h at 4° C. The beads were pelleted by centrifugation at 3000 g for 10 min at 4° C. and then washed four times with 1 ml of assay buffer (25 mM Tris, 25 mM Mes, 25 mM acetic acid, 1 mM $CaCl_2$ at pH 8). The washed beads were incubated with 15 μg of Ni-NTA agarose column-purified Myc-tagged S1P(983)-C in 1 ml of assay buffer for 2 h at 4° C., after which the beads were pelleted at 3000 g for 10 min, washed four times with 1 ml of assay buffer, and resuspended in 1 ml of assay buffer. Aliquots (10 μl) of the supernatant (S), pellet (P), and input material were subjected to SDS-PAGE and immunoblot analysis with 0.5 μg/ml of the anti-Myc antibody. The filter was exposed to film for 1 s. FIG. 23B. Fluorogenic peptide assay of S1P activity after immunoprecipitation. Aliquots (0.2 ml) of the supernatant, the resuspended agarose beads, and input material were incubated with 100 μM Ac-VFRSLK-MCA (SEQ ID NO:13) for 5 h at 37° C. under standard assay conditions. The data are expressed as the amount of AMC liberated by the input material, which was set at 100%. Each value is the average of duplicate assays.

FIGS. 24(A–D). HPLC assay for activity of S1P(983)-C. Aliquots (20 μg) of synthetic peptides composed of 16 amino acids surrounding Site-B of S1P (FIG. 24A and FIG. 24B) or Site-1 of SREBP-2 (FIG. 24C and FIG. 24D) were incubated in the absence (FIG. 24A and FIG. 24C) or presence (FIG. 24B and FIG. 24D) of 3 μg of purified S1P(983)-C for 4 h at 37°. The reaction mixtures then were subjected to reverse-phase HPLC. The peptides contained within the indicated peaks were identified by MALDI mass spectrometry. These sequences correspond to RKVFRSLK, SEQ ID NO:14; FAESDPIV, SEQ ID NO:15; SFESGSG, SEQ ID NO:16; and, HSGSGRSVL, SEQ ID NO:17.

DESCRIPTION OF ILLUSTRATIVE EMBODIMENTS

Site-1 protease (S1P) cleaves SREBPs in the ER lumen, initiating release from membranes and activating lipid synthesis. To clone S1P, the inventors prepared an assay of Site-1 protease activity based on the expression construct pCMV-PLAP-BP2, which places placental alkaline phosphatase (PLAP) in the ER lumen flanked by the cleavage sites for signal peptidase and S1P. In sterol-deprived cells, PLAP-BP2 is cleaved by both proteases, leading to PLAP secretion. PLAP is not secreted in SRD-12B cells, which are cholesterol auxotrophs that lack S1P. The inventors transfected SRD-12B cells with pCMV-PLAP-BP2 plus pools of CHO cDNAs and identified a cDNA that restores PLAP secretion. The cDNA encodes S1P, an intraluminal 1052-amino acid membrane-bound subtilisin-like serine protease. In SRD-12B cells, the S1P gene is rearranged and not expressed. Transfection with S1P cDNA restores cleavage of SREBPs and abolishes cholesterol auxotrophy.

To further characterize S1P, the inventors transfected cDNAs encoding epitope-tagged hamster S1P into HEK-293 cells or mutant hamster cells that lack S1P. Protease protection assays showed that the bulk of S1P is in the ER lumen, anchored by a COOH-terminal membrane-spanning segment. Cleavage of the $NH_2$-terminal signal sequence of S1P generates S1P-A (amino acids 23–1052 of SEQ ID NO:1), which is inactive. The protein is self-activated by an intramolecular cleavage at Site-B, generating S1P-B (amino acids 138–1052 of SEQ ID NO:1) and liberating a 115-amino acid propeptide that is secreted intact into the medium. The sequence at Site-B is RSLK (SEQ ID NO:18), which differs from the RSVL sequence (SEQ ID NO:11) at the cleavage site in SREBP-2. S1P-B is further cleaved at an internal RRLL sequence (SEQ ID NO:19) to yield S1P-C (amino acids 187–1052 of SEQ ID NO:1). Mutational analysis suggests that S1P-B and S1P-C are both active in cleaving SREBP-2 in a fashion that requires SREBP cleavage-activating protein (SCAP). The activity of S1P-C may be short-lived since it appears to be transported to the Golgi. a site where SREBP-2 cleavage may not normally occur. These data provide the initial description of the processing of a subtilisin-related protease that controls the level of cholesterol in blood and cells.

The inventors designed and purified a soluble, truncated form of S1P which was then used in the development of an in vitro assay for modulators of S1P. The inventors describe a permanent line of Chinese hamster ovary (CHO) cells transfected with a cDNA encoding a truncated form of Site-1 protease (S1P) that is secreted into the culture medium in an enzymatically active form. S1P, a subtilisin-like protease, normally cleaves the luminal loop of sterol regulatory element-binding proteins (SREBPs). This cleavage initiates the two-step proteolytic process by which the $NH_2$-terminal domains of SREBPs are released from cell membranes for translocation to the nucleus where they activate transcription of genes involved in the biosynthesis and uptake of cholesterol and fatty acids. Truncated S1P (amino acids 1–983), produced by the transfected CHO cells, lacks the COOH-terminal membrane anchor. Like native S1P, this truncated protein undergoes normal autocatalytic processing after residue 137 to release an $NH_2$-terminal propeptide, thereby generating an active form, designated S1P-B. Prior to secretion, truncated S1P-B, like native S1P-B, is cleaved further after residue 186 to generate S1P-C, which is the only form that appears in the culture medium. The secreted enzyme, designated S1P(983)-C, cleaves a synthetic peptide that terminates in a 7-amino-4-methyl-coumarin fluorochrome. This peptide, RSLK-MCA (SEQ ID NO:18), corresponds to the internal propeptide cleavage site that generates S1P-B. The secreted enzyme does not cleave RSVL-MCA, a peptide corresponding to the physiologic cleavage site in SREBP-2. However, S1P(983)-C does cleave after this leucine when the RSVL sequence is contained within a 16-residue peptide corresponding to the central portion of the SREBP-2 luminal loop. The catalytic activity of S1P (983)-C differs from that of furin/prohormone convertases, two related proteases, in its more alkaline pH optimum (pH 7–8), its relative resistance to calcium chelating agents, and its ability to cleave after lysine or leucine rather than arginine. These data provide direct biochemical evidence that S1P is the protease that cleaves SREBPs and thereby functions to control lipid biosynthesis and uptake in animal cells. The assay designed by the inventors represents a powerful new technique for the identification of inhibitors of Site-1 protease. These inhibitors have great potential application as therapeutic agents for treatment of conditions associated with elevated serum cholesterol.

I. Cholesterol Metabolism

Animal cells regulate their cholesterol content through the integration of two pathways that govern the supply of exogenous and endogenous cholesterol. Both pathways are controlled by end-product repression. Cells may obtain cholesterol through the receptor-mediated endocytosis and lysosomal hydrolysis of plasma low density lipoprotein. Cells may also increase their endogenous cholesterol production by increasing the amount of two enzymes involved in tie novo cholesterol biosynthesis, namely, 3-hydroxy-3-methylglutaryl coenzyme A (HMG CoA) synthase and HMG CoA reductase.

The LDL receptor gene is the structural gene which provides for the production of the LDL receptor protein, the receptor protein responsible for the facilitated uptake of cholesterol by mammalian cells. Upstream of the coding sequences for the LDL receptor gene is the SRE-1 sequence, which provides for sterol-mediated regulation of LDL receptor gene transcription. In the relative absence of sterols within the cell, transcription of the LDL receptor gene is promoted, whereas in the presence of cholesterol, transcription is suppressed. The transcription of HMG-CoA synthase and reductase of the cholesterol biosynthetic pathway is also reduced when sterols accumulate within the cell. When sterols are depleted, transcription increases and both the uptake and synthesis of cholesterol is promoted.

Currently, there are few cholesterol-lowering drugs that are both safe and efficacious, particularly at the genetic control level, as described above. For example, aside from agents that function by sequestering bile salts in the gut and thereby increase cholesterol excretion, the principal therapeutic agent available for cholesterol lowering is Lovastatin, a drug manufactured by Merck, Co. that acts indirectly to stimulate production of LDL receptors.

Lovastatin, and other drugs in this class (Simvastatin, Pravastatin), act by inhibiting the activity of HMG CoA reductase, the rate-limiting enzyme of endogenous cholesterol synthesis. These drugs contain side chains that resemble the native substrate for HMG CoA reductase and thus competitively inhibit the activity of the enzyme. Eventually this lowers the endogenous synthesis of cholesterol and, by normal homeostatic mechanisms, plasma cholesterol is taken up by increased LDL receptor populations in order to restore the intracellular cholesterol balance.

Conceptually, HMG CoA reductase inhibitors are acting at the penultimate stage of cellular mechanisms for cholesterol metabolism. It would be most desirable if the synthesis of LDL receptor could be directly up regulated at the gene level. The up regulation of LDL receptor synthesis at the gene level offers the promise of resetting the level of blood cholesterol at a lower and clinically more desirable level (Brown et al., 1984).

The activation of cholesterol biosynthesis is achieved by a family of transcription factors designated sterol regulatory element binding proteins (SREBPs) that are bound to membranes of the endoplasmic reticulum (ER) and nuclear envelope (Brown and Goldstein, 1997). When cells are deprived of sterols, a two-step proteolytic process releases the active portions of the SREBPs from cell membranes, allowing them to translocate to the nucleus where they activate transcription of more than a dozen genes encoding enzymes required for biosynthesis and uptake of cholesterol and unsaturated fatty acids. When sterols build up in cells, the proteolytic release process is blocked, the SREBPs remain membrane-bound, and transcription of the target genes declines. A crucial component in this regulatory pathway is the Site-1 protease (S1P), which makes the first cut in the SREBPs, thereby initiating release (Sakai et al., 1996; Duncan et al.,1997). S1P is the target of feedback regulation: its activity is extinguished in sterol-overloaded cells. So far, nothing is known about the structure or properties of S1P.

II. S1P Assays and Identification of Modulators of S1P

The present invention provides for the first time an assay capable of being used for the screening of compounds which inhibit Site-1 protease. In particular, constructs are provided which will cause the excretion of a detectable reporter molecule when S1P is active. The screening assay typically is conducted by growing recombinant host cells in the presence and absence of candidate substances and determining the amount or the activity of the reporter gene. Lower activity in a given sample relative to other samples is suggestive of inhibition. To assay for candidate substances capable of exerting their effects on S1P, one would expose cells to a diverse class of potential S1P activity modulators. One would ideally measure the reporter signal level after an incubation period that is sufficient to demonstrate inhibition of S1P activity. Cells containing varying proportions of candidate substances would then be evaluated for S1P activity relative to control samples and other samples.

Candidates that demonstrate dose related inhibition of the reporter product excretion in media are then selected for further evaluation as clinical therapeutic agents. Alternatively, reporter gene expression may be increased, in which case the candidate compound might be a positive stimulator S1P. Candidate compounds which inhibit S1P expression represent potential useful therapeutic agents that would reduce cholesterol biosynthesis and lipid uptake.

The current invention provides, for the first time, assay which may be used for the targeted identification of modulators of Site-1 protease. Of particular importance is the identification of modulators which specifically down-regulate Site-1 protease. These down regulators may find wide therapeutic use in the treatment of individuals for ailments associated with cholesterol biosynthesis and lipid uptake, for example, in the treatment of hypercholesterolemia.

The current invention provides methods for exposing target cells to a candidate modulator and measuring any subsequent effects, particularly those relating to cholesterol biosynthesis or lipid uptake. In one embodiment of the invention, the target cell is a transgenic cell.

The marker is generally excreted into the media of the test cells, from where it can be quantified using any of a number of techniques. The marker product may be detected directly from the media using for example, ELISA, RIA, enzymatic reaction, and visual detection and the like. Alternatively, the marker may be purified prior to detection according to known methods, such as precipitation (e.g., ammonium sulfate), HPLC, immunoprecipitation, ion exchange chromatography, affinity chromatography (including immunoaffinity chromatography) or various size separations (sedimentation, gel electrophoresis, gel filtration). Such techniques of separation are well known to those of skill in the art. The purified marker may then quantified through immunodetection methods, biological activity, or radioisotope labeling. These techniques are described herein below.

As used herein the term "candidate substance" refers to any molecule that is capable of modulating S1P function. The candidate substance may be a protein or fragment thereof, a small molecule inhibitor, or even a nucleic acid molecule. The active compounds may include fragments or parts of naturally-occurring compounds or may be only found as active combinations of known compounds which are otherwise inactive. However, prior to testing of such compounds in humans or animal models, it will be necessary to test a variety of candidates to determine which have potential.

Accordingly, the active compounds may include fragments or parts of naturally-occurring compounds or may be found as active combinations of known compounds which are otherwise inactive. Accordingly, the present invention provides screening assays to identify agents which stimulate, and particularly, which inhibit S1P activity. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds.

The candidate screening assays provided herein are efficient and can be employed in any desired scale. In assaying for a candidate substance, after obtaining an appropriate cell for screening, one will admix a candidate substance with the cell, under conditions which would allow measurable detection of a marker. In this fashion, one can measure the ability of the candidate substance to modulate S1P activity.

It will, of course, be understood that all the screening methods of the present invention are useful in themselves notwithstanding the fact that effective candidates may not be found. The invention provides methods for screening, for such candidates, not solely methods of finding them.

III. DNA Delivery

One embodiment of the invention concerns the genetic transformation of a host cell with the constructs described herein. The transforming DNA may be stably integrated into the genome of the host cell or alternatively, the nucleic acid may be stably maintained in the cell as a separate, episomal segment of DNA. Such nucleic acid segments or "episomes" encode sequences sufficient to permit maintenance and replication independent of, or in synchronization with the host cell cycle. How the expression construct is delivered to a cell and where in the cell the nucleic acid remains is dependent on the type of expression construct employed. All expression constructs and delivery methods are contemplated for use in the context of the present invention, as outlined below.

(i) Transfection

In order to effect expression of a gene construct, the expression construct must be delivered into a cell. One efficient mechanism for delivery is via viral infection, where the expression construct is encapsidated in an infectious viral particle. However, several non-viral methods for the transfer of expression constructs into cultured mammalian cells also are contemplated by the present invention. In one embodiment of the present invention, the expression construct may consist only of naked recombinant DNA or plasmids. Transfer of the construct may be performed by any of the methods mentioned which physically or chemically permeabilize the cell membrane.

1. Liposome-Mediated Transfection

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al, 1987). Wong et al., (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

Melloul et al., (1993) demonstrated transfection of both rat and human islet cells using liposomes made from the cationic lipid DOTAP, and Gainer et al., (1996) transfected mouse islets using Lipofectamine-DNA complexes.

2. Electroporation

In certain other embodiments of the present invention, the expression construct is introduced into the cell via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner. Examples of electroporation of islets include Soldevila et al., (1991) and PCT application WO 91/09939.

3. Calcium Phosphate Precipitation or DEAE-Dextran Treatment

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

A preferred method of transforming using calcium phosphate comprises use of the MBS transfection kit, which is commercially available from Stratgene and was described by Hua et al., (1995).

4. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads. Gainer et al., (1996) have transfected mouse islets with a luciferase gene/human immediate early promoter reporter construct, using ballistic particles accelerated by helium pressure.

5. Direct Microinjection or Sonication Loading

Further embodiments of the present invention include the introduction of the expression construct by direct microinjection or sonication loading. Direct microinjection has been used to introduce nucleic acid constructs into Xenopus oocytes (Harland and Weintraub, 1985), and LTK$^-$ fibroblasts have been transfected with the thymidine kinase gene by sonication loading (Fechheimer et al., 1987).

6. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

7. Receptor Mediated Transfection

Still further expression constructs that may be employed to deliver a transforming construct to target cells arc receptor-mediated delivery vehicles. These take advantage of the selective uptake of macromolecules by receptor-mediated endocytosis that will be occurring in the target cells. In view of the cell type-specific distribution of various receptors this delivery method adds another degree of specificity to the transforming. Specific delivery in the context of mammalian cell typse is described by Wu and Wu (1993: incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987, 1988; Wagner et al., 1990; Ferkol et al., 1993; Perales et al., 1994; Myers, EPO 0273085), which establishes the operability of the technique.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al., (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

(ii) Viral Infection

1. Adenoviral Infection.

Another efficient means for delivery of the transforming constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue-specific transforming construct that has been cloned therein.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs) which arc cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP. (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a helper cell line, designated 293. which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$–$10^{11}$ plaque-forming units per ml, and they arc highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Recombinant adenovirus and adeno-associated virus (see below) can both infect and transduce non-dividing human primary cells. In fact, gene transfer efficiencies of approximately 70% for isolated rat islets have been demonstrated by the inventors (Becker et al., 1994a; Becker et al., 1994b; Becker et al., 1996) as well as by other investigators (Gainer et al., 1996).

2. AAV Infection

Adeno-associated virus (AAV) is an attractive vector system for use in the human cell transformation of the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin, et al., 1986; Lebkowski, et al., 1988; McLaughlin, et al., 1988), which means it is applicable for use with human neuroendocrine cells, however, the tissue-specific promoter aspect of the present invention will ensure specific expression of the transforming construct. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include Laface et al., (1988); Zhou et al., (1993); Flotte et al., (1993); and Walsh et al., (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi, et al., 1990; Walsh, et al., 1994; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski, et al., 1989; McLaughlin, et al., 1988; Kotin, et al., 1990; Muzyczka, 1992).

Typically, recombinant AAV (rAAV) virus is made by cotransfecting a plasmid containing the gene of interest flanked by the two AAV terminal repeats (McLaughlin el al., 1988; Samulski et al., 1989; each incorporated herein by reference) and an expression plasmid containing the wild type AAV coding sequences without the terminal repeats, for example pIM45 (McCarty et al,. 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regiions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

The present invention contemplates infection of the target cells with a recombinant adeno-associated virus (AAV) containing an oncogene driven by a tissue specific promoter. Recombinant AAV plasmids with RIP driving T antigen have been constructed.

3. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

4. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al., recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

(iii) Multiple Viral Infection

A further alternative for transforming a target cell is to use adenovirus or AAV infection of primary cells leading to in vitro expansion of a primary cell population that is then amenable to stable construct transfer by methods requiring cell growth such as retroviral transduction, plasmid transfection of expanding cells (Lipofectin or electroporation), or a second round of Adenovirus and/or AAV infection.

Another embodiment of the invention is to use alternating AAV and adenovirus infections. Propagation of AAV is dependent upon adenovirus, and using both viruses may lead to more productive infections. Such a method may increase the number of final cells that have transgenes integrated and expressed.

Multiple, sequential viral infections may allow one of skill in the art to exploit the benefits of various viral delivery systems and avoid their limitations. For example, a limitation of adenoviral gene delivery is that this system affords a very low rate of integration of viral and recombinant DNAs into the host cell genome. Consequently, adenoviral gene expression is diluted when the cells divide and typically is used only for transient gene expression. An advantage that adenoviral gene delivery has over many other viral vectors is that entry of the virus into the cell and the expression of transgenic proteins is not dependent on cellular replication. This benefit of adenoviral gene delivery is in contrast to retroviruses where the integration and sustained expression of virally introduced DNA is dependent on cellular replication.

The coupling of these two viral systems for the transformation of primary tissues minimizes the limitations of each and maximally exploits their distinct biological properties. For example, primary human pancreatic β-cells typically do not divide in culture and are thereby resistant to transformation by immortalizing gene constructs delivered by retroviruses. However, human β-cells can be infected with adenovirus for the purposes of transgenic protein expression.

In an exemplary embodiment, a target cell type would first be infected with a recombinant adenovirus that provides for the expression of a growth-promoting protein to stimulate cellular division. Cellular replication could be monitored by measuring thymidine incorporation or other techniques that have been developed to monitor DNA replication. In addition or alternatively, dividing cells could be enriched by FACS. Following the stimulation of cellular replication (about 12–96 hours following adenoviral infection), cells could be successfully infected with a recombinant retrovirus that has been engineered to express immortalizing gene products. The genomic DNA of a dividing cell population will be susceptible to stable integration by retrovirus and expression of recombinant proteins. This system of sequential and varied viral infections could further be optimized by the use of tissue-specific promoters for transgene expression in designated cell types and the expression of antibiotic resistance markers to selectively enrich for virally infected cells.

IV. Transformation Constructs

One embodiment of the current invention concerns host cells stably transformed with exogenous expression constructs. The methods generally comprise providing a construct that comprises an operative transforming unit under the transcriptional control of a promoter capable of directing expression in the target cell.

Mammalian cells may be transformed using, for example, infection with a recombinant virus, most preferably an adenovirus, that comprises the transforming construct. The methods described herein may involve the use of one, two, three or more distinct transforming genetic constructs. In certain aspects the use of defined media, or the use of defined media supplemented with one or more growth factors specific for the target cells is contemplated. Also contemplated is the use of one or more promoters that have enhanced transcriptional activity, such as promoters comprising multimerized promoter elements, the additional provision of a growth factor receptor gene to the target cell and/or the use of transforming genetic constructs that involve elements for effecting controlled or regulated expression or subsequent excision. The present section relates to the transforming genes and genetic constructs.

(i) Genes

Exemplary genes for preparation of transformation constructs include the hamster Site-1 protease sequence provided herein, as well as sequences used for the assays disclosed herein. The cDNA sequence of the hamster Site-1 protease is given in FIG. 12 (SEQ ID NO:2). The deduced amino sequence of the gene product is given in FIG. 11 (SEQ ID NO:1). The assays for Site-1 protease-specific inhibitors are not limited to the use of the hamster sequence, as homologous sequences may be used. For example, provided in FIG. 14 is the cDNA sequence of the Site-1 protease (SEQ ID NO:4), and provided in FIG. 13 is the amino acid sequence of the gene product. A Site-1 protease encoding sequence used in the preparation of a transformation construct in accordance with the invention may also comprise a cloned segment of genomic DNA comprising the Site-1 protease gene.

In order to assay the activity of a Site-1 protease, it will typically be necessary to include a target sequence for the protease. The target sequence may be comprised within an SREBP but the entire SREBP sequence is not necessarily required. Such target sequences will preferably include the amino acid sequence RSVLS in the case of Site-1 protease and LSLGII in the case of Site-2 protease (signal peptidase). SREBP sequences are known in the art and exemplified by Genbank Accession Numbers U02031, U09103, U00968, H92808, S66167 and s66168.

As studies have shown that SREBP cleavage activating protein (SCAP) is required for Site-1 protease activity, it may be desired to introduce transgenes encoding SCAP into host cells in accordance with the assays of the invention. The SCAP used will typically be one capable of binding with the COOH-terminal domain of the SREBPs. Potentially any SCAP capable of participating in the Site-1 protease cleavage reaction could be used. Exemplary SCAP sequences are provided by Genbank Accession numbers U67060, AA969178, AA862775, AA883810, and AA862769.

In particular embodiments, any of the foregoing, or other, sequences may be introduced to a host cell in one or more constructs. The inventors, therefore contemplate the use of several transforming gene constructs in combination. As an example of this embodiment, the transforming genetic construct may include more than one operative transforming unit, or more than one construct can be supplied.

(ii) Constitutive Promoters

Throughout this application, the term “expression construct” is meant to include any type of genetic construct containing a nucleic acid coding for a product in which part or all of the nucleic acid encoding sequence is capable of being transcribed. In order to obtain sufficient expression of a selected transgene, choice of a suitable promoter will be important. In particular, the promoter will preferably direct a high level of transgene expression specifically in the target cell type being analyzed.

Therefore, in preferred embodiments, the nucleic acid encoding a (gene product is under transcriptional control of a promoter. A "promoter" refers to a DNA sequence recognized by the synthetic machinery of the cell, or introduced synthetic machinery, required to initiate the specific transcription of a gene. The phrase "operably linked" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding a particular gene is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the gene of interest. The use of other viral or mammalian cellular or bacterial phage promoters which are well-known in the art to achieve expression of a gene of interest is contemplated as well, provided that the levels of expression are sufficient for a given purpose.

By employing a promoter with well-known properties, the level and pattern of expression of the gene product following transfection can be optimized. Further, selection of a promoter that is regulated in response to specific physiologic signals can permit inducible expression of the gene product. Tables 1 and 2 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

| ENHANCERS |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC CIass II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1 -Antitrypsin |
| H2B (TH2B) Histone |
| Mouse or Type I Collagen |
| Glucose-Regulated Proteins (GRP94 and GRP78) |
| Rat Growth Hormone |

TABLE 1-continued

| ENHANCERS |
|---|
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 2

| Element | Inducer |
|---|---|
| MT II | Phorbol Ester (TPA)<br>Heavy metals |
| MMTV (mouse mammary tumor virus) | Glucocorticoids |
| β-Interferon | poly(rI)X<br>poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

(iii) Cell Type-Specific Promoters

In certain aspects of the present invention, the expression of the transforming genetic construct is under the control of a promoter. The promoter may be required to express the transforming genetic construct to a degree sufficient to effect transformation of a target cell type amongst a population of different cell types such that the transformed target cell results in the generation of a stable transformant. Such embodiments may find use in assays comprising a particular cell type, or alternatively, for transgenic animals in which a marker gene is detected from a specific cell type potentially secreting the marker gene in proximity to the particular cell type.

Promoters can be classified into two groups? ubiquitous (constitutive) and tissue- or cell-specific. Ubiquitous promoters activate transcription in all or most tissues and cell types. Examples of ubiquitous promoters are cellular promoters like the histone promoters, promoters for many metabolic enzyme genes such as hexokinase I and glyceraldehyde-3-phosphate dehydrogenase, and many viral promoters such as CMVp and the Rous sarcoma virus promoter (RSVp).

Tissue- or cell-specific promoters activate transcription in a restricted set of tissues or cell types or, in some cases, only in a single cell type of a particular tissue. Examples of stringent cell-specific promoters are the insulin gene promoters which are expressed in only a single cell type (pancreatic D cells) while remaining silent in all other cell types, and the immunoglobulin gene promoters which are expressed only in cell types of the immune system.

Various exemplary tissue-specific promoters are shown above in Table 1 (Pearse and Takor, 1979; Nylen and Becker, 1995). Although not a complete list, these promoters are exemplary of the types of promoters which could be used with the present invention. Additional promoters useful in the present invention will be readily known to those of skill in the art.

As the present invention is applicable to the generation of stably transformed cells of potentially any tissue type, other context specific promoters may be employed. For example, the cell-specific prolactin gene promoter can be used to express a linked transgene selectively to lactotrophs surrounded by all the other cell types present in a pituitary cell preparation.

Examples of some other tissue-specific promoters include the glucagon promoter, GenBank accession number X03991; growth hormone promoter, GenBank accession numbers J03071 and K00470; POMC gene promoter, GenBank accession numbers V01510 and K02406; calcitonin promoter, GenBank accession number X15943; and the GIP gene promoter, GenBank accession number M31674.

1. Modified Promoters

Modified promoters could also be used with the current invention. Promoters can be modified in a number of ways to increase their transcriptional activity. Multiple copies of a given promoter can be linked in tandem, mutations which increase activity may be introduced, single or multiple copies of individual promoter elements may be attached, parts of unrelated promoters may be fused together, or some combination of all of the above can be employed to generate highly active promoters. All such methods are contemplated for use in connection with the present invention.

German et al., (1992) mutated three nucleotides in the transcriptionally important FLAT E box of the rat insulin I gene promoter (RIP), resulting in a three- to four-fold increase in transcriptional activity of the mutated RIP compared to that of a nonmutated RIP as assayed in transiently transfected HIT cells. Also, the introduction of multiple copies of a promoter element from the *E. coli* tetracycline resistance operon promoter were introduced into the CMV promoter, significantly increasing the activity of this already very potent promoter (Liang et al., 1996). Additionally, part of the CMV promoter, which has high but short-lived transcriptional activity in dog myoblasts, was linked to the muscle-specific creatine kinase promoter (MCKp), which has weak but sustained expression in dog myoblasts, resulting in a hybrid promoter that sustained high-level expression for extended periods in dog myoblasts.

2. Multimerized Promoters

Several modified rat insulin promoters (modRIP) containing multimerized enhancer elements have been engineered. The currently preferred modRIP contains six multimerized repeats of a 50 base pair region of the cis acting enhancer of RIP, placed upstream of an intact copy of RIP.

These novel promoters have been shown to direct expression of transgenes in stably engineered β cell lines at levels above those attained with unmodified insulin promoters and, in some cases, approaching the levels achieved with the Cytomegalovirus promoter (CMVp). CMVp is one of the strongest activating promoters known, but in a very non-tissue specific manner. Therefore, the present modified rat insulin promoters can be used to direct the tissue specific expression of transforming genes at levels presently achievable only with the non-specific CMVp.

(iv) Other Regulatory Elements

Where a cDNA insert is employed, one will typically desire to include a polyadenylation signal to effect proper polyadenylation of the gene transcript. The nature of the polyadenylation signal is not believed to be crucial to transgene expression and any such sequence may be employed. Also contemplated as an element of the expression cassette is a terminator. These elements can serve to enhance message levels and to minimize read through from the cassette into other sequences.

(v) Selectable Markers

In certain embodiments of the invention, the delivery of a nucleic acid in a cell may be identified in vitro or in vivo by including a marker in the expression construct. The marker would result in an identifiable change to the transfected cell permitting easy identification of expression. Usually the inclusion of a drug selection marker aids in cloning and in the selection of transformants, for example, neomycin, puromycin, hygromycin, DHFR. GPT, zeocin and histidinol. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(vi) Multigene constructs find IRES

In certain embodiments of the invention, internal ribosome binding sites (IRES) elements can be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologeous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted marker proteins, multi-subunit proteins, encoded by independent genes, intracellular or membrane-bound proteins and selectable markers. In this way, expression of several proteins can be simultaneously engineered into a cell with a single construct and a single selectable marker.

V. Site Specific Integration or Excision of Transgenes

It is specifically contemplated by the inventors that one could employ techniques for the site-specific integration or excision of transformation constructs prepared in accordance with the instant invention. Site-specific integration or excision of transgenes or parts of transgenes can be achieved by means of homologous recombination (see, for example, U.S. Pat. No. 5,527,695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore the choice of homologous sequences contained on the introduced DNA will determine the site where the introduced DNA is integrated via homologous recombination. For example, if the DNA sequence of interest is linked to DNA sequences sharing homology to a single copy gene of a host cell, the DNA sequence of interest will be inserted via homologous recombination at only that single specific site. Hlowever, if the DNA sequence of interest is linked to DNA sequences sharing homology to a multicopy gene of a host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant invention, including, but not limited to, the Cre/lox system of bacteriophage PI (U.S. Pat. No. 5,658,772, specifically incorporated herein by reference in its entirety), the FLP/FRT system of yeast (Golic and Lindquist, 1989), the Gin recombinase of phage Mu (Maeser et al., 1991), the Pin recombinase of *E. coli* (Enomoto et al., 1983), and the R/RS system of the pSR1 plasmid (Araki et al., 1992). The bacteriophage P1 Cre/lox and the yeast FLP/FRT systems constitute two particularly useful systems for site specific integration or excision of transgenes. In these systems a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently in eukaryotic cells. Experiments on the performance of the FLP/FRT system indicate that FRT site structure, and amount of the FLP protein present, affects excision activity. In general, short incomplete FRT sites lead to higher accumulation of excision products than the complete full-length FRT sites. The systems can catalyze both intra- and intermolecular reactions, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

The present invention also contemplates the use of recombination activating genes (RAG) 1 and 2 to rescue specific genes from the genome of transformed cell lines. RAG-1 (GenBank accession number M29475) and RAG-2 (GenBank accession numbers M64796 and M33828) recognize specific recombination signal sequences (RSSs) and catalyze V(D)J recombination required for the assembly of immunoglobulin and T cell receptor genes (Schatz et al., 1989; Oettinger et al., 1990; Cumo and Oettinger, 1994). Transgenic expression of RAG-1 and RAG-2 proteins in non-lymphoid cells supports V(D)J recombination of reporter substrates (Oettinger et al., 1990). For use in the present invention, the transforming construct of interest is engineered to contain flanking RSSs. Following transformation, the transforming construct that is internal to the RSSs can be deleted from the genome by the transient expression of RAG-1 and RAG-2 in the transformed cell.

VI. Cell Cultures

In one embodiment of the invention, cells will be grown in culture. The present section describes the methodology related to growth of cells in culture.

(i) Culture Conditions

Primary cells are expanded by established culture conditions. For example, a particular cell line can be cultured and even induced to divide as described (Clark and Chick, 1990; Beattie et al., 1991; Hayek et al., 1995; each incorporated herein by reference).

Culture conditions are achieved by manipulating various cell culture parameters such as: media growth/survival factors (such as IGF-1, growth hormone, prolactin, PDGF. hepatocyte growth factor, and transferrin), media differentiation factors (such as TGF-β), media lipids, media metabolites (such as glucose, pyruvate, galactose, and amino acids), media serum (percentage serum, serum fraction, species of serum), gaseous exchange (ratio atmospheric $O_2$:$CO_2$, and media volume), and extracellular substrate for cellular attachment (such as laminin, collagen, matrigel, and HTB-9 bladder carcinoma derived matrix).

(ii) Defined Media

Media may be used comprising one or more growth factors that stimulate the growth of a target cell type and do not substantially stimulate growth of distinct cells in the cell population; i.e., act to induce preferential growth of the target cells rather than faster-growing more hardy cells in the population, as may be used to deplete fibroblasts. Examples include defined serum free conditions (Clark et al., 1990; incorporated herein by reference), or inclusion of growth or differentiation factors (WO 95/29989; incorporated herein by reference).

(iii) Proliferation

Cells may be induced to proliferate by initial infection with adenovirus or adeno-associated virus (AAV) comprising a gene that induces cellular proliferation, the gene being under the control of a promoter specific for the target cell. The cells may be induced to proliferate by growth on a stimulatory cell matrix (Hayek et al., 1995).

Cells prepared in accordance with the present invention may be present propagated as non-anchorage dependent cells growing freely in suspension throughout the bulk of a culture; or as anchorage-dependent cells requiring attachment to a solid substrate for their propagation (i.e., a monolayer type of cell growth) (WO publication number 97/26334; and WO publication number 97/26321, the disclosures of which are specifically incorporated herein by reference in their entirety and describe the different modes of cell culture that can be employed to maintain cells used with the present invention.

In particular embodiments, the cells that will be used for the screening of modulators of Site-1 protease activity may be in a microcarrier culture (van Wezel, 1967). This mode of the culture propagation on the microcarriers makes it possible to use this system for cellular manipulations such as cell transfer without the use of proteolytic enzymes, cocultivation of cells, transplantation into animals, and perfusion of the culture using decanters, columns, fluidized beds, or hollow fibers for microcarrier retainment.

As described herein, particular embodiments, employ microencapsulation of cells because this system readily lends itself to batch screening methods such as 96-well plate screening and also provides a useful mode of providing the cells to an animal model for in vivo testing. The cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquified by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150–1500 $\mu$m in diameter, are easily retained in a perfused reactor using a fine-meshed screen. The ratio of capsule volume to total media volume can kept from as dense as 1:2 to 1:10. With intracapsular cell densities of up to $10^8$, the effective cell density in the culture is $1–5\times10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for use in 96-well screening assays and in implantation.

The cells prepared in accordance with the present invention may, irrespective of the culture method chosen, be used in protein production and as cells for in vitro cellular assays and screens as part of drug development protocols.

VII. Purification Techniques

Purification techniques may find use in the current invention, for example, in the purification of a marker gene product or for the purification of the S1P protein. Purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%. about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

VIII. In vivo Uses

The inventors specifically contemplate the therapeutic use of an S1P protease inhibitor identified with the assays of the invention. In such application, the S1P protease inhibitor is preferably administered as a pharmaceutical composition comprising a pharmaceutically or pharmacologically acceptable diluent or carrier. The nature of the carrier is dependent on the chemical properties of the compounds, including solubility properties, and/or the mode of administration. For example, if oral administration is desired, a solid carrier may be selected, and for i.v. administration a liquid salt solution carrier may be used.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

(i) Parenteral administration

One means of administering a therapeutic agent comprises use of formulations for parenteral administration, e.g., formulated for injection via the intravenous, intramuscular, sub-cutaneous or other such routes, including direct instillation into a tumor or disease site. The preparation of an aqueous composition for inhibition of S1P activity will be known to those of skill in the art in light of the present disclosure. Typically, such compositions can be prepared as injectables, either as liquid solutions or suspensions, solid forms suitable for using to prepare solutions or suspensions upon the addition of a liquid prior to injection also can be prepared; and the preparations also can be emulsified.

Solutions of an active compound as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The active compounds can be formulated into a composition in a neutral or salt form. Pharmaceutically acceptable salts include the acid addition salts (formed with the free amino (groups of the protein) which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying, and freeze-drying techniques which yield a powder of the active ingredient plus any additional desired ingredient from a previously sterile-filtered solution thereof.

(ii) Other modes of administration

Other modes of administration may also be employed. For instance, an S1P inhibitor may be formulated in suppositories and, in some cases, aerosol and intranasal compositions. For suppositories, the vehicle composition will include traditional binders and carriers such as polyalkylene glycols or triglycerides. Such suppositories may be formed from mixtures containing the active ingredient in the range of about 0.5% to about 10% (w/w), preferably about 1% to about 2%.

Oral compositions may be prepared in the form of solutions, suspensions, tablets, pills, capsules, sustained release formulations, or powders. These compositions can be administered, for example, by swallowing or inhaling. Where a pharmaceutical composition is to be inhaled, the composition will preferably comprise an aerosol. Exemplary procedures for the preparation of aqueous aerosols for use with the current invention may be found in U.S. Pat. No. 5,049,388, the disclosure of which is specifically incorporated herein by reference in its entirety. Preparation of dry aerosol preparations are described in. for example, U.S. Pat. No. 5,607,915, the disclosure of which is specifically incorporated herein by reference in its entirety.

Also useful is the administration of the invention compounds directly in transdermal formulations with permeation enhancers such as DMSO. These compositions can similarly include any other suitable carriers, excipients or deluents. Other topical formulations can be administered to treat certain disease indications. For example, intranasal formulations may be prepared which include vehicles that neither cause irritation to the nasal mucosa nor significantly disturb ciliary function. Diluents such as water, aqueous saline or other known substances can be employed with the subject invention. The nasal formulations also may contain preservatives such as, but not limited to, chlorobutanol and benzalkonium chloride. A surfactant may be present to enhance absorption of the subject compounds by the nasal mucosa.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of the Expression Vector pCMV-PLAP-BP2 and the Development of a Sterol Dependent Alkaline Phosphatase Assay for S1P

MATERIALS AND METHODS

General Methods and Materials

Standard molecular biology techniques were used (Sambrook et al., 1989). The Phospha-Light™ Reporter Gene Assay System and Luminescent β-Galactosidase Genetic Reporter System II were purchased from Tropix (Bedford, Mass.) and Clontech, Palo Alto, Calif., respectively. Total cellular RNA was obtained with RNA-DNA STAT 60 (Tel-Test, Inc.), and poly(A)+ RNA was isolated with an mRNA Purification Kit (Pharmacia Biotech). cDNA probes were radiolabeled by random priming with [α-32P] dCTP using the Megaprime DNA Labeling System (Amersham, Arlington Height, Ill.). Plasmid pCMVβ-gal, encoding a β-galactosidase reporter driven by the CMV promoter/enhancer, was obtained from Stratagene, La Jolla, Calif. Plasmids pcDNA 3 and 3.1, which are empty vectors containing the CMV promoter/enhancer, were obtained from Invitrogen, San Diego, Calif. The inventors obtained monoclonal antibody HSV-Tag™ (IgG1) from Novagen, monoclonal antibody anti-c-Myc (clone 9E10) (IgG1) from Boehringer Mannheim, Indianapolis, Ind., a polyclonal affinity-purified donkey anti-mouse IgG from Jackson Immunoresearch Laboratories (West Grove, Pa.); and glycosidase from New England Biolabs (Beverly, Mass.). Lipoprotein-deficient serum (d>1.215 g/ml) was prepared as previously described (Goldstein et al., 1983).

Cell Culture

All cells were maintained in monolayer culture at 37° C. in 8–9% $CO_2$CHO-7 cells are a clone of CHO-K1 cells selected for growth in newborn calf lipoprotein-deficient serum (Metherall et al., 1989). M19 cells are a clone of amphotericin-resistant CHO-K1 cells that are auxotrophic for cholesterol and unsaturated fatty acids (Hasan et al., 1994) owing to a deletion in the S2P gene (Rawson et al., 1997). CHO/pS2P cells (Rawson et al., 1998) are a clone of CHO-7 cells that have been stably transfected with pCMV-HSV-S2P, a CMV-driven plasmid that encodes the human Site-2 protease (Rawson et al., 1998). SRD-12A and SRD-12B cells are previously described cholesterol and unsaturated fatty acid auxotrophs that were derived from γ-irradiated CHO/pS2P cells and selected using an amphotericin B resistance protocol (Rawson et al., 1998). Stock cultures of CHO-7 cells were maintained in medium A (a 1:1 mixture of Ham's F12 medium and Dulbecco's modified Eagle medium containing 100 U/ml penicillin and 100 μg/ml streptomycin sulfate) supplemented with 5% (v/v) newborn or fetal calf lipoprotein-deficient serum. Stock-cultures of CHO/pS2P cells were maintained in medium A supplemented with 5% fetal calf lipoprotein-deficient serum, 2 μM compactin, and 500 μg/ml G418. Stock cultures of SRD-12A, SRD-12B, and M19 cells were maintained in medium B (medium A supplemented with 5% fetal calf serum, 5 μg/ml cholesterol, 1 mM sodium mevalonate, and 20 μM sodium oleate). Human embryonic kidney 293 cells were maintained in medium C (Dulbecco's modified Eagle medium containing 100 U/ml penicillin and 100 μg/ml streptomycin sulfate) supplemented with 10% fetal calf serum.

Construction of pCMV-PLAP-BP2(513–1141)

The expression vector pCMV-PLAP-BP2(513–1141) encodes an 1135-amino acid fusion protein consisting of an initiator methionine followed by the secreted form of human placental alkaline phosphatase (SEQ ID NO:59), one novel amino acid (Y) generated by blunt ligation, and the COOH-terminal half of human SREBP-2 (amino acids 513–1141, SEQ ID NO:60) (FIG. 1). pCMV-PLAP-BP2(513–1141) was constructed as follows. First, pCMV/SEAP (purchased from Tropix) encoding the secreted form of human placental alkaline phosphatase (Cullen and Malim, 1992) was cleaved with HpaI and XbaI to remove the stop codon and the 3' untranslated sequence. The inventors isolated the 7.5-kb fragment of the vector containing the CMV promoter/enhancer region and the coding region of human placental alkaline phosphatase (SEQ ID NO:59). Second, pTK-HSV-BP2 (Hua et al., 1996b) was mutagenized by oligonucleotide site-directed mutagenesis (Kunkel et al., 1987; Hua et al., 1996b) to generate an EcoRV restriction site at the codons encoding amino acids 511 and 512 of SREBP-2. This intermediate construct was digested with EcoRV and XbaI to isolate a 2.6-kb fragment encoding amino acids 513 to 1141 of SREBP-2. The 2.6-kb EcoRV-Xbal fragment was blunt-ligated inframe with the HpaI/XbaI-digested pCMV/SEAP vector, introducing a single tyrosine residue at the boundary between the alkaline phosphatase and SREBP-2 fusion protein to yield pCMV-PLAP-BP2(513–1141). The S13F/G15I and R519A mutant versions of this plasmid were constructed by site-directed mutagenesis (Kunkel et al., 1987; Hua et al., 1996b). The final structures of all plasmids were confirmed by sequencing all ligation junctions.

cDNA Transfection

On day 0 human embryonic kidney 293 cells were set up at a density of $4\times10^5$ cells/60-mm dish in medium C supplemented with 10% fetal calf serum. On day 2, duplicate dishes of 293 cells were transfected with the indicated plasmids by the calcium phosphate method using the MBS Transfection Kit (Stratagene) as previously described (Hua et al., 1995). After incubation for 3 h, the cells were washed once with phosphate-buffered saline (PBS) and fed with 5 ml of medium D (medium C supplemented with 10% newborn calf lipoprotein-deficient serum, 50 μM compactin, and 50 μM sodium mevalonate) in the absence or presence of sterols (1 μg/ml of 25-hydroxycholesterol plus 10 μg/ml of cholesterol added in ethanol at a final concentration of 0.2%). After incubation for 16 h, aliquots of 1 ml of medium were removed for assay of alkaline phosphatase as described below. CHO-7 and SRD-12B cells were transfected as follows. On day 0, cells were set up at a density of $4\times10^4$ cells/22-mm well in medium B. On day 1, duplicate wells of cells were transfected with the indicated plasmids using the LipofectAMINE PLUS™ reagent (Life Technologies) according to the manufacturer's instructions with modifications as follows. The inventors used a total of 1.26 μg of plasmid DNA, 4.5 μl of LipofectAMINE™ reagent, and 4 μl of PLUS™ reagent per well in a final volume of 0.4 ml. After incubation for 3 h, the medium was removed, and the cells were fed with 2 ml of medium A supplemented with 5% fetal calf serum without washing. After incubation for 16 h, aliquots of 1 ml of medium were removed for assay of alkaline phosphatase.

Assay for Secreted Alkaline Phosphatase

Cells were transfected with pCMV-PLAP-BP2 (513–1141) as described above. After the indicated interval, aliquots of medium were removed and spun at top speed (14,000 rpm) in an Eppendorf microcentrifuge (model 5417C) for 20 min at 4° C. The supernatant was treated at 65° C. for 30 min to inactivate non-placental alkaline phosphatase, after which an aliquot (33 μl) was assayed for placental alkaline phosphatase activity with the Tropix Phospha-Light™ assay using the substrate and reaction conditions recommended by the manufacturer. The total volume of the assay was 300 μl. After 10 to 20 min, chemiluminescence was quantified on an Optima II luminometer (MGM Instruments).

After removal of the medium, the cells were lysed with 0.2 ml of 1× Reporter Lysis Buffer (Promega, Madison, Wis., and aliquots (5 μl) were used for measurement of β-galactosidase activity. The β-galactosidase assay was carried out with the Genetic Reporter System II kit (Clontech). This method generated a chemiluminescent product that was quantified by luminometry. To account for differences in transfection efficiency the amount of alkaline phosphatase activity in the medium was corrected for the amount of β-galactosidase activity in the cells.

RESULTS

FIG. 1 shows the fusion protein that the inventors developed to monitor the activity of S1P. The $NH_2$-terminus consists of amino acids 1–506 of human placental alkaline phosphatase (PLAP) beginning with the signal peptide. The protein terminates at residue 506, which precedes the hydrophobic sequence that normally serves as the signal for attachment of a glycophospholipid anchor to the alkaline phosphatase (Cullen and Malim, 1992). If this protein were ever to be released into the lumen of the ER, it is predicted to be soluble. The PLAP is fused to SREBIP-2 at amino acid position 513, which is 6 residues to the $NH_2$-terminal side of the RSVLS sequence (SEQ ID NO:10) that is cleaved by S1P. The SREBP-2 sequence includes the second transmembrane domain and the entire COOH-terminal regulatory domain that projects into the cytosol. PLAP-BP2 is predicted to be cleaved cotranslationally by signal peptidase. The PLAP should remain membrane-bound unless it is cleaved from the SREBP-2 by S1P, whereupon it should be secreted into the culture medium. The bottom of FIG. 1 shows the amino acid sequences surrounding the two cleavage sites.

Figure 2A:
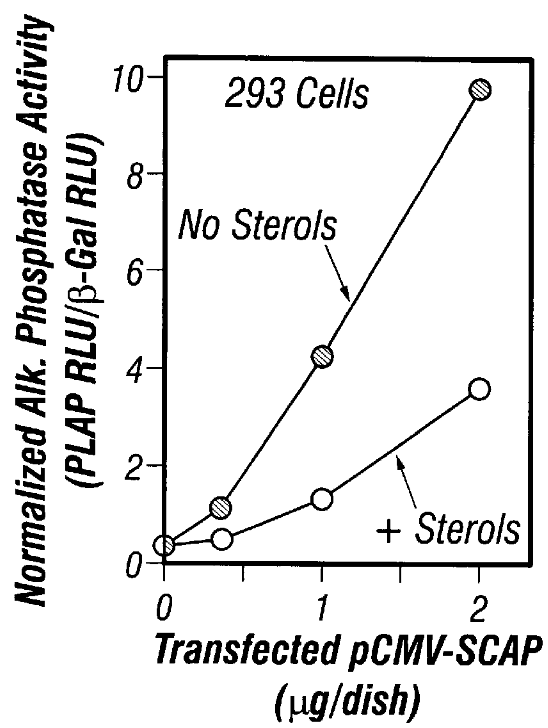
FIG. 2A. Duplicate 60-mm dishes of 293 cells were transfected with 2 μg of pCMV-PLAP-BP2(513–1141), 0.01 μg of pCMVβ-gal, and the indicated amount of pCMV-SCAP. The total amount of DNA was adjusted to 6 μg/dish by addition of pcDNA 3 empty vector. After transfection, the cells were incubated for 16 h in medium D in the absence (●) or presence (o) of sterols as described in Experimental Procedures.

To demonstrate that PLAP-BP2 would be cleaved in the predicted fashion, the inventors introduced the PLAP-BP2 cDNA into human kidney 293 cells by transfection under control of the CMV promoter (FIG. 2A). Increasing amounts of a plasmid encoding wild-type SCAP, also under the control of the CMV promoter, were similarly transfected into the cells. Alkaline phosphatase activity was measured in the medium by a sensitive chemiluminescence assay after inactivating nonplacental alkaline phosphatase by heat treatment (Cullen and Malim, 1992). In the absence of cotransfected SCAP, virtually no PLAP was secreted into the medium (FIG. 2A). The amount of secreted PLAP activity rose linearly as the amount of transfected pCMV-SCAP was increased. When the 293 cells were incubated in the presence of a mixture of cholesterol plus 25-hydroxycholesterol, PLAP secretion was reduced. The requirement for SCAP and the suppression by sterols demonstrated that PLAP secretion depends upon S1P. The results also indicate the efficacy of the assay in quantifying S1P activity.

Figure 2B:
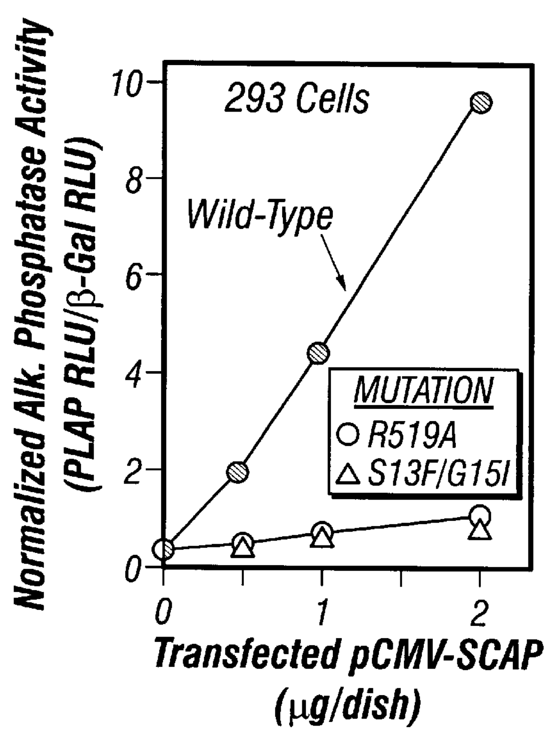
FIG. 2B. Duplicate 60-mm dishes of 293 cells were transfected with 2 μg of the wild-type (●) or the indicated mutant (Δ, o) version of pCMV-PLAP-BP2 (513–1141), 0.01 μg of pCMVβ-gal, and the indicated amount of pCMV-SCAP. After transfection, the cells were incubated for 16 h in medium D in the absence of sterols.

To confirm the role of signal peptidase and S1P in PLAP secretion, the inventors prepared constructs encoding two mutant versions of the fusion protein. In one mutant, the arginine of the RSVLS sequence (SEQ ID NO:10) at Site-1 was changed to alanine (R519A). Previous studies have shown that this mutation decreases the susceptibility of SREBP-2 to cleavage by S1P (Duncan et al., 1997). In the second mutant, two amino acids near the signal peptidase cleavage site were changed (S13F/G15I). These substitutions are predicted to block cleavage by signal peptidase (van Heijne, 1985). The secretion of PLAP was markedly reduced when the fusion protein bore either the signal peptidase mutations or the Site-1 cleavage mutation (FIG. 2B).

Figure 2C:
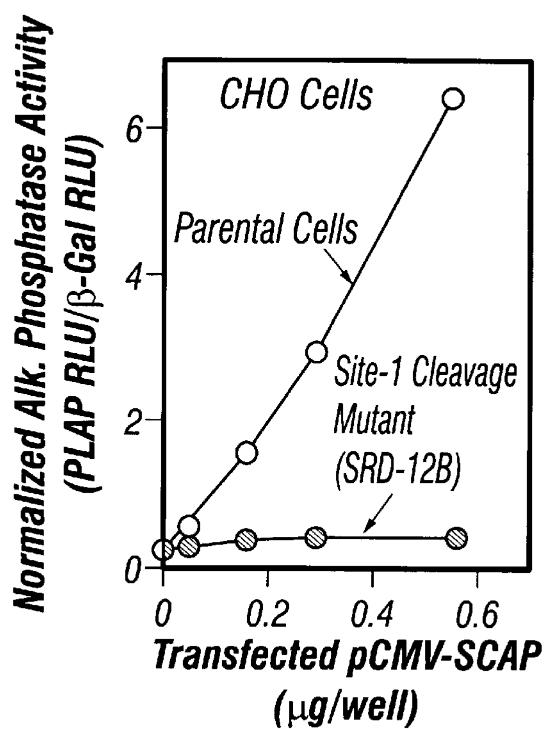
FIG. 2C. Duplicate 22-mm wells of CHO-7 cells (o) or SRD-12B cells (●) were transfected with 0.1 μg of pCMV-PLAP-BP2(513–1141), 0.01 μg of pCMVβ-gal, and the indicated amount of pCMV-SLAP). The total amount of DNA was adjusted to 1.26 μ/well by addition of pcDNA 3 empty vector. After transfection, the cells were cultured in medium A supplemented with fetal calf lipoprotein-deficient serum in the absence of sterols.

As a final test for the requirement for S1P in the secretion of PLAP, the inventors introduced the construct into wild-type CHO cells and into SRD-12B cells that lack S1P activity (Rawson et al., 1998) (FIG. 2C). Whereas the wild-type cells secreted PLAP into the medium, the SRD-12B cells were almost totally deficient in this secretion.

Example 2

Expression Cloning and Sequence Analysis of Hamster S1P

MATERIALS AND METHODS

Expression Cloning of Hamster Site-1 Protease (S1P)

The inventors used pools of hamster cDNAs from an expression library that was previously described (Hua et al., 1996a). Expression was driven by the CMV promoter/enhancer. Pools of cDNAs from the library were transfected into SRD-12B cells together with three supporting plasmids as described below. On day 0, replicate wells of SRD-12B cells ($1\times10^5$ cells/22-mm well) were plated in medium B. On day 1, duplicate wells of cells were transfected with the following plasmids: 1 $\mu$g of a cDNA pool; 0.21 $\mu$g ofpCMV-SCAP (Sakai et al., 1997); 0.04 $\mu$g of pCMV-PLAP-BP2 (513–1141); and 0.01 $\mu$g of pCMVβ-gal using the LipofectAMINE PLUS™ transfection method as described above. After incubation for 3 h, the medium was removed, and the cells were fed with 2 ml of medium A supplemented with 5% fetal calf serum without washing. After 16 h, the medium was removed, heat-treated, and analyzed for alkaline phosphatase activity. The cells were harvested and assayed for β-galactosidase activity as described above.

The average value for alkaline phosphatase activity in cells transfected with the plasmid cDNAs pools was 0.2 relative light unit of alkaline phosphatase per relative light unit of β-galactosidase. In a screen of 300 pools of 1000 cDNAs per pool, two positive pools gave a normalized value of 4 to 9 fold higher than the background value of 0.2 and were considered positive. The DNA from one of these pools (No. 116) was transformed into *E. coli* DH5a. cells to generate multiple pools of ~100 independent transformants per pool. These plasmid pools were transiently transfected into SRD-12B cells along with the three supporting plasmids as described above. After 16 h, the inventors assayed for secreted alkaline phosphatase and cellular β-galactosidase activities as described above. Plasmid DNA from one positive pool of 100 cDNAs was retransformed into *E. coli*, and 121 colonies from this transformation were randomly picked and plated onto an 11×11 matrix. Bacterial cultures were prepared from pooled colonies from each row and column of the matrix. Plasmids were isolated from each of these pooled cultures and transfected into SRD-12B cells together with the three supporting plasmids. The inventors then assayed for secreted alkaline phosphatase and cellular β-galactosidase activities. Two positive rows and columns were identified. Plasmids were isolated from the individual bacterial colonies at the intersection of the positive rows and columns. These pure plasmids were transfected into SRD-12B cells as described above, and the medium was assayed for secreted alkaline phosphatase activity. As expected, two of the four plasmids gave positive results. These two cDNA clones, designated p38 and p80, were identical by restriction mapping and partial DNA sequencing. Subsequent studies were carried out with clone p38, which is hereafter designated pCMV-S1P. Both DNA strands of pCMV-S1P were sequenced with vector-specific or insert-specific primers by the dideoxy chain termination method (Sanger et al., 1980). Sequencing reactions were performed on Applied Biosystems Model 373A and 377 DNA sequencers.

RESULTS

The secretion of PLAP was then used as an assay for the cloning of S1P by transient complementation of the defect in SRD-12B cells. For this purpose, pools were tested of 1000 cDNAs each that were prepared from an unamplified expression library that was produced previously from CHO cell mRNA (Hua et al., 1996a). Expression of the cDNAs was driven by the CMV promoter. The pooled cDNAs were introduced into SRD-12B cells together with cDNAs encoding PLAP-BP2 and SCAP. To correct for varying efficiencies of transfection, a cDNA encoding β-galactosidase was also included. After 19 h the medium was removed, heat-treated, and assayed for PLAP. The cells were harvested and assayed for β-galactosidase activity. The results were expressed as the ratio of PLAP activity in the medium divided by the β-galactosidase activity in the cells.

Figure 3A:
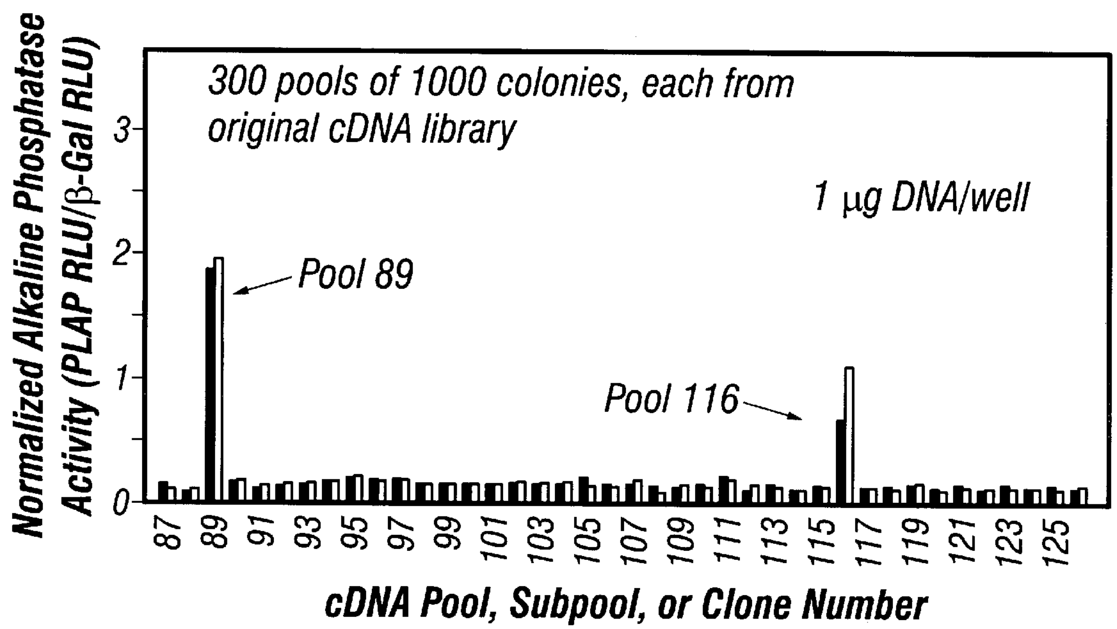
FIG. 3A. 300 pools, each containing $1\times10^3$ independent cDNAs from the hamster cDNA library, were transfected into SRD-12B cells. The medium was assayed for placental alkaline phosphatase. and the cells were assayed for β-galactosidase. Alkaline phosphatase activity (relative light units) was normalized to cellular β-galactosidase activity (relative light units). This panel shows the data for 40 of the 300 pools that were assayed on the same day in one experiment.
Figure 3B:
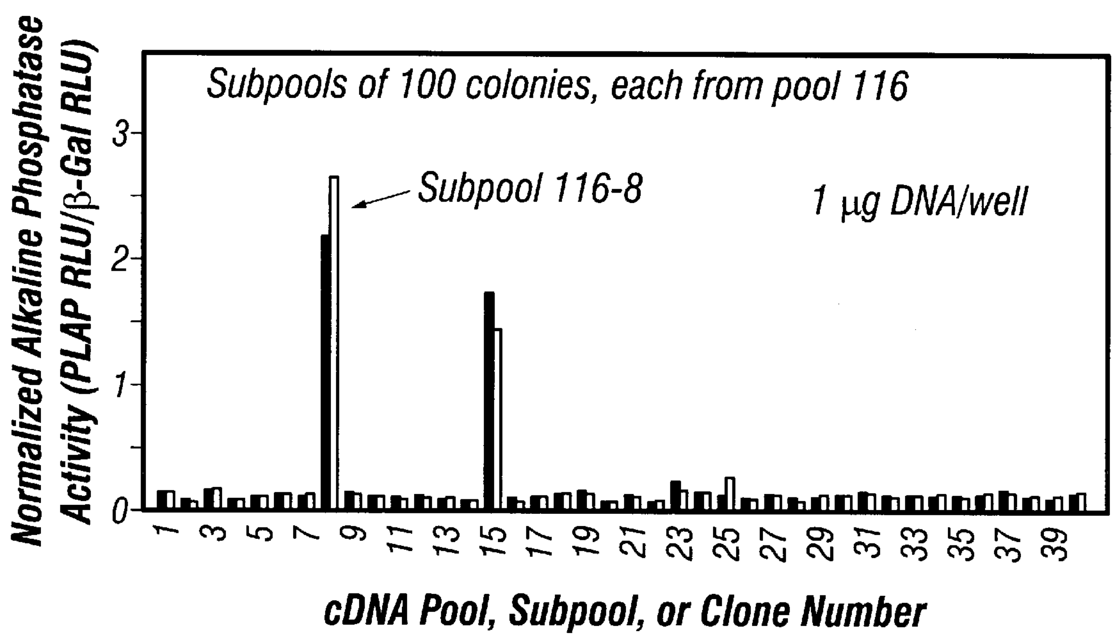
FIG. 3B. The positive pool No. 116 from Panel A was subdivided into 40 subpools of 100 colonies each. The pooled DNA was transfected, and assays were performed as described above.
Figure 3C:
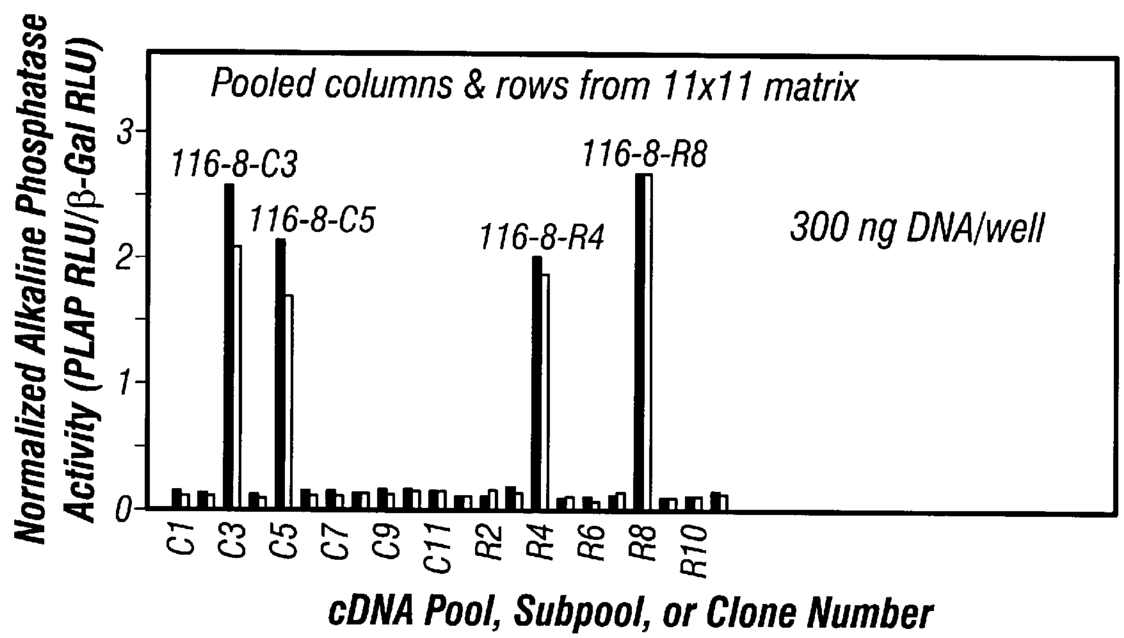
FIG. 3C. 121 colonies from subpool No. 116–8 from Panel B were randomly selected and plated onto an 11×11matrix. Pooled bacterial cultures were prepared from each column (C1–C11) and each row (R1–R11). cDNAs from each pool were transfected into SRD-12B cells. Four positive pools were identified.
Figure 3D:
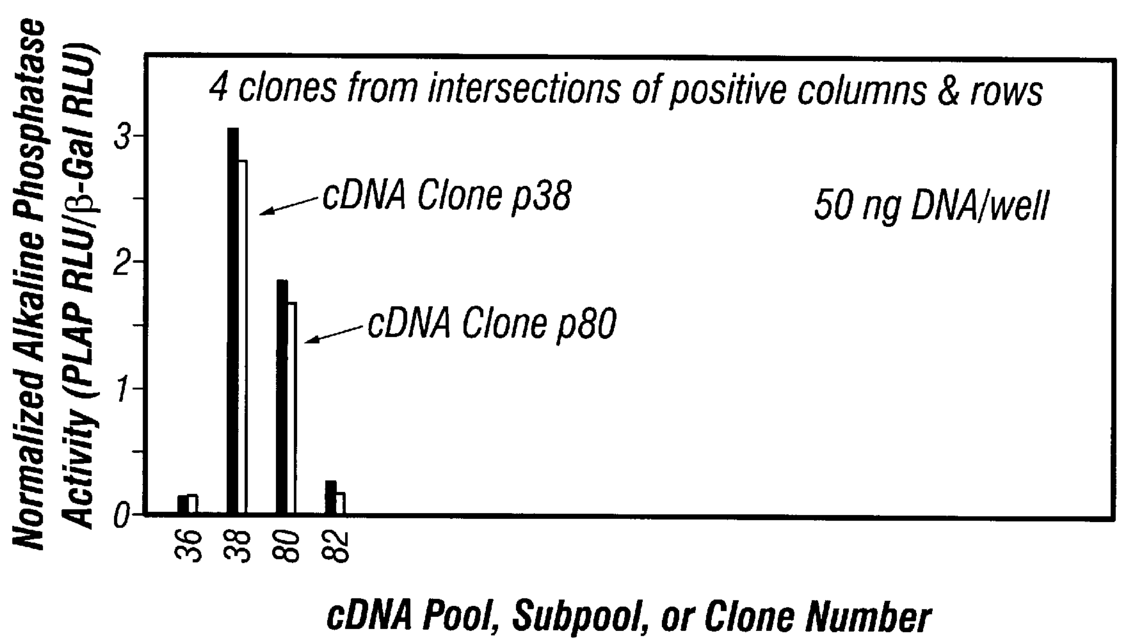
FIG. 3D. Each of the four clones at the intersection of the positive rows and columns of the matrix analysis were assayed for secreted alkaline phosphatase activity.

A total of 300 pools of 1000 cDNAs each were studied. Two pools were found to stimulate PLAP secretion to levels that were significantly higher than background. FIG. 3A shows the results of one such assay conducted with 40 pools, including the two positive pools (numbers 89 and 116). Pool 116 was divided into subpools of 100 colonies each. Two of these subpools gave positive results (FIG. 3B). Individual colonies were then plated from subpool 116-8 into individual wells of an 11×11 matrix. cDNAs were prepared from the pooled rows and columns of the matrix as described in the Examples section, below. Four of these pools gave positive results (FIG. 3C). Individual clones were then assayed from the wells at the intersections of the positive rows and columns. As expected, two of these were positive. Restriction maps suggested that these clones had identical inserts, and cDNA clone p38 for further studies.

cDNA clone p38 was found to contain a large open reading flame that encodes a protein of 1052 amino acids with a calculated molecular mass of 117.5 kDa (FIG. 4). The initial 17 amino acids are hydrophobic and appear to represent a signal peptide. The hydrophobic sequence terminates at a glycine, which is an ideal substrate for signal peptidase (von Heijne, 1985). Hereafter, the protein encoded by p38 was termed S1P.

Sequence Analysis of S1P

Database searches revealed that S1P has features characteristic of a superfamily of serine proteases, broadly classified as subtilisins, which are found in all living organisms from bacteria to humans (Siezen and Leunissen, 1997). The human counterpart of hamster S1P was sequenced previously from a random library of sequences expressed in KG1 cells. an immature myeloid cell line. The EDNA sequence was designated KIAA0091 (GenBank Accession No. D42053). Although the function of the KIAA0091 gene product was not known, it was classified as a member of the subtilisin family, and its sequence has been included in a comparative analysis of this family by Siezen and Leunissen (1997), who referred to the KIAA0091 sequence as "hskiaa." Overall, the amino acid sequence of hamster S1P is 97% identical to the sequence of human hskiaa. Nearly all of the substitutions are conservative (FIG. 4).

Subtilisins, like other serine proteases, contain a catalytic triad consisting of an aspartic acid, a histidine, and a serine residue. Based on the resemblance to other members of the subtilisin family, the sequence of S1P predicts that its catalytic triad should consist of Asp218, His249, and Ser414 of SEQ ID NO:1 (Siezen and Leunissen, 1997).

Other notable features of the S1P sequence include six potential sites of N-linked glycosylation (Asn-X-Ser/Thr) (X can be any amino acid other than proline; see Marshall, 1972) (designated by 3 dots in FIG. 4). Near the COOH-terminus, there is an unbroken stretch of 25 nonpolar residues, which is consistent with a membrane-spanning sequence (thick overline in FIG. 4). This is followed by a sequence of 30 amino acids that is strikingly rich in prolines and basic residues (6 prolines and 11 basic residues without a single acidic residue).

Example 3

Construction of an Epitope Tagged S1P and its Intracellular Detection

MATERIALS AND METHODS

Construction of Epitope-tagged pCMV-Myc-S1P pCMV-Myc-S1P encodes an epitope-tagged version of pCMV-S1P in which the c-Myc epitope was placed at the $NH_2$-terminus of S1P. The resulting 1094-amino acid fusion protein consists of an initiator methionine, amino acids 2–23 of hamster S1P (the putative signal sequence), three novel amino acids (GGR, SEQ ID NO:12) encoded by the sequence of the NotI restriction site, three tandem copies of the 9E10 epitope derived from the human c-Myc protein (S EQKLISEEDLNGEQKLISEEDLNG EQKILISEEDLNSSG) (SEQ ID NO:5), and amino acids 24–1052 of hamster S1P. pCMV-Myc-S1P was constructed as follows. First, pCMV-S1P (described above) was digested with SalI and NotI, and the resulting 4.2-kb insert containing hamster S1P was subsequently cloned into the EcoRV-NotI sites of pcDNA3. To destroy the NotI restriction site, this plasmid was digested with NotI, filled in with Klenow fragment, and religated, generating intermediate construct-1. Second, intermediate construct-1 was subjected to in vitro site-directed mutagenesis (Kunkel et al., 1987; Hua et al., 1996b) to introduce a NotI restriction site at the position that corresponds to amino acid 23 of hamster S1P (which is the COOH-terminal amino acid of the putative signal sequence of S1P), generating intermediate construct-2. Third, a 120-bp fragment flanked by NotI sites encoding three tandem copies of the c-Myc epitope tag (described above, obtained from Dr. C. Kaiser, Massachusetts Institute of Technology) was inserted into the NotI site of intermediate construct-2, yielding a construct expressing epitope-tagged hamster S1P, designated pCMV-Myc-S1P. Point mutations in the S1P coding region of this plasmid were constructed by site-directed mutagenesis as described above. The final structures of all plasmids were confirmed by sequencing all ligation junctions.

RESULTS

Figure 5A:
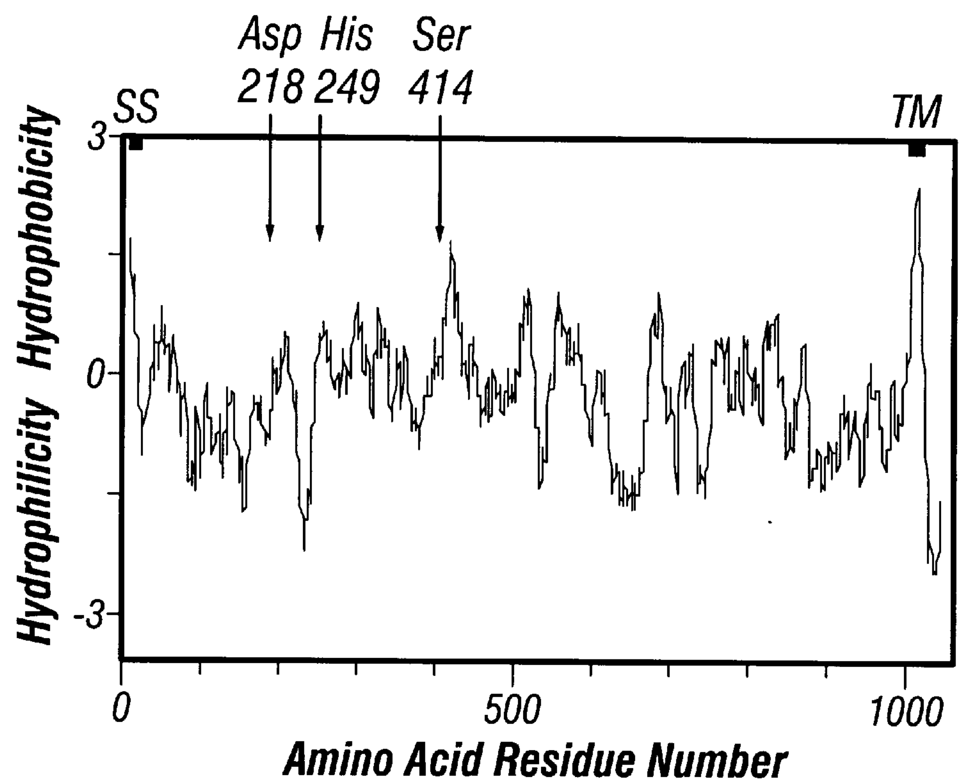
FIG. 5A. The residue-specific hydropathy index was calculated over a window of 20 residues by the method of Kyte and Doolittle (1982), using the Genetics Computer Group Sequence Analysis Software Package, Version 8.1 (Devereux et al., 1984). Arrows denote the three amino acids that correspond to the catalytic triad for subtilisin-like serine proteases. SS, signal sequence; TM, transmembrane region.
Figure 5B:
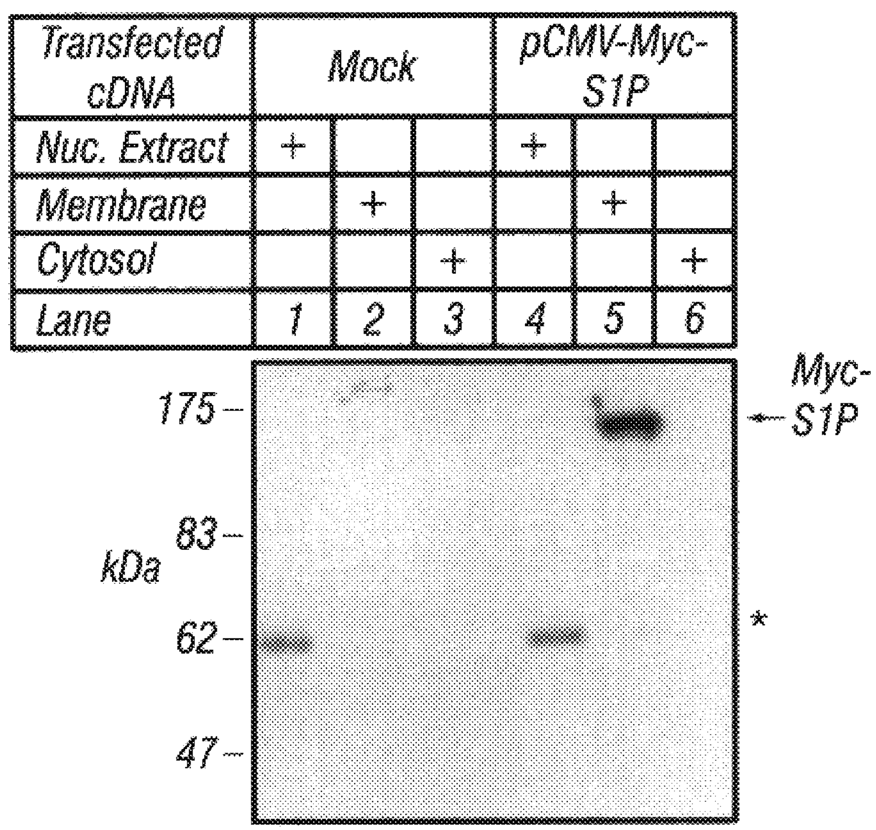
FIG. 5B. 293 cells were transfected with 1 μg/dish of either pcDNA 3 empty vector (lanes 1–3) or pCMV-Myc-S 1P (lanes 4–6) as described in Experimental Procedures. The total amount of transfected DNA was adjusted to 5 μo/dish by addition of pcDNA 3 empty vector. Transfected cells were incubated in medium C supplemented with 10% fetal calf serum for 16 h and fractionated into nuclear extract, membrane, and cytosol fractions as described (Sakai et al., 1996). Aliquots of protein from transfected cells (40 μg, lanes 1 and 4; 60 μg, lanes 2, 3, 5, and 6) were subjected to SDS-PAGE and immunoblot analysis with 2 μg/ml of monoclonal anti-c-Myc (clone 9E10) as described in Experimental Procedures. The filter was exposed to film for 2 s. The asterisk (*) denotes the endogenous c-Myc protein.
Figure 5C:
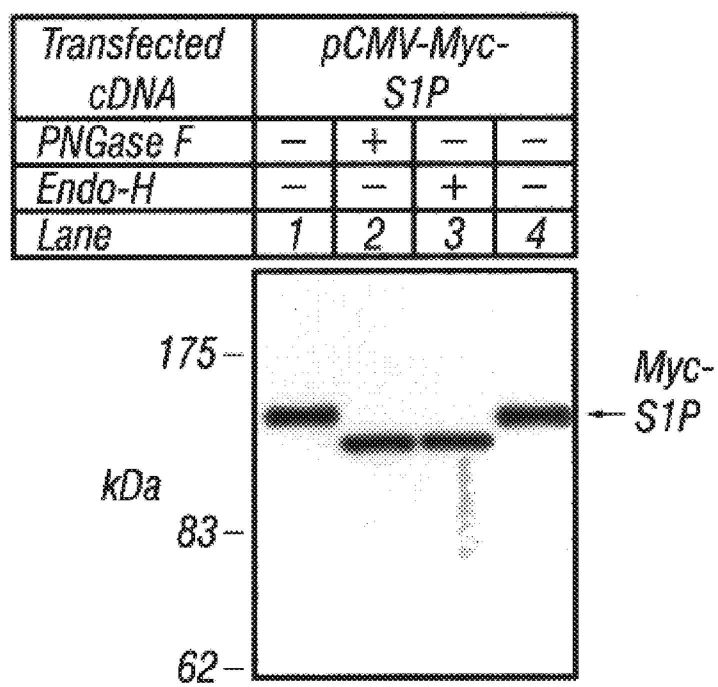
FIG. 5C. Aliquots of the $10^5$ g membrane fraction from 293 cells transfected with pCMV-Myc-S1P, prepared as in (B), were treated with the following glycosidases: lane 1, none; lane 2, 0.063 IU/ml peptide N-glycosidase F (PNGaseF); lane 3, 0.9 IU/ml endoglycosidase $H_f$; lane 4, none. Enzymatic digestion was performed as described by Sakai et al. (1998a). Aliquots of treated membrane fractions (5 μg protein) were subjected to SDS-PAGE and immunoblotted with 2.5 μg/ml of monoclonal anti-c-Myc (clone 9E10). The filter was exposed to film for 1 s.

FIG. 5A shows a hydropathy plot of S1P, which indicates that the protein is generally hydrophilic with the exception of the signal sequence at the $NH_2$-terminus and the apparent transmembrane segment near the COOH-terminus. To determine whether the protein is membrane-bound, the inventors prepared an expression vector encoding S1P with three copies of a c-Myc tag inserted immediately following the signal sequence (denoted by the arrow in FIG. 4). The c-Myc tag is expected to remain associated with S1P following cleavage by signal peptidase. This cDNA was transfected into 293 cells and fractionated the cells into a nuclear extract, a membrane fraction, and cytosol, all of which were subjected to SDS polyacrylamide gel electrophoresis. All of the immunodetectable S1P was found in the membrane fraction (FIG. 5B, lane 5). The antibody also reacted with a protein of 62 kDa that was present in the nuclear extract of the mock-transfected cells. The inventors believe that this is the endogenous c-Myc protein of these cells. FIG. 5C shows that S1P is sensitive to treatment with endoglycosidase H, confirming that the protein contains N-linked sugars and is located in the lumen of the ER (Kornfeld and Kornfeld, 1985).

Example 4

Characterization of S1P Genomic Structure and Transcriptional Activity

MATERIALS AND METHODS

Blot Hybridization of Genomic DNA

Genomic DNA (10 $\mu$g) was isolated from CHO/pS2P, SRD-2A, and SRD-12B cells using the DNA Extraction Kit (Stratagene). The DNA was digested with the indicated restriction enzymes, subjected to electrophoresis in a 0.7% agarose gel, and transferred to Hybond $N^+$ filters (Amersham) by capillary blotting. After transfer, the filters were crosslinked at 120 mJ in a Stratalinker (Stratagene). Filters were then prehybridized with Rapid-hyb buffer (Amersham) at 65° C. for 1 h and blotted with $^{32}$P-labeled probes overnight at 65° C. Probes 1 and 2 (see below) were generated by PCR™ using pCMV-S1P as a template. Probe 1 (2.1 kb). corresponding to the 5' end of the S1P cDNA, was amplified by PCR using the 5' primer, 5'-GTGGTGCAAATGGAGTCTAGG-3', (SEQ ID NO:6) and the 3' primer, 5'-CACAGAAATGGAGATGGCCAG-3' (SEQ ID NO:7); Probe 2 (2.1 kb) corresponding to the 3' end of the S1P cDNA, was amplified using the 5' primer, 5'-ACCAAGAAGGCAGCTTCCTGG-3' (SEQ ID NO:8) and the 3' primer, 5'-TTCCCAGATCTGTGCACATGC-3' (SEQ ID NO:9); Probe 3 (3.0 kb), corresponding to the entire cDNA of hamster ACAT, was isolated from the vector pRC-CMV7SB by digestion with SalI and NotI (Cao et al., 1996). Probes were gel-purified and then labeled with [$\alpha^{32}$P] dCTP by random priming using the Megaprime DNA Labeling System. Hybridized filters were washed at room temperature for 30 min with 2×SSC and 0.1% SDS, followed by a 1 h incubation in 0.1×SSC and 0.1% SDS at 65° C. Washed filters were exposed to Kodak X-Omat Blue XB-1 film at −80° C. with intensifying screens and developed using an automated processor.

RESULTS

Figure 6A:
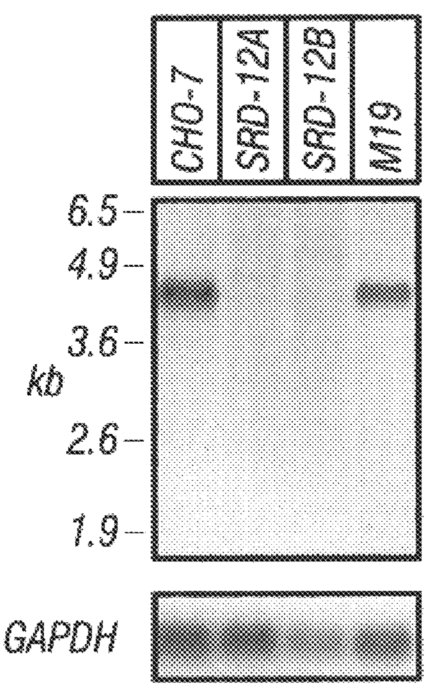
FIG. 6A. On day 0, the indicated hamster cell line was set up at a density of $5\times10^5$ cells/100-mm dish in medium B and were refed the same medium on day 2. On day 3, total RNA was prepared, and poly(A)$^+$ RNA was purified. A $^{32}$P-labeled 4.2-kb SalI/NotI fragment derived from hamster S1P cDNA ($1.6\times10^6$ cpm/ml) was hybridized to 3 $\mu$g of poly(A)$^+$ RNA from the indicated cells for 3 h at 65° C. in Rapid-hyb buffer (Amersham), washed twice with 2×SSC and 0.1% SDS at room temperature for 30 min each, followed by two washes with 0.1×SSC and 0.1% SDS at 70° C. for 30 min each. The nylon membrane was exposed to Kodak X-Omat Blue XB-1 film with an intensifying screen at −80° C. for 10 h. The same membrane was subsequently hybridized with a 1.1-kb rat glyceraldehyde-3-phosphate dehydrogenase (GAPDH) probe ($1\times10^6$ cpm/ml) (Chen et al., 1991 ) and exposed to film for 2 h at −80° C. with an intensifying screen.
Figure 6B:
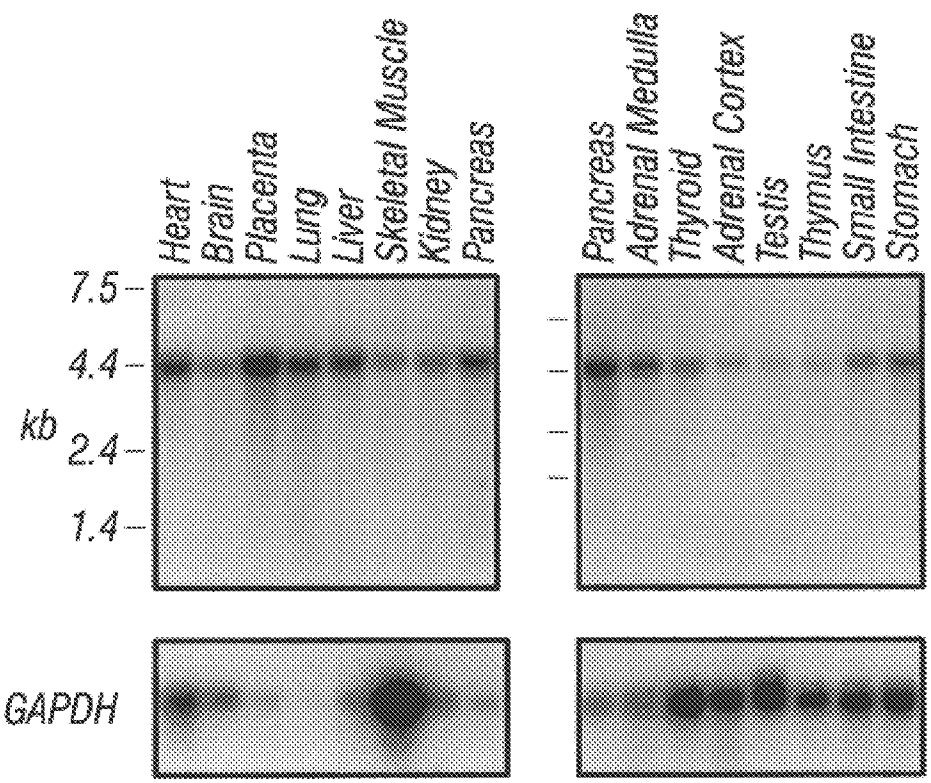
FIG. 6B. The hamster $^{32}$P-labeled S1P probe ($1.6\times10^6$ cpm/ml) (same probe used in Panel A) was hybridized for 1 h at 68° C. to a nylon membrane containing poly(A)$^+$RNA from the indicated human tissue (2 $\mu$g/lane) (Multiple Tissue Northern Blots, Clontech) in the ExpressHyb Hybridization solution (Clontech), washed twice with 2×SSC and 0.1% SDS at room temperature for 30 min each, followed by two washes with 0.3×SSC and 0.1% SDS at 50° C. for 30 min each. The membrane was exposed to film with an intensifying screen at −80° C. for 10 h. The same membrane was subsequently hybridized with rat GAPDH probe ($1\times10^6$ cpm/ml), washed with 0.3×SSC and 0.1% SDS at 50° C. for 30 min, and exposed to film for 2 h at −80° C. with an intensifying screen.

To determine whether the SRD-12B cells produce an mRNA encoding S1P, the inventors performed a northern blot analysis (FIG. 6A). The S1P probe hybridized to a single mRNA of 4.4 kb in wild-type CHO-7 cells. This mRNA was also present in the mutant M19 cells, which lack S2P. The mRNA was not detectable in either the SRD-12A or SRD-12B cells. FIG. 6B shows the distribution of the S1P mRNA in multiple human tissues. The mRNA was detected in all tissues that were studied.

Figure 7:
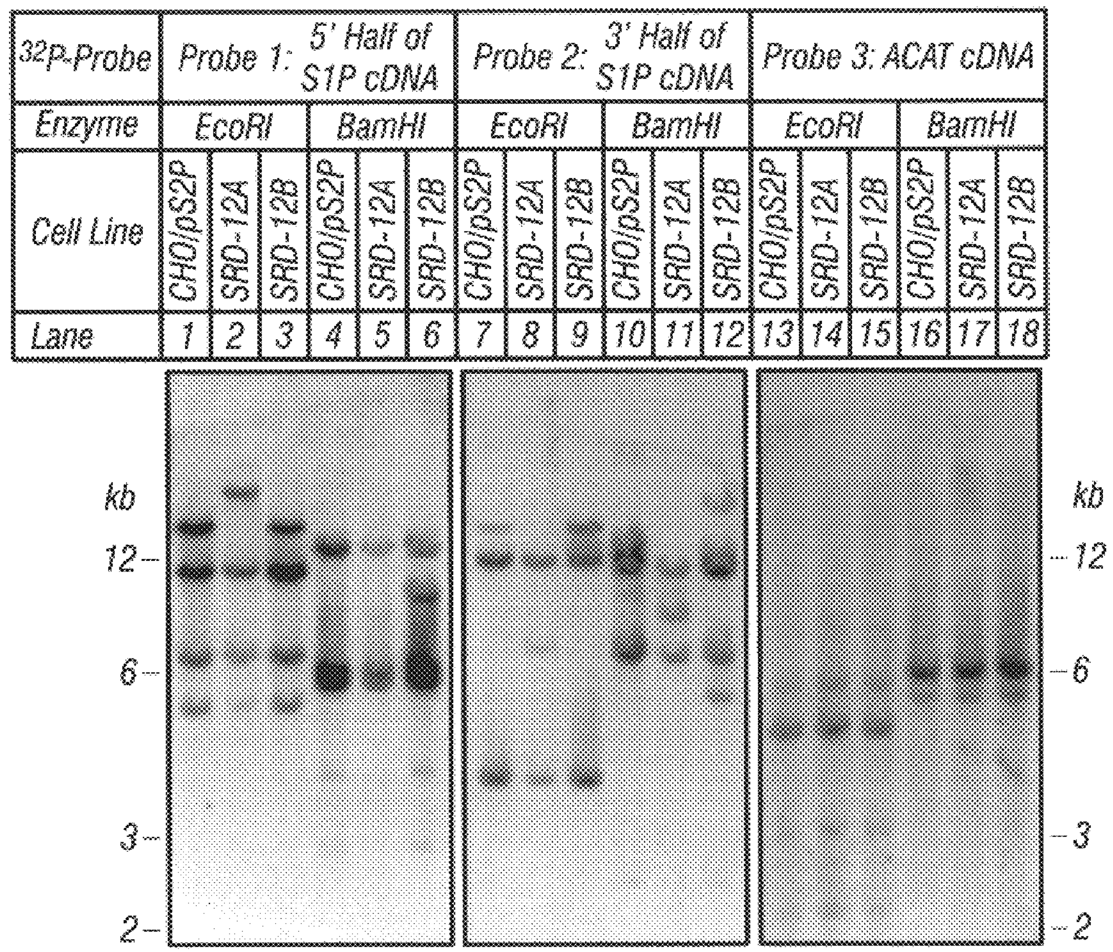
FIG. 7. Genomic Southern Blot Analysis of the S1P Gene in Wild-type and Mutant Cell Lines. Aliquots of genomic DNA (10 $\mu$g/lane) from the indicated cell line were digested with the indicated restriction enzyme, subjected to electrophoresis on 0.7% agarose gels transferred to filters, and hybridized with the indicated $^{32}$P-labeled probe ($2\times10^6$ cpm/ml) as described in Experimental Procedures. The filter in lanes 1–6 was boiled in 0.5% SDS and rehybridized with a probe for the hamster ACAT cDNA (lanes 13–18). Filters were exposed to film with an intensifying screen at −80° C. for 17 h.

FIG. 7 shows a series of Southern blots performed with genomic DNA from the parental CHO/pS2P cells and the two S1P-deficient mutant cell lines. The DNA was digested with either of two restriction enzymes and probed with radiolabeled probes corresponding to the 5' half of the S1P cDNA or the 3' half. The EcoRI digest of the SRD-12A DNA revealed shifted bands when analyzed with the 5' probe (lane 2) and the 3' probe (lane 8). In addition, the intensity of all of the bands was reduced by 50% when compared with the DNA from the other cell lines as revealed by densitometric scanning. This finding was taken to indicate that the SRD-12A cells have a deletion of one copy of the S1P gene and a rearrangement of the second copy. The DNA from the SRD-12B cells showed abnormalities in the BamHI digest (lanes 6 and 12). The intensities of the other bands were similar to those in wild-type cells. It was concluded that the SRD-12B cells have undergone a rearrangement in at least one copy of the S1P gene. The other copy may be rearranged, or it may have a more subtle mutation that abolishes the production of mRNA.

Example 5

Biochemical Characterization of intracellular S1P Enzymatic Activity

MATERIALS AND METHODS

Immunoblot Analysis of SREBP Processing in SRD-12B Cells Transfected with pCMV-S1P and pCMV-Myc-S1P On day 0, SRD-12B cells were set up at a density of $6\times10^5$ cells/60-mm dish in medium B. On day 1, cells were transfected with 4 $\mu$g of the indicated plasmid DNA plus 12 $\mu$l of LipofectAMINE™ reagent (Life Technologies) according to the manufacturer's instructions with modifications as follows. LipofectAMINE™/DNA complexes were formed in 1 ml of serum-free medium for 15 min at room temperature, and 0.5 ml were added to 1 ml of serum-free medium per dish. After incubation for 3 h at 37° C. in a 8%–9% CO, incubator, the medium was removed, and the cells were cultured in the medium A supplemented with 5% fetal calf lipoprotein-deficient serum, 50 $\mu$M compactin. and 50 $\mu$M sodium mevalonate in the absence (–) or presence (+) of sterols (1 $\mu$g/ml of 25-hydroxycholesterol plus 10 $\mu$g/ml of cholesterol added in a final concentration of 0.2% ethanol). After incubation at 37 ° C. for 20 h, the cells received N-acetyl-leucinal-leucinal norleucinal (ALLN) at a final concentration of 25 $\mu$g/ml. After incubation for 1 h. the cells were harvested and fractionated into nuclear extracts and $10^5$ g membrane pellets as previously described (Sakai et al., 1996). Samples from the nuclear extract and membrane fractions were mixed in a ratio of 5:1 with 5×SDS loading buffer (IX loading buffer contains 30 mM Tris-HCl at pH 7.4, 3% SDS, 5% (v/v) glycerol, 0.004% bromphenol blue, and 2.5% β-mercaptoethanol). After boiling for 5 min, the proteins were subjected to SDS-PAGE and transferred to Hybond-C Extra nitrocellulose filters (Amersham). The filters were incubated with the antibodies described in the figure legends. Bound antibodies were visualized with peroxidase-conjugated affinity-purified donkey anti-mouse IgG using the SuperSignal CL-HRP substrate system (Pierce) according to the manufacturer's instructions except that nitrocellulose filters were blocked by incubation for 60 min at room temperature with PBS containing 0.05% (v/v) Tween 20, 5% (v/v) nonfat dry milk, and 5% newborn calf serum. Gels were calibrated with prestained molecular weight markers (New England Biolabs, Beverly, Mass.). Filters were exposed to X-Omat Blue XB-1 film (Kodak, Rochester, N.Y.) with intensifying screens at room temperature for the indicated time.

RESULTS

Figure 8:
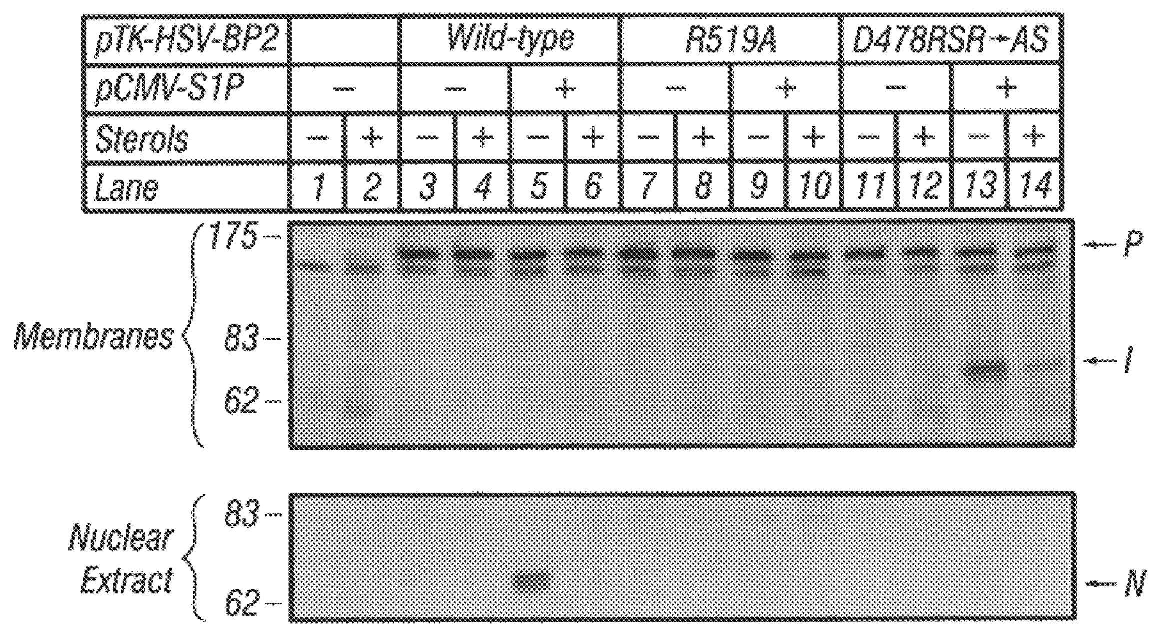
FIG. 8. Site-1 Protease cDNA Restores Regulated Cleavage of Epitope-Tagged SREBP-2 in Transfected SRD-12B Cells. SRD-12B cells were set up for experiments on day 0 and transfected on day 1 as described in Experimental Procedures. The indicated plasmid encoding wild-type or mutant HSV-tagged SREBP-2 (3.5 $\mu$g/dish, lanes 3–14) was cotransfected into SRD-12B cells with or without pCMV-S1P (0.5 $\mu$g/dish) as indicated. The total amount of DNA was adjusted to 4 $\mu$g/dish by addition of either pTK empty vector (Hua et al., 1995) or PcDNA 3 empty vector. Transfected cells were incubated in either the absence (−) or presence (+) of sterols, and the cells were harvested and fractionated as described in Experimental Procedures. Aliquots of the nuclear extract (30 $\mu$g protein) and membrane (60 $\mu$g) fractions were subjected to SDS-PAGE and immunoblotted with 0.5 $\mu$g/ml of mouse IgG-HSV-Tag™ as the first antibody and 0.16 $\mu$g/ml of donkey anti-mouse IgG as the second antibody. Filters were exposed to film for 20 s (nuclear extracts), or 5 s (membranes). P, I, and N denote the precursor, intermediate, and nuclear forms of HSV-tagged SREBP-2, respectively.

To demonstrate directly that S1P restores cleavage of SREBPs in SRD-12B cells, cells were transfected with pCMV-S1P, a vector in which the expression of S1P is driven by the CMV promoter (FIG. 8). As a reporter, pTK-HSV-BP2 was used, which produces an HSV-tagged version of SREBP-2 under control of the thymidine kinase promoter, which gives a near-physiologic level of expression (Hua et al., 1996b). Cell membranes and nuclear extracts were subjected to electrophoresis and blotted with an antibody against the HSV epitope-tag. In the absence of transfected S1P, the SRD-12B cells failed to cleave HSV-BP2, as indicated by the lack of a band in the nuclear extract (lane 3). Cotransfection of pCMV-S1P led to the appearance of the nuclear form (lane 5), which disappeared when sterols were added (lane 6). pCMV-S1P did not produce a nuclear band when it was transfected together with a cDNA encoding a mutant version of HSV-BP2 that contains the R519A substitution that blocks Site-1 proteolysis (lane 7). A cDNA was also transfected encoding a mutant version of HSV-BP2 which has the D478RSR→AS substitution that blocks cleavage by S2P. When this was transfected into the SRD-12B cells, no intermediate form was observed in the membranes, and no nuclear form (lane 11), a finding that is consistent with the absence of Site-1 cleavage. When S1P was cotransfected together with the D478RSR→AS mutant, a new band was noted corresponding to the intermediate form in the membrane fraction (lane 13). The amount of this band was reduced in the presence of sterols. confirming that it was the product of Site-1 cleavage (lane 14) (Sakai et al., 1996).

Figure 9A:
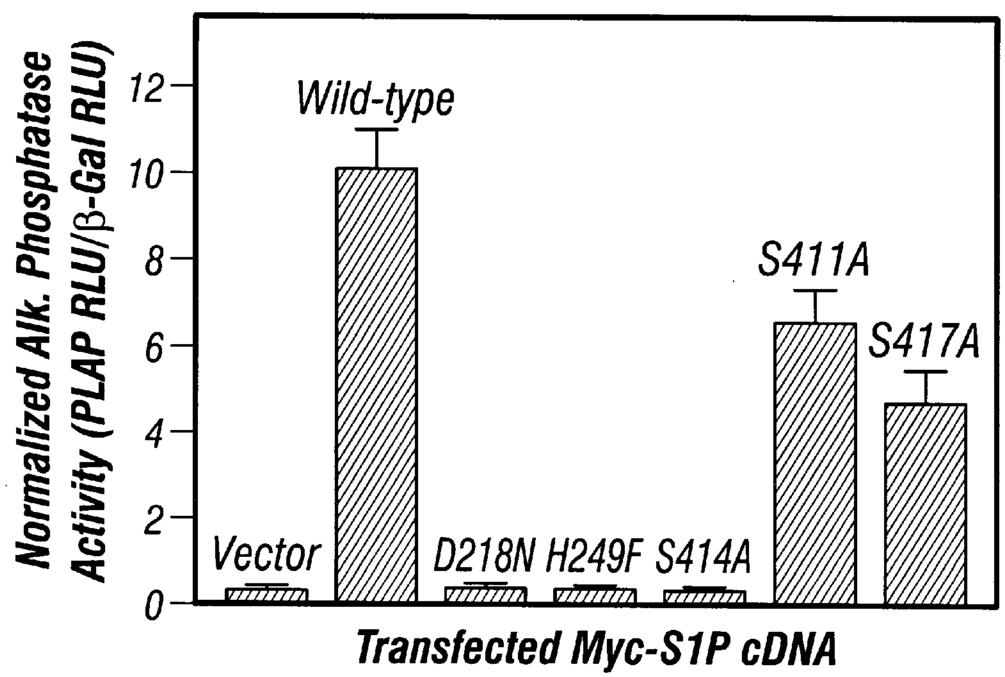
FIG. 9A. Secretion of alkaline phosphatase. SRD-12B cells ($4\times10^4$ cells/22-mm well) were transfected with an expression plasmid containing no cDNA insert or the indicated c-Myc tagged S1P cDNA (0.03 $\mu$g/well) together with pCMV-PLAP-BP2 (513–1141) (0.1 $\mu$g/well), pCMV-SCAP (0.56 $\mu$g/well), and pCMVβ-gal (0.01 $\mu$g/well) as described in Experimental Procedures. After transfection, the cells were cultured in medium A supplemented with fetal calf lipoprotein-deficient After incubation for 16 h, the medium was collected, and placental alkaline phosphatase was measured and normalized to cellular β-galactosidase activity as described in Experimental Procedures. Each value is the average of duplicate transfections (range of values denoted by error bars).
Figures 1, 9B:
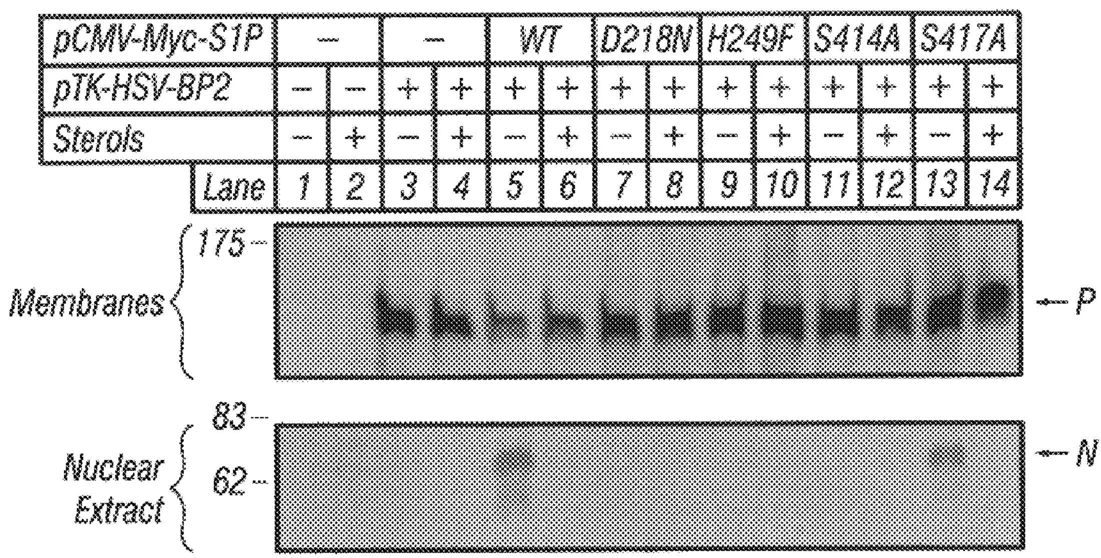
FIG. 9B. Immunoblot analysis of epitope-tagged SREBP-2. SRD-12B cells were set up on day 0 and transfected on day 1 as described in Experimental Procedures. Plasmid pCMV-Myc-S1P encoding the indicated wild-type or mutant Myc-tagged S1P (0.5 $\mu$g/dish) was cotransfected with pTK-HSV-BP2 (3 $\mu$g/dish). The total amount of DNA was adjusted to 3.5 $\mu$g/dish as described in FIG. 8. Transfected cells were incubated for 21 h in either the absence (−) or presence (+) of sterols as indicated and then harvested and fractionated as described in Experimental Procedures. Aliquots of nuclear extract (30 $\mu$g protein) or membranes (60 $\mu$g) were subjected to SDS-PAGE and immunoblotted with 0.5 $\mu$g/ml of IgG-HSV-Tag™ or 2 $\mu$g/ml of monoclonal anti-c-Myc (clone 9E10) as described in Experimental Procedures. Filters were exposed to film for 1 min (top panel), 20 s (middle panel), or 4 s (bottom panel). P and N denote the precursor and nuclear forms of HSV-tagged SREBP-2, respectively.

To determine whether the proposed catalytic triad is essential for S1P activity, versions of pCMV-Myc-S1P were prepared in which the codons for Asp218, His249, and Ser414 were individually mutated to encode different amino acids (D218N, H249F, and S414A). As controls, two nearby serines were mutated that are not proposed to be part of the catalytic triad (8411A and S417A). Each plasmid was transfected into SRD-12B cells together with pCMV-PLAP-BP2 (513–1141), pCMV-SCAP, and pCMVβ-gal (FIG. 9A). Whereas the cDNA encoding wild-type S1P increased PLAP activity in the culture medium, each of the catalytic triad mutants failed. The control substitutions (5411A and 8417A) had activities that were 50–70% of wild-type levels In a more direct test for S1P catalytic activity, the mutant plasmids were transfected into the SRD-12B cells together with pTK-HSV-BP2. Membranes and nuclear extracts were subjected to SDS-PAGE and blotted with an antibody against the HSV-tagged SREBP-2 (FIG. 9B). Wild-type S1P restored cleavage of SREBP-2, and a band of the appropriate size was detected in the nuclear extract (FIG. 9B, lane 5). This band disappeared when the cells were treated with sterols (lane 6). The three catalytic triad mutants did not produce nuclear SREBP-2 either in the absence or presence of sterols (lanes 7–12). In contrast, the control S417A mutant had sterol-regulated activity that was similar to wild-type (lanes 13 and 14). The membrane fractions were also subjected to immunoblotting, which revealed that all of the transfected cells produced equivalent amounts of the precursor form of HSV-BP2 and Myc-S1P (FIG. 9B).

Figure 10:
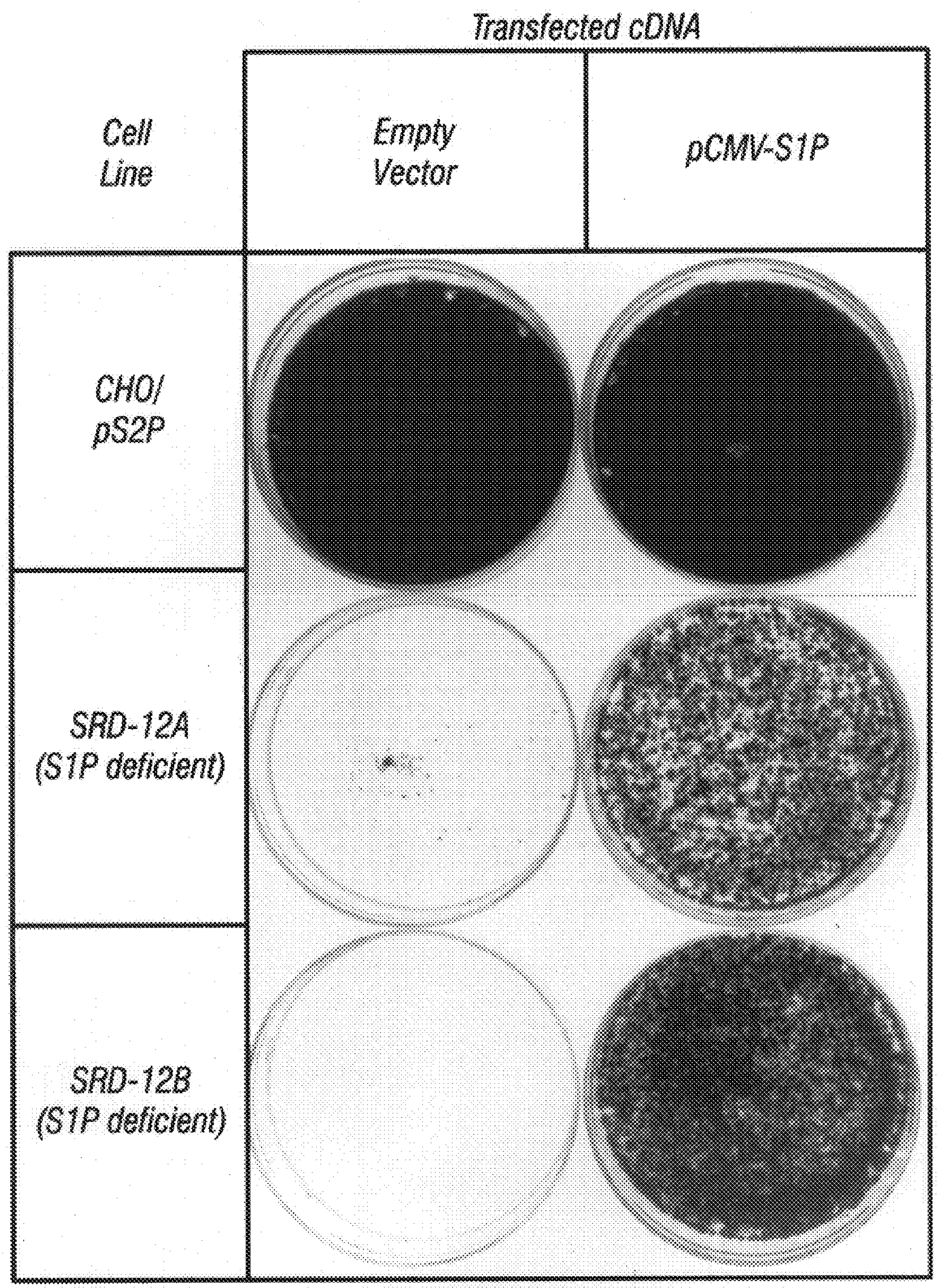
FIG. 10. S1P cDNA Restores Growth of SRD-12A and SRD-12B Cells in Absence of Cholesterol. On day 0, cells were set up at $3.5\times10^5$ cells/60-mm dish in medium B. On day 1, the cells were transfected with 5 $\mu$g/dish of either pcDNA 3.1 empty vector or pCMV-S1P using the MBS Transfection Kit as previously described (Rawson et al., 1997). On day 2, cells were washed with PBS and refed medium A supplemented with 5% (v/v) fetal calf lipoprotein-deficient serum. Cells were refed every 2 days thereafter. On day 15, cells were washed with PBS, fixed in 95% ethanol, and stained with crystal violet.

FIG. 10 shows a growth study that tested the ability of different cell lines to grow in the absence of cholesterol, either with or without transfection of pCMV-S1P. The parental CHO/pS2P cells grew in the absence of cholesterol, and there was no change when they were transfected with the cDNA encoding pCMV-S1P. On the other hand, the SRD-12A and SRD-12B cells failed to grow in the absence of cholesterol. Growth was restored when these cells were permanently transfected with pCMV-S1P. This result formally demonstrates that restoration of S1P-activity can restore growth of the mutant cells in the absence of cholesterol.

DISCUSSION

Figures 2, 9B:
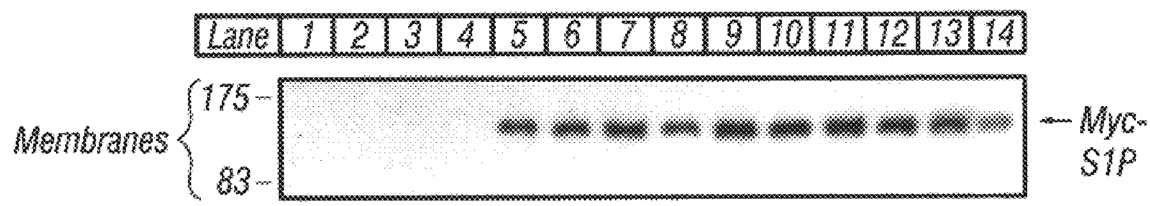
FIGS. 2(A–C). SCAP-Stimulated Secretion of Alkaline Phosphatase in Cells Transfected with pCMV-PLAP-BP2 (513–1141). After incubation for 16 h, aliquots of medium were removed and assayed for placental alkaline phosphatase activity. The data were normalized to cellular β-galactosidase activity as described in Experimental Procedures. Each value is the average of duplicate transfections.

The current results add a central piece of information in the understanding of sterol-regulated processing of SREBPs. The data reveal that Site-1 cleavage is catalyzed by a novel membrane-bound glycoprotein that belongs to the subtilisin superfamily of serine proteases which are sometimes referred to as subtilases (Siezen and Leunissen, 1997). The following three lines of evidence indicate that the cloned S1P is the enzyme that normally cleaves SREBPs at Site-1: First, rearrangements in the S1P gene that abolish S1P mRNA expression are found in SRD-12A and SRD-12B cells, which are auxotrophic for cholesterol owing to a failure to cleave SREBPs at Site-1 (FIG. 6 and FIG. 7). Second, expression of S1P restores Site-1 cleavage of SREBP-1 and SREBP-2 in SRD-12B cells (FIG. 8 and FIG. 9 for SREBP-2), and this is associated with a restoration of cholesterol-independent growth (FIG. 10). Third, substitutions in any one of the three residues that form the postulated catalytic triad of S1P abolish its ability to restore Site-1 cleavage (FIG. 9).

In cloning the cDNA for S1P, the inventors employed a novel strategy that took advantage of a mutant cell line with a deficiency of S1P activity and utilized a novel assay system. The inventors also exploited the ability of S1P to cleave its substrate in the lumen of the ER, thereby allowing the design of a fusion protein whose secretion is dependent on Site-1 cleavage. The development of this assay represents an important part of the invention as it allows the efficient screening of candidate modulators of S1P, which potentially have great therapeutic value in the treatment of conditions associates with elevated serum cholesterol levels.

The inventors chose PLAP as a reporter for these studies because it normally functions in the extracellular environment and because a sensitive chemiluminescence assay is available. Any other reporter protein could potentially be used, however. Indeed, the inventors employed bovine prolactin in a similar fusion construct with SREBP-2, and its secretion was also shown to be dependent on S1P. These fusion proteins provide a convenient way in which to monitor the activity of S1P without having to disrupt the cells. These reporters should be useful for studies of S1P regulation in cell culture and also in the bodies of living animals.

Studies of the cleavage of PLAP-BP2 provide information about the general properties of the Site-1 cleavage reaction. Secretion of PLAP requires two cleavages. The first occurs at the normal site of cleavage by signal peptidase, and the second occurs at Site-1 (FIG. 1). Cleavage by signal peptidase normally occurs cotranslationally (Blobel, 1980), and it is therefore highly likely that this cleavage precedes cleavage at Site-1. Thus, S1P is able to cleave a protein that has a free $NH_2$-terminus in the lumen of the ER: it does not require that the $NH_2$-terminus be anchored to the membrane, as it is in native SREBP.

The conserved sequence motifs surrounding the catalytic triad allow S1P to be classified unambiguously as a member of the subtilisin superfamily (Siezen and Leunissen, 1997). Outside of the catalytic domain, the sequence of S1P bears little relation to the other members of this superfamily. From a functional viewpoint, the action of S1P most resembles that of the furins, which are subtilases of the Kex2p-like subfamily that process proteins such as the insulin proreceptor and pro-endothelin-1 prior to secretion in animal cells (Nakayama, 1997). S1P differs substantially from the furins in two respects: 1) substrate recognition—furins always cleave after dibasic sequences. most often with the consensus sequence RX(K/R)R. S1P cleaves after RSVL (SEQ ID NO:11). (Duncan et al, 1997); and 2) cellular location—furins act in post-Golgi secretory vesicles, whereas S1P acts in a pre-Golgi compartment, most likely the ER. All members of the Kex2p-like family and most other subtilases are synthesized as pre-proteins that must be cleaved proteolytically in order to be active. Cleavage removes an $NH_2$-terminal prepro-peptide that inhibits activity. It is not yet clear if S1P contains a prepro-peptide.

The deduced amino acid sequence of S1P and its sensitivity to endoglycosidase H suggests that S1P topologically is a Type I integral membrane protein with a large protease domain of ~1020 amino acids that resides in the lumen of the ER, followed by a single membrane-spanning domain and a short cytoplasmic COOH-terminal tail. If S1P does function in the ER, its activity must be tightly regulated so as to prevent it from degrading nascent polypeptides nonspecifically. This is presumably the function of SCAP, which directs S1P to SREBPs (Sakai et al., 1998a).

The function of the unusual COOH-terminal cytoplasmic domain of S1P is not yet clear. This 30-residue sequence has a highly unusual composition that is rich in basic residues and prolines. Its sequence is suggestive of a β-sheet that has a high density of positive charges on one surface. This cytoplasmic tail might function in determining the subcellular localization of S1P. It might also play a role in the interaction with the WD-repeat domain of SCAP, which is required for S1P activity (Sakai et al., 1998a). Further studies may clarify the mechanism by which SCAP activates S1P and renders it sensitive to inhibitions by sterols.

Example 6

Construction of S1P Fusion Proteins and S1P Site-Directed Mutants

MATERIALS AND METHODS

The inventors obtained monoclonal antibodies IgG-HSV-Tag™ from Novagen (Madison. Wis.), anti-c-Myc (clone 9E10) from Boehringer Mannheim (Indianapolis, Ind.) or Invitrogen (Carlsbad, Calif.); anti-c-Myc agarose-conjugated beads from Santa Cruz Biotechnology, Inc. (Santa Cruz, Calif.); anti-BiP from StressGene Biotechnologies Corp. (Victoria, British Columbia); horseradish peroxidase-conjugated donkey anti-rabbit whole antibody from Amersham (Arlington Heights, Ill.); horseradish peroxidase-conjugated, donkey anti-mouse IgG (affinity-purified) from Jackson Immunoresearch Laboratories (West Grove, Pa.); maleimide-activated keyhole limpet hemocyanin from Pierce (Rockford, Ill.); and glycosidases from New England Biolabs (Beverly, Mass.). Other reagents were obtained from sources as described previously (Sakai et al., 1998b; Wang et al., 1994; Nohturfft et al., 1998b;). Newborn and fetal calf lipoprotein-deficient serum (d>1.215 g/ml) were prepared as described (Goldstein et al., 1983).

Construction of Plasmids

The following plasmids contain the cytomegalovirus (CMV) promoter-enhancer driving expression of various cDNAs. pCMV-SCAP(D443N) is a previously described plasmid that encodes hamster SCAP with a D443N mutation that renders the protein resistant to sterols (Hua et al., 1996a). Other previously described plasmids (Sukai et al., 1998b) include pCMV-S1P, which encodes hamster S1P; pCMV-Myc-S1P, which encodes hamster S1P containing three tandem copies of the c-Myc epitope tag inserted between amino acids 23 and 24 of SEQ ID NO:1; and pCMV-Myc-S1P(S414A), which is identical to pCMV-Myc-S1P except that serine-414 of SEQ ID NO:1 has been changed to alanine. pCMV-Myc-S1P(Site-B mutant) is identical to pCMV-Myc-S1P except that amino acids 134–137 of S1P (SEQ ID NO:1) have been mutated from RSLK (SEQ ID NO:18) to AAAA (SEQ ID NO:21). pCMV-Myc-S1P (Site-C mutant) is identical to pCMV-Myc-S1P except that amino acids 163–164 (RR) and 183–187 (RRLLR (SEQ ID NO:22)) of SEQ ID NO:1 have been mutated to VA and AAAAA (SEQ ID NO:23), respectively. To generate pCMV-Myc-S1P(Site-B mutant) and pCMV-Myc-S1P(Site-C mutant), the inventors used the QuikChange Site-Directed Mutagenesis kit (Stratagene) to mutagenize a 2.6-kb HindIII fragment of pCMV-Myc-S1P subcloned into pBluescript KS- (Stratagene). Oligonucleotides corresponding to the following sequences were used to create pCMV-Myc-S1P (Site-B mutant) and pCMV-Myc-S1P(Site-C mutant): CCTCAACGCAAAGTCTTTGCCGCGGCTGCTTTTGCTGAATCTGACCC (SEQ ID NO:24) for the Site-B mutant; and GGCAGTCATCACGACCCCTGGTTGCCGCTAGCCTCTCCCTGGGC (SEQ ID NO:25) and AGGAAGACATTCAAGCGCCGCGGCTGCTGCTGCCATTCCTCGACAGG (SEQ ID NO:26) for the Site-C mutant. Following mutagenesis, the mutated 1.5-kb BstEII-HpaI fragment was ligated to an 8.3-kb BstEII-HpaI fragment of pCMV-Myc-S1P to yield the final plasmid. pCMV-Myc-S1P (Site-B+C mutant) contains both the Site-B and Site-C mutations and was constructed by sequential mutagenesis.

pCMV-S1P-Myc encodes full length hamster S1P (amino acids 1–1052, SEQ ID NO:1) containing three tandem copies of the c-Myc epitope at the COOH-terminus followed by six histidine residues. Construction of this expression vector is described in a later example where it is referred to as pCMV-S1P(1052)Myc-His. pCMV-S1P-Myc(S414A) is identical to pCMV-S1P-Myc except that serine-414 has been changed to alanine. To generate pCMV-S1P-Myc(S414A), a 0.4-kb EcoRI fragment of pCMV-S1P was ligated to a 9.3-kb EcoRI fragment of pCMV-Myc-S1P(S414A) to create pCMV-S1P(S414A). Then, a 1.4-kb BstEII-HpaI fragment of pCMV-S1P(S414A) was ligated to a 8.3-kb BstEII-HpaI fragment of pCMV-S1P-Myc to create pCMV-S1P-Myc(S414A).

The following plasmids contain the thymidine kinase (TK) promoter from Herpes Simplex virus driving expression of the indicated cDNA. pTK-Myc-S1P encodes Myc-S1P and was constructed by ligating a 4.0-kb BamHI (blunted by Klenow)-XbaI fragment of pCMV-Myc-S1P to a 5.8-kb SpeI (blunted by Klenow)-XbaI fragment from pTK-HSV-BP2 (see below). pTK-Myc-S1P(Site-B mutant) is identical to pTK-Myc-S1P except that amino acids 134–137 of SEQ ID NO:1 have been mutated from RSLK (SEQ ID NO:18) to AAAA (SEQ ID NO:21). pTK-Myc-S1P (Site-C mutant) is identical to pTK-Myc-S1P except that amino acids 163–164 (RR) and 183–187 (RRLLR (SEQ ID NO:22)) of SEQ ID NO:1 have been mutated to VA and AAAAA (SEQ ID NO:23), respectively. pTK-Myc-S1P (Site-B+C mutant) contains both Site-B and Site-C mutations. A 3.1-kb Spel-BspDI fragment from pCMV-Myc-S1P (Site-B mutant), pCMV-Myc-S1P(Site-C mutant), or pCMV-Myc-S1P(Site-B+C mutant) was ligated to a 6.7-kb Spel-BspDI fragment from pTK-Myc-S1P to generate pTK-Myc-S1P(Site-B mutant), pTlK-Myc-S1P(Site-C mutant), and pTK-Myc-S1P(Site-B+C mutant), respectively.

pTK-HSV-BP2 encodes human SREBP-2 with two tandem copies of the HSV epitope at the $NH_2$-terminus and has been described previously (Hua et al., 1996b). pTK-HSV-BP2(RSLK) and pTK-HSV-BP2(RRLL) encode mutant versions of pTK-HSV-BP2 in which the wild-type recognition sequence for S1P in human SREBP-2 (RSVL (SEQ ID NO:11)) has been changed to RSLK (SEQ ID NO:18) and RRLL (SEQ ID NO:19), respectively. These two plasmids were generated by oligonucleotide site-directed mutagenesis using single-stranded. uracil-containin,g DNA as described (Duncan et al., 1997). Mutagenesis was performed on a plasmid containing a 0.8-kb HindIII fragment of human SREBP-2 ligated to a 3.0-kb fragment of pBluescript KS-linearized by digestion with HindIII. Using this plasmid, the inventors mutated amino acids 519–522 of SREBP-2 (RSVL (SEQ ID NO:11)) to either RSLK (SEQ ID NO:18) or RRLL (SEQ ID) NO:19) with the oligonucleotides, AGAACCTGACTCGAATGACTTCAGAGATCTGCCAGAGCCTGAGTGTGG (SEQ ID NO:27) or AGAACCTGACTCGAATGACAGCAGCCGGCGGCCAGAGCCTGAGTGTGG (SEQ ID NO:28). respectively. Subsequently, 0.8-kb HindIII fragments of SREBP-2 containing the mutated sequences were ligated into pTK-HSV-BP2 to generate pTK-HSV-BP2 (RSLK) and pTK-HSV-BP2(RRLL). In all plasmid constructions, mutations were confirmed by sequencing the relevant regions. pVAI encodes the adenovirus-associated I RNA gene, which enhances translation of transfected cDNAs (Akusjarvi et al., 1987).

Cell Culture, Transfection, and Fractionation of Cells

Monolayer cultures of human embryonic kidney 293 cells (l1EK-293 cells) were set up for experiments on day 0 ($4\times10^5$ cells/60-mm dislh) and cultured in 8–9% CO, at 37° C. in medium A (Dulbecco's modified Eagle medium containing 100 units/ml penicillin and 100 $\mu$g/ml streptomycin sulfate) supplemented with 10% (v/v) fetal calf serum. On day 2, the cells were transfected using an MBS kit (Stratagene) with the indicated plasmids as previously described (Hua et al., 1995). Three h after transfection, the cells were refed with 2 ml of medium A supplemented with 1% (v/v) newborn calf lipoprotein-deficient serum, and cultured for 25 h prior to harvest. The medium from two dishes was pooled and centrifuged at 20,000 g at 4° C. for 15 min. An aliquot (2 ml) of the resulting supernatant was mixed with 8 ml of cold acetone and incubated at −20° C. for 15 min. The precipitated proteins were collected at 3,300 g at 4° C. for 15 min and resuspended in 0.1 ml of SDS lysis buffer (10 mM Tris-HCl at pH 6.8, 0.1 M NaCl, 1% SDS, 1 mM EDTA, 1 mM EGTA). The $10^5$ g membrane fraction from cell lysates was prepared as previously described (Sakai et al., 1996).

Monolayers of SRD-12B cells (Rawson et al., 1998) were set up on day 0 ($4\times10^5$ cells/60-mm dish) and cultured in 8–9% CO, at 37° C. in medium B (1:1 mixture of Ham's F12 medium and Dulbecco's modified Eagle medium containing 100 units/ml penicillin and 100 $\mu$g/ml streptomycin sulfate) supplemented with 5% fetal calf serum, 5 $\mu$g/ml cholesterol, 1 mM sodium mevalonate, and 20 M sodium oleate. On day 1, the cells were transfected with the indicated plasmids using LipofectAMINE reagent (Life Technologies) according to the manufacturer's instructions as described (Sakai et al., 1998b). Three h after transfection, the cells were refed with 5 ml of medium B supplemented with 5% fetal calf serum. The cells were incubated for 17 h, after which N-acetyl-leucinal-leucinal-norleucinal was added to each dish at a final concentration of 25 $\mu$g/ml, and the cells were harvested 1 h later. Pooled cells from four 60-mm dishes were used to prepare nuclear extract and $10^5$ g membrane fractions as previously described (Sakai et al., 1996). For experiments in which only membrane fractions were prepared, cells were not incubated with N-acetyl-leucinal-leucinal-norleucinal.

RESULTS

Figure 11A:
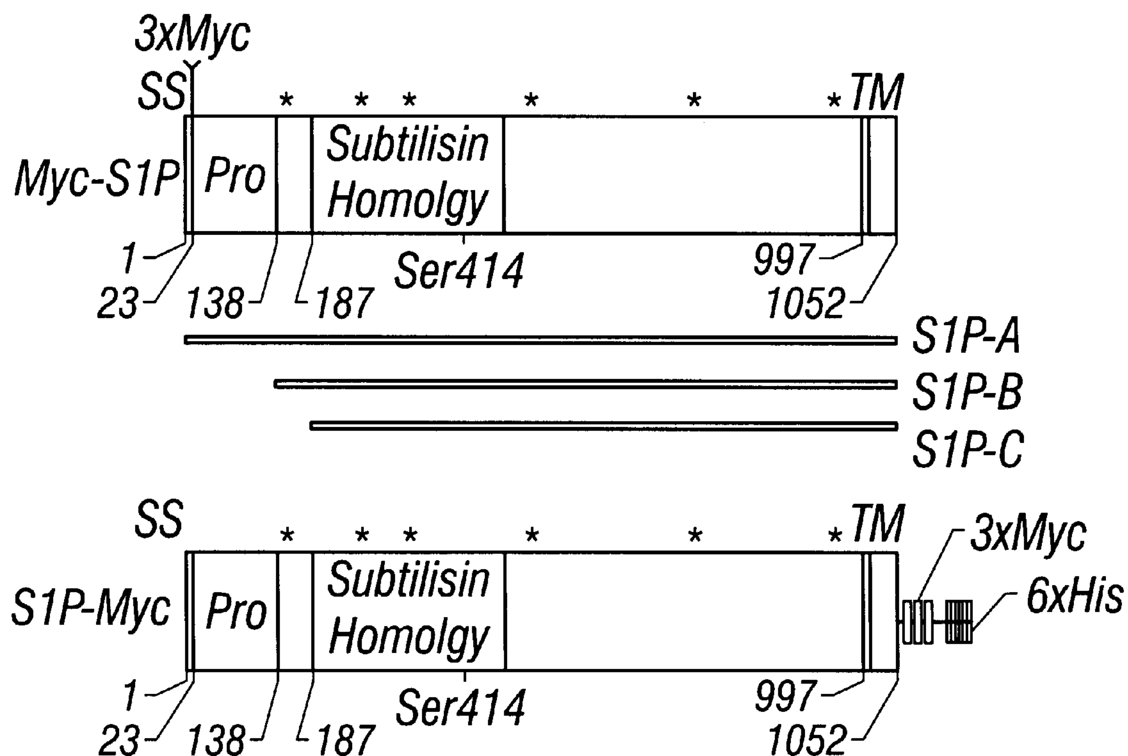
FIG. 11A. Structure of Myc-S1P, S1P-Myc, and processed versions of S1P (amino acid numbers are with respect to SEQ ID NO:1): S1P-A (amino acids 23–1052), S1P-B (amino acids 138–1052), and S1P-C (amino acids 187–1052). The propeptide sequence (Pro) and the subtilisin-like catalytic domain are boxed. The catalytic site serine (Ser414), the c-Myc epitope tags, and $His_6$ tag arc indicated. Amino acid numbers are shown below each diagram. Potential N-linked glycosylation sites are indicated by asterisks. The signal sequence (SS) and the transmembrane segment (TM) are labeled.
Figure 12A:
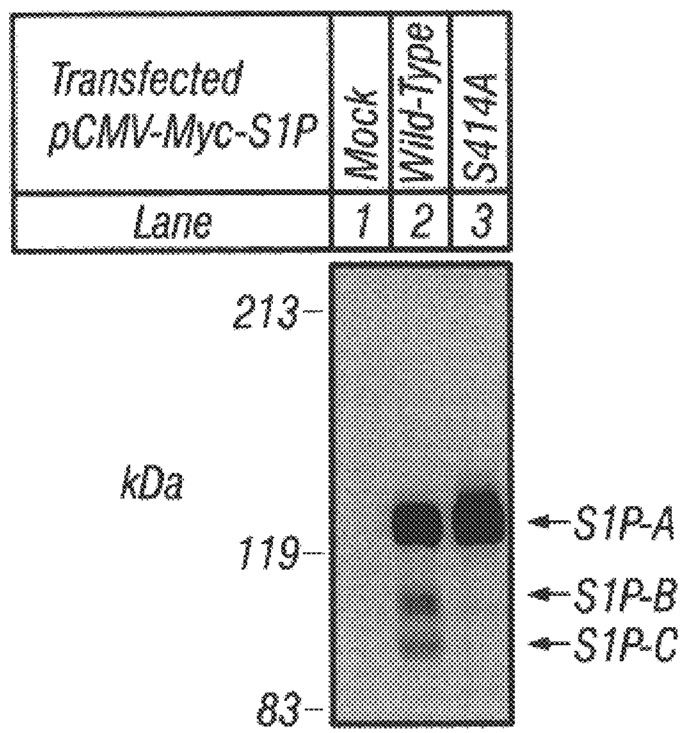
FIG. 12A. Each dish of SRD-12B cells was transfected with 2 μg pcDNA3 plus 1 μg of one of the following plasmids: pcDNA3 mock vector (FIG. 12A, lane 1); pCMV-Myc-S1P (FIG. 12A, lane 2), or pCMV-Myc-S1P(S414A) (FIG. 12A, lane 3). Cells were incubated in medium B supplemented with 5% fetal calf serum. After 18 h, cells were harvested, and $10^5$ g membrane fractions were prepared. Aliquots of membrane (20 μg) were subjected to SDS-PAGE on a 6% gel followed by immunoblot analysis with a 1:250 dilution of rabbit antiserum against the COOH-terminus of S1P. The filter was exposed to film for 2 s.

FIG. 11A outlines the structure of the precursor form of S1P and shows the position of three internal cleavage sitcs that give rise to shortened forms of S1P, designated A, B, and C. To facilitate subsequent studies, the inventors prepared cDNAs that express epitope-tagged versions of S1 P under control of the strong cytomegalovirus (CMV) promoter/enhancer. These plasmids encode versions of S1P with 3 copies of a Myc epitope tag at the $NH_2$-terminus (Myc-S1P) or the COOH-terminus (S1P-Myc). The $NH_2$-terminal Myc tag was inserted immediately after the predicted site of cleavage by signal peptidase so that it would remain with the protein after this cleavage. The COOH-terminal Myc tag was followed by six histidines, which allowed purification of the protein on a nickel column.

Example 7

Biochemical Characterization and Intracellular Localization of S1P

MATERIALS AND METHODS

Antibodies

A polyclonal antibody (U1683) against amino acids 1023–1052 of hamster S1P (SEQ ID NO:1 Sukai et al., 1998b) was generated by immunizing rabbits with a mixture of two synthetic peptides corresponding to amino acids 1023–1037 (CKAKSRPKRRRPRAKR (SEQ ID NO:29)) and 1038–1052 (CPQLTQQTHPPRTPSV (SEQ ID NO:30)) of SEQ ID NO:1, each with an additional $NH_2$-terminal cysteine residue that was conjugated to keyhole limpet hemocyanin using a standard protocol (Harlow and Iane, 1988). Monoclonal antibodies were obtained commercially as described above.

Immunoblot Analysis

Protein samples were mixed at a ratio of 5:1 with 5× loading buffer (1× loading buffer contains 30 mM Tris-HCl at pH7.4, 3% SDS (w/v), 5% (v/v) glycerol, 0.004% (v/v) bromphenol blue, and 2.5% (v/v) β-mercaptoethanol) and heated at 100° C. for 3 min prior to SDS-PAGE. Following SDS-PAGE, proteins were transferred to nitrocellulose filters, incubated with antibodies indicated in the figure legends, and detected by chemiluminescence as previously described (Sukai et al., 1998b). Gels were calibrated using prestained molecular mass markers (New England Biolabs or BioRad). Protein concentration was measured with a BCA Kit (Pierce)

Trypsin Treatment of Membranes

Transfected HEK-293 cells were cultured for 18 h in 5 ml of medium A supplemented with 5% fetal calf serum, after which cell membranes were isolated and treated with trypsin either in the absence or presence of Triton X-100 for 30 min at 30° C. as previously described (Nohturfft et al., 1998b). Treated samples were subjected to SDS-PAGE on 8% gels followed by immunoblot analysis.

Glycosidase Sensitivity of Myc-S1P

Membrane fractions from transfected SRD-12B cells were prepared as described above, after which 5 μg of membrane protein was treated with either peptide N-glycosidase F (PNGase F) or endoglycosidase H (endo H) as previously described (Sukai et al., 1999b).

RESULTS

Figure 11B:
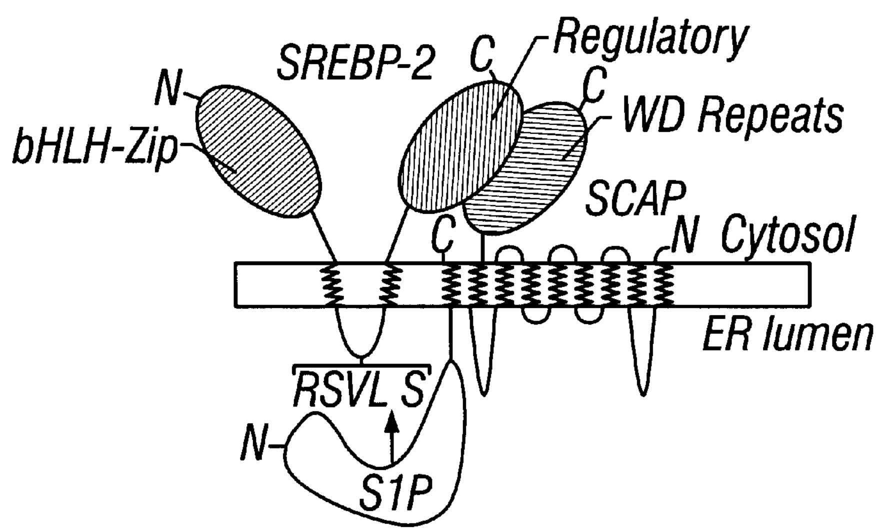
FIG 11B. Proposed membrane topology of S1P and the SREBP/SCAP complex.
Figure 11C:
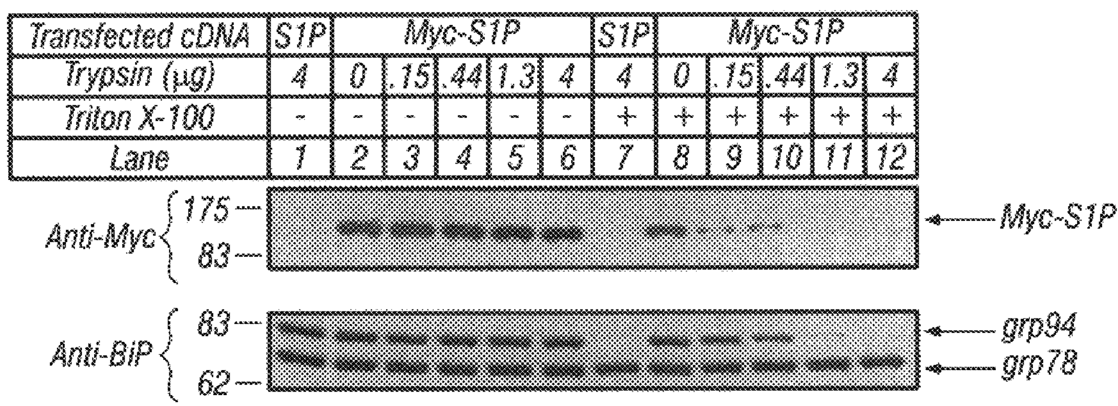
FIG. 11C and FIG. 11D. Determination of membrane topology of S1P by protease protection assays. Each dish of HEK-293 cells was transfected with 2 $\mu$g of either pCMV-Myc-S1P (FIG. 11C) or pCMV-S1P-Myc (FIG. 11D) and 2 $\mu$g of pcDNA3. Following transfection, cells were incubated in medium A supplemented with 5% fetal calf serum. After 18 h, cells were harvested, and membrane fractions ($2\times10^4$ g pellets) were prepared. Aliquots of membranes (corresponding to 0.7 dish of cells) were treated with the indicated amount of trypsin in a volume of 60 $\mu$l in the absence or presence of 1% Triton X-100 for 30 min at 30° C. Reactions were stopped by addition of trypsin inhibitor, and samples were subjected to SDS-PAGE and immunoblot analysis with 2.5 μg/ml anti-Myc monoclonal antibody 9E10 or 2 μg/ml anti-BiP antibody. Filters were probed with anti-Myc and anti-BiP antibodies and exposed to Kodak X-Omat Blue XB-1 film at room temperature for 10 s and 1 s, respectively. Molecular mass standards are expressed in kDa.
Figure 11D:
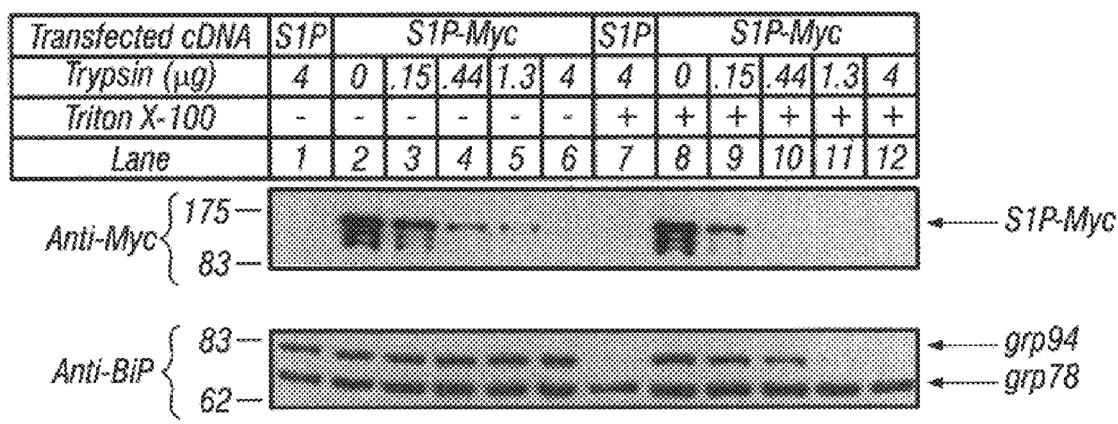

FIG. 11B shows a diagram of the SREBP/SCAP complex and the postulated position of membrane-anchored S1P with its active site juxtaposed to the cleavage site in SREBP. To confirm that the bulk of S1P is located in the ER lumen, the inventors performed protease protection assays (FIGS. 11C and 11D). HFK-293 cells were transfected with cDNAs encoding Mye-S1P (FIG. 11C) or S1P-Myc (FIG. 11D). Intact membrane vesicles were prepared and treated with varying amounts of trypsin either in the absence or presence of the detergent Triton X-100. When the epitope tag was at the $NH_2$-terminus, the tag was not destroyed by trypsin treatment of intact vesicles (FIG. 11C. lanes 3–6), but it was destroyed when the membranes were dissolved with detergent (lanes 9–12), indicating that this end of the protein is luminal. On the other hand, when the Myc tag was at the COOH-terminus, it was destroyed by trypsin both in the absence and presence of the detergent (FIG. 11D, lanes 3–6 and 9–12). To confirm that the vesicles were intact, the inventors used an anti-BiP antibody to show that an intraluminal protein, grp94, was protected from trypsin in the absence of detergent, but was destroyed in its presence (bottom panels of FIGS. 11C and 11D). Another protein visualized by the anti-BiP antibody, grp78, was resistant to trypsin even in the presence of detergent, apparently because of intrinsic trypsin resistance of this protein, a phenomenon that has been observed previously (Hua et al., 1995; Nohturfft et al., 1998a). These data confirm the membrane orientation of S1P that is shown in FIG. 11B.

To study the processing of S1P, the inventors used SRD-12B cells that lack endooenous S1P. The inventors transfected the cells with pCMV-Myc-S1P and studied the fate of the COOH-terminus by immunoblotting with an antibody against the cytoplasmic tail of S1P (FIG. 12A). The immunoblot revealed three bands that the inventors designate S1P-A, -B, and -C (lane 2). To determine whether these protein species result from autoproteolytic processing, the inventors transfected the cells with pCMV-Myc-S1P in which the serine at the active site was mutated to alanine (S414A). In this case, only S1P-A was visualized (lane 3), indicating that processing to the B and C forms requires a functional active site and is autocatalytic. Inasmuch as the antibody recognizes the extreme COOH-terminus of S1P, the data indicate that S1P-B and S1P-C must have been produced by proteolytic removal of $NH_2$-terminal sequences.

Figure 12B:
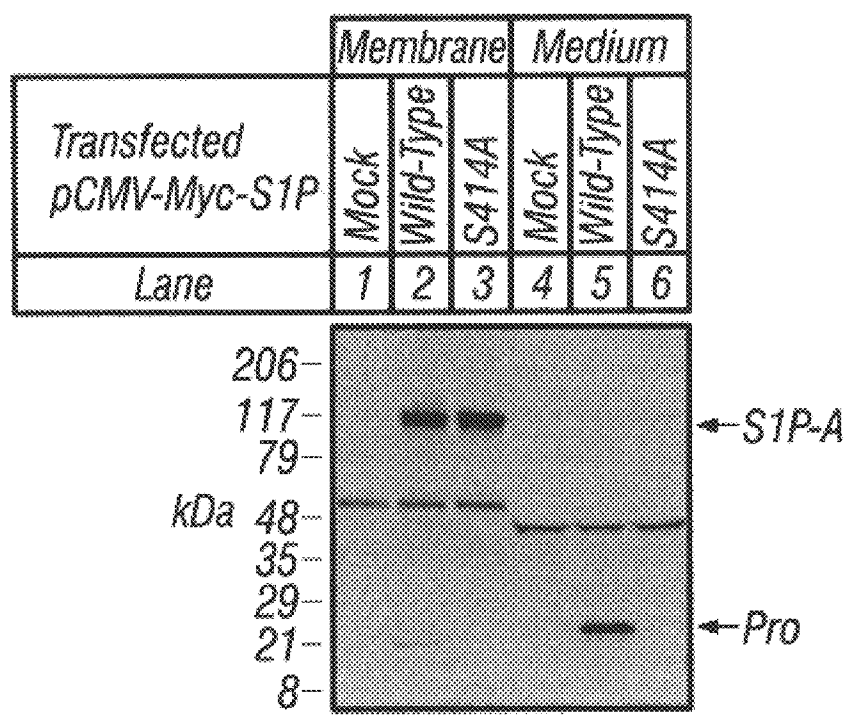
FIG. 12B. Each dish of HEK-293 cells was transfected with 2 μg pcDNA3, 1 μg pVAI, and 1 μg of one of the following plasmids: pcDNA3 mock vector (FIG. 12B, lanes 1 and 4); pCMV-Myc-S1P (FIG. 12B, lanes 2 and 5), or pCMV-Myc-S1P(S414A) (FIG. 12B, lanes 3 and 6). Following transfection, cells were incubated in 2 ml of medium A supplemented with 1% newborn calf lipoprotein-deficient serum. After 25 h, cells were harvested, the medium was saved, and $10^5$ g membrane pellets were prepared. Aliquots of membranes and medium (each corresponding to 0.12 dish of cells) were subjected to SDS-PAGE on a 4–15% gradient gel followed by immunoblot analysis with 2.5 μg/ml anti-Myc 9E10. The filter was exposed to film for 7 s. Pro denotes the processed propeptide of Myc-S1P.
Figure 13:
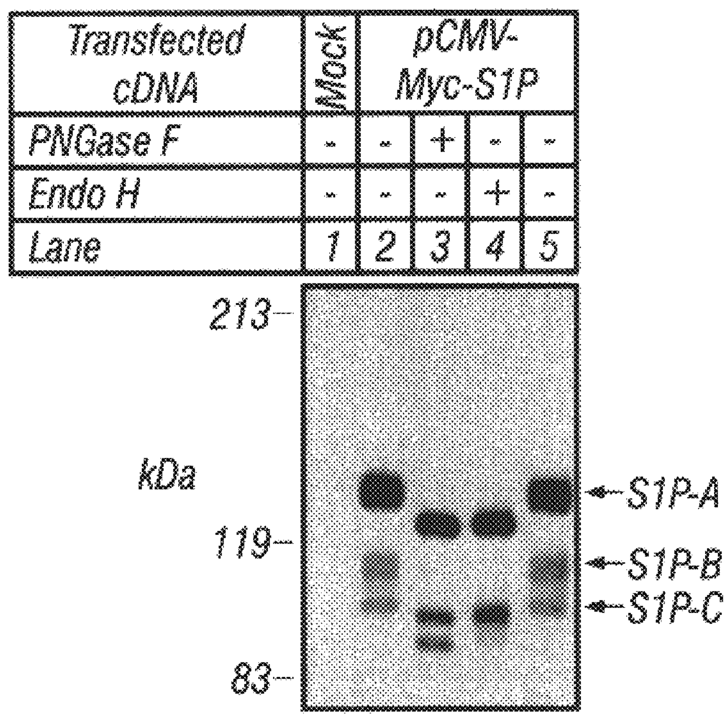
FIG. 13. Analysis of N-linked carbohydrates of Myc-S1P in transfected SRD-12B cells. SRD-12B cells were transfected with either mock vector (lane 1) or pCMV-Myc-S1P (lanes 2–5) as described in FIG. 12. Cells were incubated in medium B supplemented with 5% fetal calf serum. After 18 h, cells were harvested, and $10^5$ g membrane fractions were prepared. The membranes were resuspended in SDS lysis buffer. Aliquots (5 μg) were boiled and treated with either 0.26 IU/ml peptide N-glycosidase F (PNGaseF) or 0.83 IU/ml endo H. The samples were subjected to SDS-PAGE on a 6% gel and immunoblotted with a 1:250 dilution of anti-S1P serum. The filter was exposed to film for 15 s.

FIG. 12B shows an experiment designed to analyze the fate of the $NH_2$-terminal propeptide generated during the proteolytic processing of S1P. For this purpose, the inventors used HEK-293 cells, which yield higher levels of protein from transfected cDNAs than do SRD-12B cells. The inventors transfected HFK-293 cells with pCMV-Myc-S1P and subjected aliquots of the culture medium and a $10^5$ g membrane fraction to SDS-PAGE and immunoblotted with an antibody against the $NH_2$-terminal Myc tag. The membranes contained a single immunoreactive band corresponding to S1P-A (lane 2). The mediunm contained a single band at ~24 kDa (lane 5). This band was not visualized when the inventors transfected the epitope-tagged S414A mutant of S1P (lane 6), indicating that it was generated by autocatalytic cleavage. The inventors believe that this secreted protein fragment represents the $NH_2$-terminal propeptide that is cleaved to generate S1P-B (see below). S1P contains six potential sites of N-linked glycosylation that are indicated by asterisks in FIG. 11A. When SRD-12B cells were transfected with pCMV-Myc-S1P, the mobility of S1P-A, S1P-B, and S1P-C were all increased after treatment with PNGase F, indicating that they all contained N-linked carbohydrate (FIG. 13, lane 3). When the membranes were treated with endo H, the mobility of S1P-A and S1P-B increased while the mobility of S1P-C did not change. As a result, after endo H treatment S1P-B and S1P-C comigrated on the gel (FIG. 13, lane 4). These findings indicate that the carbohydrate chains of S1P-A and S1P-B remain in the high mannose, endo H-sensitive form characteristic of ER proteins, whereas S1P-C undergoes processing by Golgi mannosidase II.

Example 8

Identification of the Processing Intermediates of S1P

MATERIALS AND METHODS $NH_2$-terminal Sequence Analysis of Immunoprecipitated Forms of S1P SRD-12B cells and SRD-12B cells stably transfected with pCMV-S1P-Myc (designated S1P(1052) cells) were grown in roller bottles and set up at $4\times10^7$ cells/850-$cm^2$ bottle in medium B supplemented with 5% fetal calf serum. The medium was changed every other day. On day 6, the medium was changed to medium B supplemented with 5% newborn calf lipoprotein-deficient serum. On day 7, the cells were collected and washed with ice cold phosphate-buffered saline. The washed cell pellet (~10 ml of packed cells) was lysed in 40 ml of buffer A (50 mM Tris-HCl at pH 8.0, 1.5% (v/v) Nonidet P-40, 0.1% (w/v) SDS, 0.5% (w/v) deoxycholic acid, 150 mM NaCl, 2 mM $MgCl_2$) supplemented with 1 mM Pefabloc®, 1 mM phenylmethylsulfonyl fluoride, 20 $\mu$g/ml leupeptin, 10 $\mu$g/ml pepstatin A, and 5 $\mu$g/ml aprotinin. The cell lysate was rocked for 1 h at 4° C. followed by centrifugation at $2\times10^5$ g for 1 h at 4° C. The resulting supernatant was incubated with 500 $\mu$g of monoclonal 9E10 anti-Myc conjugated to agarose beads (Santa Cruz, Biotechnology, Inc.) with continuous rocking for 6 h at 4° C. The beads were then pelleted by centrifugation for 10 min at 3000 g. The resulting supernatant was discarded, and the pellet was washed twice with 5 ml ice cold buffer A. The pellet was further washed by rocking overnight at 4° C. in 10 ml of buffer A, after which the pellet was resuspended in 4 ml buffer A and divided into 4 aliquots. Each of the aliquots was washed 6 times with 0.7 ml of buffer A. Each pellet was then resuspended in 50 $\mu$l of 2× SDS loading buffer (Laemmli, 1970), boiled for 10 min, and centrifuged briefly at 12,000 g. Aliquots of the supernatant were subjected to SDS-PAGE and either stained with Coomassie blue or transferred to a poly(vinylidene fluoride) membrane (Millipore Corp.) and then stained with Coomassie blue. The five Coomassic blue-stained bands that appeared in immunoprecipitates from the S1P(1052) cells were each cut from the membrane and subjected to $NH_2$-terminal sequence analysis by automated Edman degradation performed with Procise Model 494 Sequencer from PE Biosystems (Foster City, Calif.), using standard programming and chemicals as recommended by the manufacturer.

RESULTS

Figure 14A:
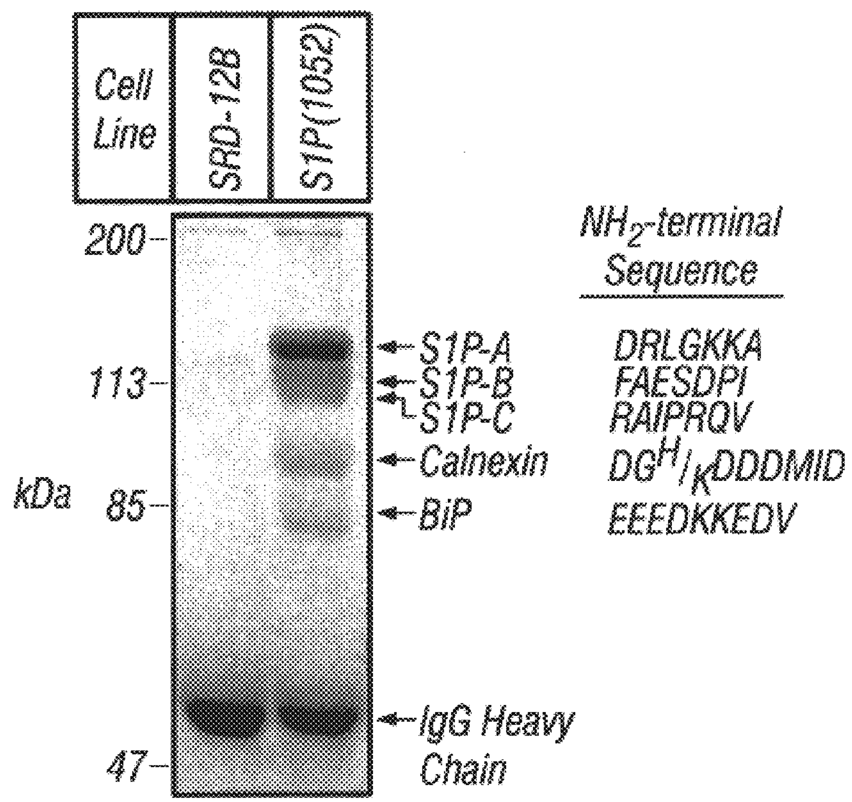
FIG. 14A. Roller bottles of SRD-12B cells and S1P(1052) cells expressing pCMV-S1P-Myc were lysed in buffer A. The $2\times10^5$ g supernatant was immunoprecipitated with monoclonal 9E10 anti-Myc antibody conjugated to agarose. Aliquots of the immunoprecipitates (corresponding to one-half of a roller bottle of cells) were solubilized in 2×SDS loading buffer and subjected to 5–20% gradient SDS-PAGE. Half of the gel was stained with Coomassie blue and the other half was transferred to a poly(vinylidene fluoride) membrane and then stained with Coomassie blue. Bands corresponding to the five Coomassie blue-stained proteins from the S1P(1052) cells were cut from the membrane and sequenced by automated Edman degradation. Each band contained about 5 pmol of protein.
Figure 14B:
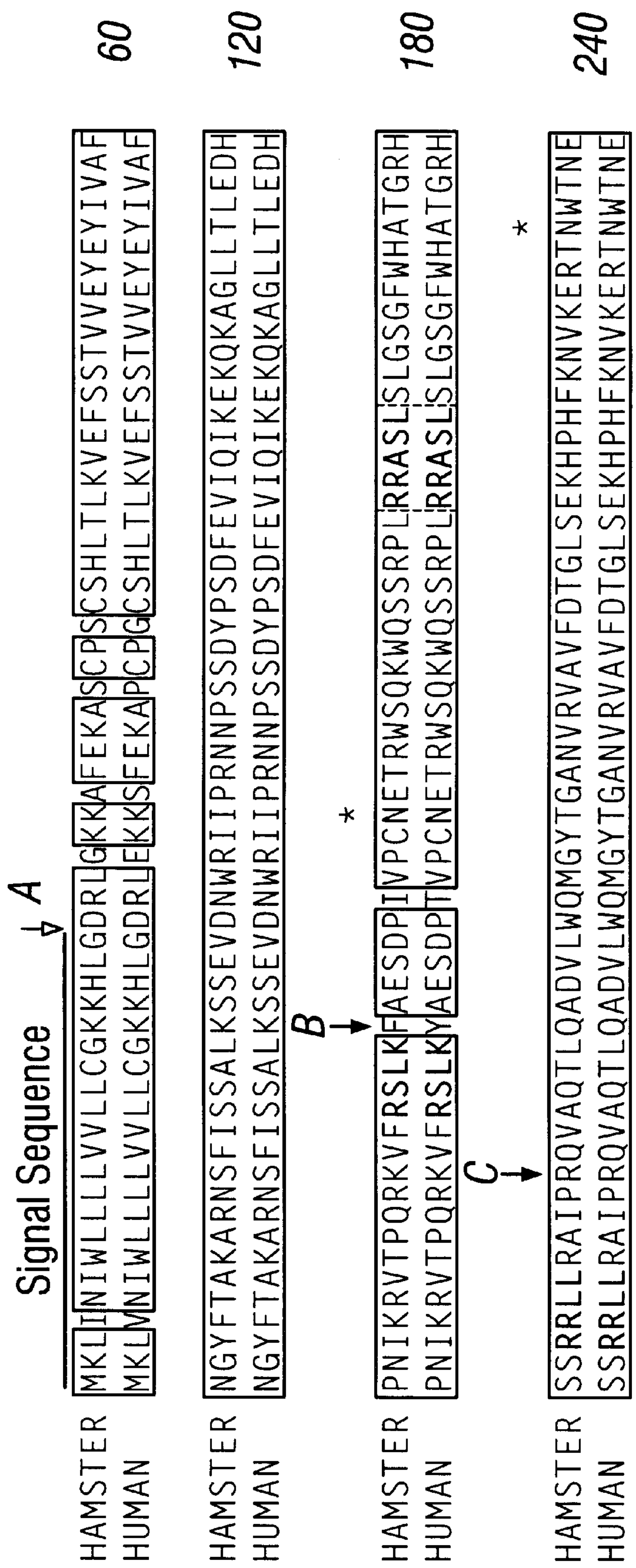
FIG. 14B. Amino acid sequence of hamster and human S1P (corresponding to residues 1–240 of SEQ ID NO:1 and SEQ ID NO:3, respectively). Residue numbers are shown at the right. Identical residues are boxed. The signal sequence is denoted by the solid overbar. The signal peptidase cleavage site is denoted as Site-A (open arrow). The S1P processing sites are designated Site-B and Site-C (closed arrows). The putative recognition sequences at the two processing sites are highlighted in black. A potential processing site is shaded. Potential N-linked glycosylation sites are denoted by asterisks.

To identify the sites within S1P where processing occurs, the inventors transfected SRD-12B cells with pCMV-S1P-Myc, which produces S1P with a Myc tag at the COOH-terminus. A permanent line of transfected cells. designated S1P(1052), was selected by growth in the absence of cholesterol, and the cells were cultured in bulk in roller bottles. Cell pellets were solubilized, and S1P-Myc proteins were immunoprecipitated with anti-Myc, subjected to SDS-PAGE, and stained with Coomassie blue (FIG. 14A). As a control, the inventors prepared cell lysates from untransfected SRD-12B cells that were sustained by addition of cholesterol and unsaturated fatty acids to the growth medium. The immunoprecipitates from the S1P(1052) cells contained five visible polypeptide bands that were not visualized in the control cells. Each of these bands was excised from a poly(vinylidene fluoride) blot and sequenced at the $NH_2$-terminal end by Edman degradation. Three of the bands corresponded in size to S1P-A, -B, and -C, respectively. The sequences indicated that S1P-A is the product of signal peptidase cleavage at the Gly-Asp bond after residue 22 (see FIG. 14B, $NH_2$-terminal sequence DRLGKKA, SEQ ID NO:31). S1P-B resulted from cleavage after residue 137 following the sequence RSLK (SEQ ID NO:18) (see FIG. 14B, $NH_2$-tcrminal sequence FAESDPI, SEQ ID NO:32). S1P-C resulted from cleavage after residue 186 following the sequence RRLL (SEQ ID NO:19) (see FIG. 14B, $NH_2$-terminal sequence RAIPRQV, SEQ ID NO:33). All of these sequences are completely conserved in the human and hamster proteins (FIG. 14B). Sequencing the two remaining bands on the gel revealed that these were calnexin (see FIG. 14B, $NH_2$-terminal sequence DGKDDDMID, SEQ ID NO:34 or DGHDDDMID, SEQ ID NO:35). and BiP (see FIG. 14B, $NH_2$-tcrminal sequence EEEDKKEDV, SEQ ID NO:36)., two protein chaperones that may form transient complexes with S1P, as they do with many ER proteins (Hebert et al., 1995).

Example 9

Characterization of the Enzymatic Activities of processed Forms of S1P

RESULTS

Figure 15A:
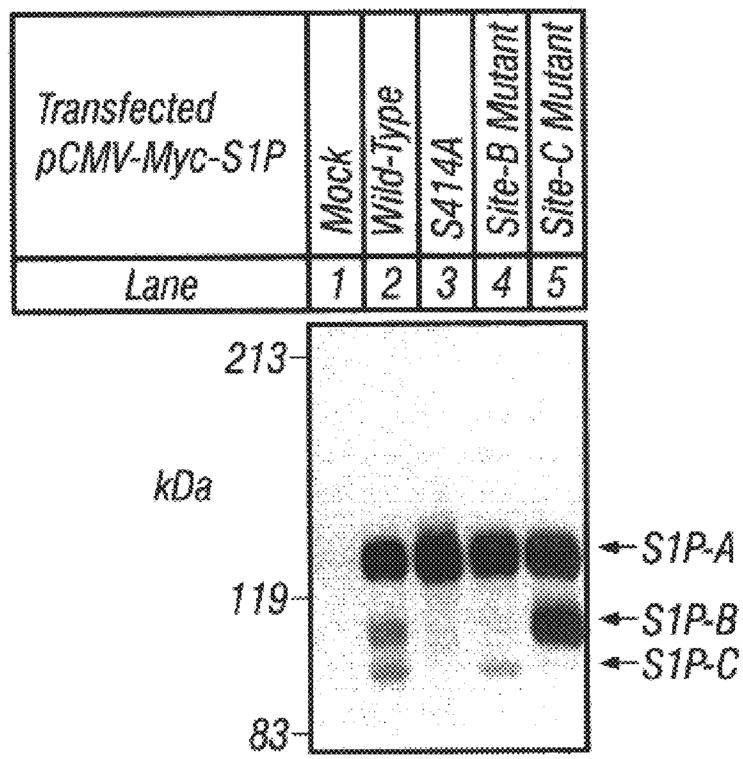
FIG. 15A. Each dish of SRD-12B cells was transfected with 2 μg of pcDNA3 and 1 μtg of one of the following plasmids: pcDNA3 mock vector (FIG. 15A, lane 1); pCMV-Myc-S1P (FIG. 15A, lane 2); pCMV-Myc-S1P(S414A) (FIG. 15A, lane 3); pCMV-Myc-S1P(Site-B mutant) (FIG. 15A, lane 4); or pCMV-Myc-S1P (Site-C mutant) (FIG. 15A, lane 5). Cells were then incubated in medium B supplemented with 5% fetal calf serum. After 18 h, cells were harvested, and $10^5$ g membrane fractions were prepared. Aliquots of membrane (20 μg) were subjected to SDS-PAGE on a 6% gel and immunoblotted with a 1:250 dilution of rabbit anti-S1P serum. The filter was exposed to film for 2 s.

To determine whether the A, B, and C forms of S1P are functional, the inventors prepared cDNAs encoding mutant forms of S1P with altered sequences at the B and C cleavage sites. In the Site-B mutant, the RSLK sequence at the B cleavage site was changed to AAAA (SEQ ID NO:21). In the Site-C mutant, the inventors changed the P4 to P1T positions of the C cleavage site from RRLLR (SEQ ID NO:22) to AAAAA (SEQ ID NO:23), and the inventors also altered a nearby sequence that might have served as an alternative cleavage site (RRASL at residues 163–167 of SEQ ID NO:1 changed to VAASL (SEQ ID NO:37)) (see shaded box in FIG. 14B). The cDNAs were introduced into SRD-12B cells by transfection, and the processed forms of S1P were subjected to SDS-PAGE and visualized by immunoblotting with the antiserum against the COOH-terminal tail of S1P. As shown in FIG. 15A, the cDNA encoding wild-type S1P yielded bands corresponding to S1P-A, S1P-B, and S1P-C (lane 2), while the inactive S414A mutant showed only the S1P-A band (lane 3). Mutation at Site-B eliminated S1P-B, and it markedly reduced S1P-C (lane 4). The Site-C mutant failed to produce S1P-C, but it produced increased amounts of S1P-B (lane 5).

Figure 15B:
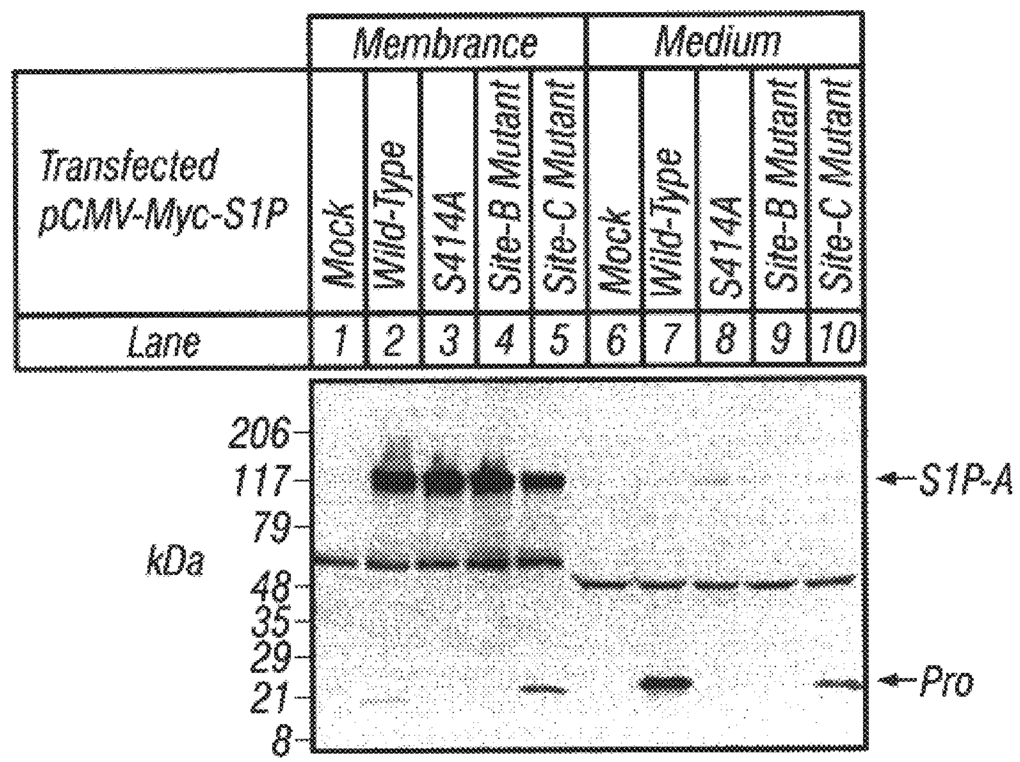
FIG. 15B. Each dish of HEK-293 cells was transfected with 2 μg pcDNA3, 1 μg pVAI, and 1 μg of one of the following plasmids: pcDNA3 mock vector (FIG. 15B, lanes 1 and 6); pCMV-Myc-S1P (FIG. 15B, lanes 2 and 7); pCMV-Myc-S1P(S414A) (FIG. 15B, lanes 3 and 8); pCMV-Myc-S1P(Site-B mutant) (FIG. 15B, lanes 4 and 9); or pCMV-Myc-S1P (Site-C mutant) (FIG. 15B, lanes 5 and 10). Following transfection, cells were incubated in 2 ml of medium A supplemented with 1% newborn calf lipoprotein-deficient serum. After 25 h, cells were harvested, the medium was saved, and $10^5$ g membrane pellets were. Aliquots of membrane pellets and medium (corresponding to 0.12 dish of cells) were subjected to SDS-PAGE on a 4–15% gradient gel and immunoblotted with 2.5 μg/ml anti-Myc 9E10. The filter was exposed to film for 7 s. Pro denotes the processed propeptide of Myc-S1P.

To monitor the cleavage of S1P from the $NH_2$-terminal end, the inventors transfected the wild-type and mutant constructs into HEK-293 cells and studied the secretion of the propeptide by immunoblotting membrane pellets and aliquots of the culture medium with the antibody against the $NH_2$-terminal Myc tag (FIG. 15B). In the membrane pellets, the precursor form of S1P, S1P-A, was present in cells transfected with the wild-type S1P and all of the mutants. The membranes contained increased amounts of a band corresponding to the propeptide when the Site-C mutant was expressed (FIG. 151B, lane 5). The medium contained the propeptide fragment when the cells expressed either wild-type S1P (lane 7) or the Site-C mutant (lane 10), but not when the cells expressed the S414A mutant or the Site-B mutant (lanes 8 and 9).

The inventors interpret the data of FIG. 15 to indicate that the A form of S1P is initially cleaved autocatalytically at Site-B, and subsequently at Site-C. If Site-B cleavage is blocked, as in the Site-B mutant, cleavage at Site-C is reduced. On the other hand, inhibiting Site-C cleavage, as in the Site-C mutant, does not interfere with Site-B cleavage. Since Site-B cleavage occurs first, a single Myc-tagged propeptide is secreted. This protein co-migrates on SDS-PAGE with a recombinant protein that corresponds to amino acids 23–137 of S1P (SEQ ID NO:1).

The inventors used the Site-B and -C mutants to determine whether S1P-A, -B, or -C is active in cleaving SREBP-2 (FIG. 16). For this purpose, the inventors transfected SRD-12B cells with a cDNA encoding a version of human SRFBP-2 with an HSV epitope tag at the $NH_2$-terminus. The inventors cotransfected cDNAs encoding wild-type S1P or one of the mutants. Cell membrane pellets and nuclear extracts were subjected to SDS-PAGE. and the $NH_2$-terminus of SREBP-2 was visualized by immunoblotting with anti-HSV (FIG. 16A). In the absence of cotransfected S1P, the membranes contained the precursor form of SREBP-2, but there was no nuclear form (lane 2). The nuclear form appeared when the inventors cotransfected as little as 0.03 $\mu$g of wild-type pTK-Myc-S1P (lane 3). As described above, the S414A mutant of S1P was inactive, even when a 10-fold larger amount (0.3 $\mu$g) was transfected (lanes 6-8). The Site-B mutant gave rise to the cleaved nuclear form of SREBP-2, but this weak activity required >10-fold higher levels of expression of the Site-B mutant as compared to wild-type S1P (compare lanes 11 and 3). On the other hand, the Site-C mutant was as active as the wild-type S1P (lanes 12–14). Immunoblotting with anti-S1P confirmed that equivalent amounts of each of the S1P plasmids gave rise to equal amounts of S1P-A (FIG. 16B). As described above, wild-type S1P gave rise to the B and C forms, which were not seen with the S414A mutant or the Site-B mutant. The Site-C mutant gave rise only to the A and B forms of S1P. A comparison of the data in FIG. 16A and 16B reveals that wild-type S1P achieved maximal cleavage of SREBP-2 at a concentration at which the expression of S1P was barely detectable (compare lane 3 in FIG. 16A and 16B). The inventors attribute this observation to the relative insensitivity of the anti-S1P immunoblot and the fact that S1P acts catalytically so that only a small amount of active enzyme is able to cleave all of the accessible SREBP-2.

Figure 16A:
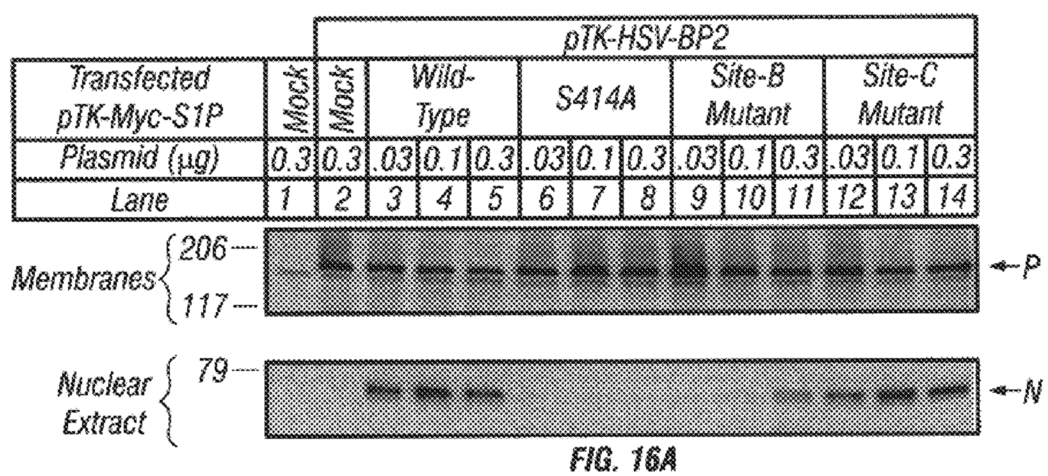
FIG. 16A. Each dish of SRD-12B cells was transfected with 0.1 μg of pCMV-SCAP(D443N), 2.5 μg of either pTK mock vector (FIG. 16A, lane 1) or pTK-HSV-BP2 (FIG. 16A, lanes 2–14), and the indicated amount of one of the following plasmids: pTK mock vector (FIG. 16A, lanes 1 and 2), pTK-Myc-S1P (FIG. 16A, lanes 3–5), pTK-Myc-S1P (S414A) (FIG. 16A, lanes 6–8), pTK-Myc-S1P(Site-B mutant) (FIG. 16A, lanes 9–11), or pTK-Myc-S1P (Site-C mutant) (FIG. 16A, lanes 12–14). The total amount of DNA was adjusted to 3 μg/dish by the addition of pTK mock vector. Following transfection, cells were incubated in medium B supplemented with 5% fetal calf serum. After 18 h, cells were harvested, and the nuclear extract and $10^5$ g membrane pellets were prepared. Aliquots of nuclear extract (1 μg) and membranes (5 μg) were subjected to SDS-PAGE on 8% gels followed by immunoblot analysis with 0.5 μg/ml anti-HSV tag antibody. The filters were exposed to film for 1 s.
Figure 16B:
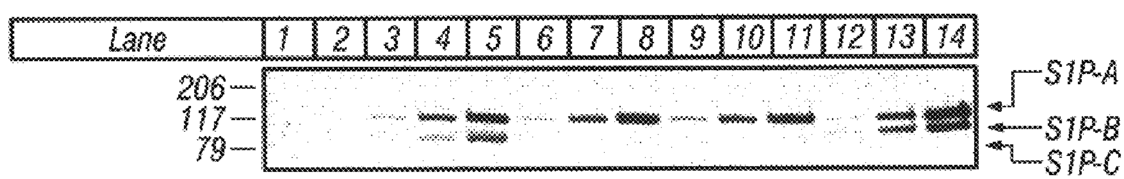
FIG. 16B. Aliquots (15 μg) of $10^5$ g membrane pellets prepared from the transfected SRD-12B cells in FIG. 16A were subjected to SDS-PAGE on an 8% gel followed by immunoblot analysis with a 1:250 dilution of anti-S1P serum. The filter was exposed to film for 3 min.
Figure 16C:
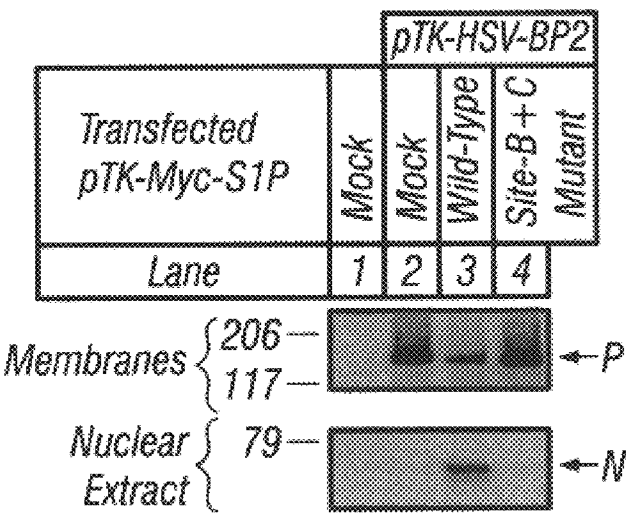
FIG. 16C. Each dish of SRD-12B cells was transfected with 0.1 μg of pTK mock vector, 0.1 μg of pCMV-SCAP(D443N), 2.5 μg of either pTK mock vector (FIG. 16C, lane 1) or pTK-HSV-BP2 (FIG. 16C, lanes 2–4), and 0.3 μg of one of the following plasmids: pTK mock vector (FIG. 16C, lanes 1 and 2), pTK-Myc-S1P (FIG. 16C, lane 3), or pTK-Myc-S1P (Site-B+C mutant) (FIG. 16C, lane 4). Nuclear extract and $10^5$ g membrane pellets were prepared as described in FIG. 16A. Aliquots of nuclear extract (1 μg) and membranes (2 μg) were subjected to SDS-PAGE on an 8% gel followed by immunoblot analysis with 0.5 μg/ml anti-HSV tag antibody. The filters were exposed to film for 1 s.
Figure 16D:
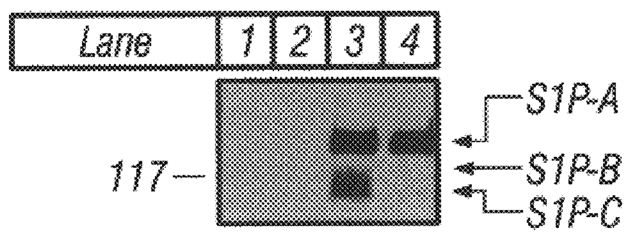
FIG. 16D. Aliquots (15 μg) of the $10^5$ g membrane pellets prepared in FIG. 16C were subjected to SDS-PAGE on a 6% gel followed by immunoblot analysis with a 1:250 dilution of anti-S1P serum. The filter was exposed to film for 5 min. P and N denote the precursor and cleaved nuclear forms of SREBP-2, respectively. Molecular mass standards are expressed as kDa.

To directly test the cleavage activity of S1P-A, the inventors repeated the SREBP-2 cleavage assay using a mutant S1P cDNA that contained both the Site-B and Site-C mutations, designated S1P(Site-B+C mutant). SRD-12B cells transfected with the Site B+C mutant (FIG. 16D. lane 4) expressed only S1P-A as revealed by immunoblotting with anti-S1P serum. Ihus, mutation at both Site-B and Site-C blocked all detectable processing of S1P-A. In contrast to the results for the individual Site-B and Site-C mutants (FIG. 16A, lanes 11 and 14), cotransfection of SRD-12B cells with SREBP-2 and the Site B+C mutant of S1P resulted in no detectable cleaved nuclear form of SREBP-2 (FIG. 16C, lane 4). These data indicate that S1P-A is an inactive precursor of S1P that requires the removal of the $NH_2$-terminal propeptide in order to generate the two active forms S1P-B and S1P-C, that can cleave SREBP-2.

Figure 17:
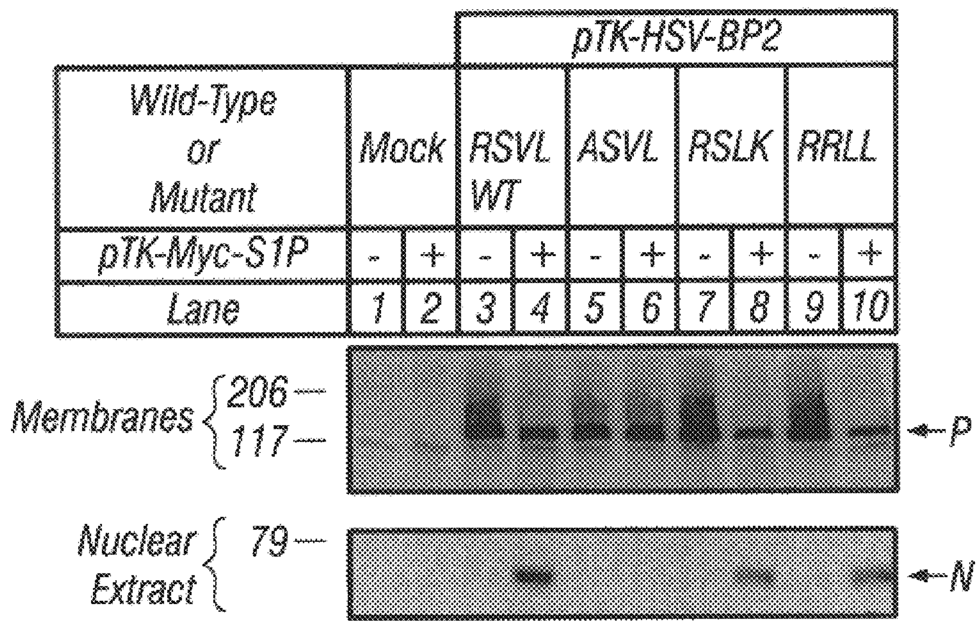
FIG. 17. S1P-dependent cleavage of epitope-tagged mutant SREBP-2 in transfected SRD-12B cells. Each dish of SRD-12B cells was transfected with 0.1 μg of pCMV-SCAP (D443N), 0.25 μg of either pTK mock vector (lanes 1,3,5,7, and 9) or pTK-Myc-S1P (lanes 2,4,6,8, and 10), and 3 μg of the indicated plasmid: pTK mock vector (lanes 1 and 2), pTK-HSV-BP2 (lanes 3 and 4), pTK-HSV-BP2(R519A) (lanes 5 and 6), pTK-HSV-BP2(RSLK) (lanes 7 and 8), or pTK-HSV-BP2(RRLL) (lanes 9 and 10). Following transfection, cells were incubated in medium B supplemented with 5% fetal calf serum. After 18 h, cells were harvested, and the nuclear extract and $10^5$ g membrane fractions were prepared. Aliquots of nuclear extract (2 μg) and membrane pellets (5 μg) were subjected to SDS-PAGE on 8% gels followed by immunoblot analysis with 0.5 g/ml anti-HSV tag antibody. The filters were exposed to film for 1 s. P and N denote the precursor and cleaved nuclear forms of SREBP-2, respectively. Molecular mass standards are expressed as kDa.

The data of FIGS. 15 and 16 suggest that S1P-B and S1P-C are produced by autocatalytic cleavage. If this is true, then S1P must be able to recognize sequences corresponding to Site-B and Site-C (RSLK (SEQ ID NO:18) and RRLL (SEQ ID NO:19), respectively) in addition to the RSVL (SEQ ID NO:1 ) sequence that is cleaved in SREBP-2. To test this hypothesis, the inventors prepared cDNAs encoding mutant forms of HSV-tagged SREBP-2 with the putative Site-B and Site-C recognition sequences substituted for the native RSVL (SEQ ID NO:11) sequence (FIG. 17). These cDNAs were transfected into SRD-12B cells with or without a cDNA encoding wild-type S1P. Membranes and nuclear extracts were subjected to SDS-PAGE and immunoblotted with anti-HSV. The data revealed that S1P is able to cleave SREBP-2 containing the Site-B sequence (RSLK (SEQ ID NO:18)) (lane 8) and the Site-C sequence (RRLL (SEQ ID NO:19)) (lane 10) as well as the wild-type sequence (RSVL (SEQ ID NO:11)) (lane 4). As expected, cleavage of the wild-type sequence was abolished when the inventors replaced the arginine at the P4 position with alanine (ASVL (SEQ ID NO:38)) (lane 6). Cleavage of the Site-B and Site-C sequences were also abolished by the arginine to alanine replacement at P4 (data not shown).

Figure 18A:
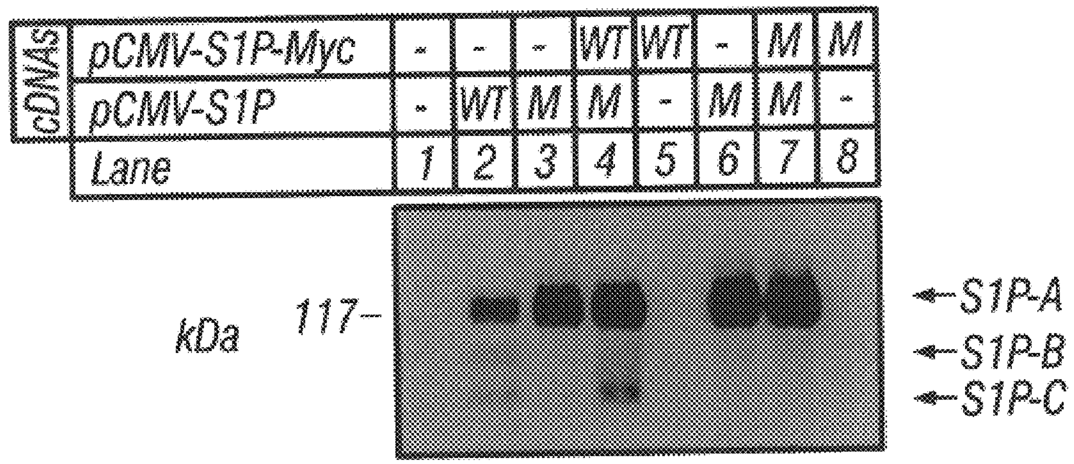
FIG. 18A. Each dish of SRD-12B cells was transfected with 1 μg of either pCMV-S1P (FIG. 18A, lane 2) or pCMV-S1P(S414A) (FIG. 18A, lanes 3,4,6, and 7) plus 0.1 μtg of either pCMV-S1P-Myc (FIG. 18A, lanes 4 and 5) or pCMV-S1P-Myc(S414A) (FIG. 18A, lanes 7 and 8). The total amount of DNA in all lanes was adjusted to 3 μg/dish by the addition of pcDNA3 mock vector. Following transfection, cells were incubated in medium B supplemented with 5% fetal calf serum. After 18 h, the cells were harvested, and $10^5$ g membrane fractions were prepared. Aliquots of membrane (5 μg) were subjected to SDS-PAGE on a 6% gel followed by immunoblot analysis with a 1:250 dilution of anti-S1P serum. The filter was exposed to film for 1 s. WT and M denote the wild-type S1P and S414A mutant cDNAs, respectively.
Figure 18B:
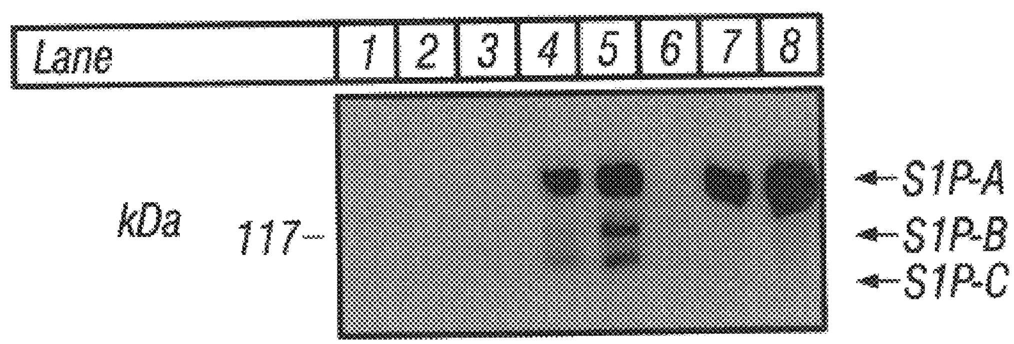
FIG. 18B. Aliquots (5 μg) of $10^5$ g membrane fractions prepared from the transfected cells in FIG. 18A were subjected to SDS-PAGE on a 6% gel followed by immunoblot analysis with 2.5 μg/ml anti-Myc 9E10 antibody. The filter was exposed to film for 2 s.

The experiment of FIG. 18 was designed to reveal whether each S1P molecule cleaves itself in an intramolecular reaction to generate the B and C forms, or whether one active S1P molecule cleaves another in an intermolecular reaction. The inventors transfected SRD-12B cells with a cDNA encoding untagged wild-type S1P or the S414A mutant. In addition, the inventors cotransfected the wild-type or S414A version of pCMV-S1P-Myc. Membrane extracts were subjected to SDS-PAGE and immunoblotted with the antibody against the COOH-terminus of S1P. Fortuitously, this antibody does not react with S1P that has a Myc tag at the COOH-terminus, allowing the inventors to visualize only the untagged S1P. As expected, when the SRD-12B cells expressed wild-type S1P, they exhibited S1P-A, -B, and -C (lane 2), whereas only S1P-A appeared when the cells expressed the S414A mutant (lane 3). When Myc-tagged wild-type S1P was co-expressed, S1P-C appeared, but S1P-B did not (lane 4). The Myc-tagged S1P by itself did not yield a visible band (lane 5). These results show that an active S1P enzyme can cleave another S1P molecule at Site-C, but not at Site-B. Thus, cleavage at Site-B must occur intramolecularly. Lanes 6–8 are controls which demonstrate that the Myc-tagged S414A mutant was not able to cleave the S414A mutant S1P to generate S1P-C. FIG. 18B shows the same extracts blotted with the anti-Myc antibody, which reveals that the Myc-tagged S1P was indeed processed to the B and C forms (lanes 4 and 5), but not when it contained the S414A mutation (lanes 7 and 8).

Example 10

The Effects of Sterols on the Regulation of Proteolyitic Processing of S1P

RESULTS

Figure 19A:
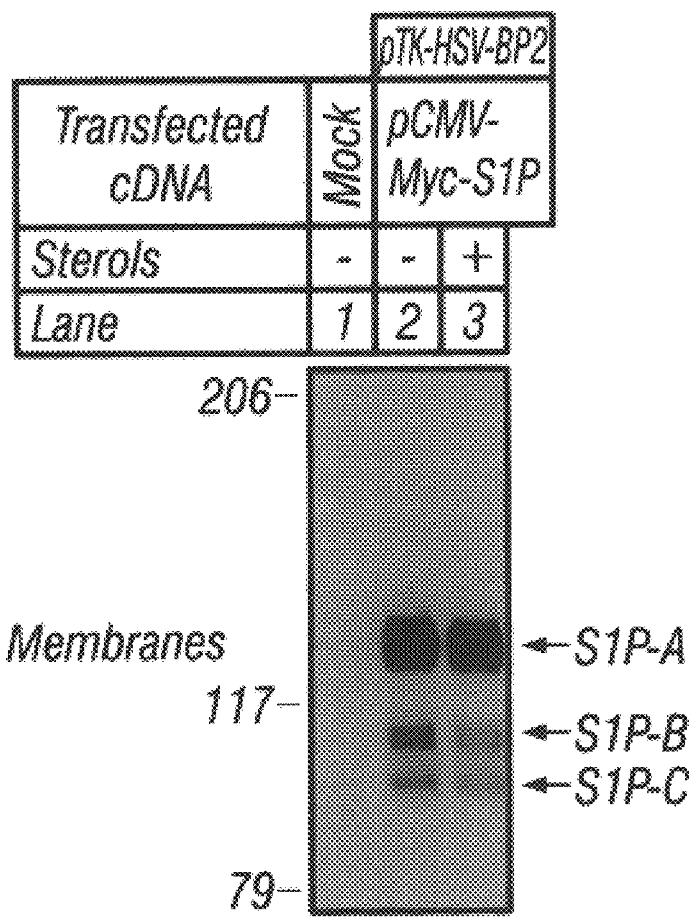
FIG. 19A. Aliquots of membranes (10 μg) were subjected to SDS-PAGE on a 6% gel followed by immunoblot analysis with a 1:250 dilution of anti-S1P serum. The filter was exposed to film for 2 s.
Figure 19B:
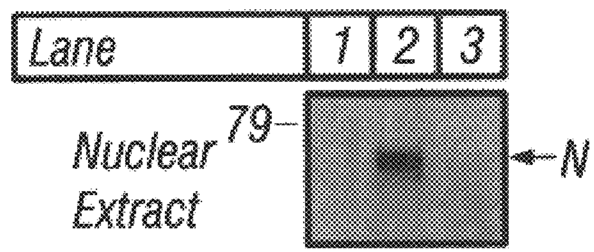
FIG. 19B. Aliquots of nuclear extracts (8 μg) were subjected to SDS-PAGE on an 8% gel followed by immunoblot analysis with 0.5 μg/ml of anti-HSV tag antibody. The filter was exposed to film for 45 s. N denotes the cleaved nuclear form of SREBP-2. Molecular mass markers are expressed as kDa.

If S1P must be processed to the B or C form in order to be active, it is possible that sterols block S1P activity by inhibiting the processing reaction. TIo test this hypothesis, the inventors transfected SRD-12B cells with pCMV-Myc-S1P plus a cDNA encoding HSV-tagged SREBP-2 (FIG. 19). The cells were incubated without or with sterols. Membranes were blotted with anti-S1P (FIG. 19A), and nuclear extracts were blotted with anti-HSV (FIG. 19B). The processing of S1P to the B and C forms occurred equally in the absence and presence of sterols (compare lanes 2 and 3 of FIG. 19A). On the other hand, nuclear SREBP-2 was produced only in the absence of sterols (lane 2 of FIG. 19B). These data indicate that sterols do not regulate the conversion of S1P to its active B or C form, but rather they regulate the ability of the active enzyme to cleave SREBPs.

DISCUSSION

The current data provide evidence that S1P, like its relatives in the subtilisin superfamily, is synthesized as an inactive precursor that must undergo autocatalytic cleavage in order to become an active protease. The membrane topology of S1P was established by a combination of protease protection assays and protein sequencing experiments. These revealed that S1P contains a 22-amino acid $NH_2$-terminal signal sequence that directs the protein into the lumen of the ER and is cleaved, presumably by signal peptidase, to generate the form designated as S1P-A. S1P-A remains attached to ER membranes by virtue of the hydrophobic membrane anchor sequence near the COOH-terminus. This hydrophobic sequence is followed by a short positively charged sequence that projects into the cytosol.

The first autocatalytic cleavage of S1P occurs at Site-B, which is the Lys-Phe bond in the sequence RSLKF (SEQ ID NO:57). This cleavage removes a 115-residue propeptide from the $NH_2$-terminus of S1P-A. This cleavage does not occur when the active-site serine of S1P is replaced with alanine (S414A mutant), confirming that the cleavage is autocatalytic (FIG. 12). The S414A mutant is not cleaved to the B form even when cells express other copies of active S1P, indicating that S1P-B must be generated by an intramolecular cleavage reaction (FIG. 18). Remarkably, the propeptide is not degraded, but rather it is secreted from the cell. Evidence that the secreted propeptide is the product of cleavage at Site-B comes from three observations: 1) mutagenesis of S1P at Site-B blocked the generation of this peptide (FIG. 15B); 2) the mobility of this peptide on SDS-PAGE is identical to that of a recombinant protein corresponding to amino acids 23–137 of S1P (data not shown); and 3) the secreted propeptide is not digested by PNGase F, indicating that it does not contain N-linked carbohydrate (data not shown). If the propeptide were produced by cleavage at more distal sites, it should contain at least one N-linked sugar chain (see FIG. 14B).

After the propeptide is released by cleavage at Site-B3, S1P-B undergoes further cleavage at Site-C, which is the feu-Arg bond in the sequence RRLLR (SEQ ID NO:22). This clcavage also requires an active S1P enzyme since it, too, is abolished by the S414A mutation (FIG. 12). However, in contrast to Site-B cleavage, the Site-C cleavage reaction can be catalyzed by a nearby S1P enzyme in an intermolecular reaction (FIG. 18).

The processing reaction described in this paper shows some similarities to and some differences from the processing of mammalian furin and the prohormone convertases, which have been studied extensively (for review see (Nakayama, 1997)). Like S1P, these enzymes are initially inserted into the ER lumen by means of a signal sequence, and they are anchored to the membrane by a transmembrane sequence near the COOH-terminus. In the ER, these proteases process themselves intramolecularly to release propeptides of 100–150 amino acids that are similar in length, but not in sequence, to the 115-amino acid propeptide released from S1P (Leduc et al., 1992). In furin, the propeptide remains associated with the enzyme, inhibiting its activity until the enzyme reaches the trans-Golgi network where a second cleavage occurs within the propeptide, allowing it to disassociate from the enzyme, which is thereby activated (Anderson et al., 1997). This second cleavage reaction requires millimolar calcium and acidic pH, conditions that mimic those in the trans-Golgi network (Anderson et al., 1997). In contrast to the findings with furin, our data indicate that the S1P propeptide is not further cleaved, but rather it is secreted intact, as judged by its migration on SDS-PAGE.

After the propeptide is cleaved, S1P-B remains endo H-sensitive, indicating that Site-B cleavage occurs in the ER. It will be important to determine whether the propeptide is released from S1P immediately after cleavage at Site-B, or whether it remains associated, thereby inhibiting the enzyme. The conditions required to release the propeptide must also be elucidated. Our data show that the conversion of S1P-A to S1P-B and S1P-C is not regulated by sterols, but it remains possible that the release of the propeptide from S1P-B is regulated by sterols and that this regulation plays a role in modulating the activity of S1P.

The observations that S1P cleaves itself at an RSLK sequence and that it is capable of cleaving a mutant SREBP-2 with RSLK at the cleavage site broadens the previously determined RXXL consensus to RXX(L/K) (Duncan et al., 1997). This is in contrast to the sequence specificity of furin and the prohormone convertases in which an arginine residue at P1 is essential (Nakayama, 1997). Previous data indicate that S1P cleaves SREBP-2 in a pre-Golgi compartment (Duncan et al., 1997). In these experiments, sites for N-linked glycosylation were introduced into SRFBP-2, and Site-1 cleavage was found to occur when these sugars were still in an endo H-sensitive form (Duncan et al., 1997). This implies that the physiologically active form of S1P should also be endo H-sensitive. The only two forms of S1P that are endo H-sensitive are S1P-A and S1P-B (FIG. 13). S1P-A is inactive, as shown by the loss of cleavage activity when both Site-B and Site-C are mutated (FIG. 16C). Thus, it seems likely that under physiologic conditions, most of the Site-1 cleavage of SREBP-2 is carried out by S1P-B. The inventors believe that the residual activity of the Site-B mutant is attributable to the S1P-C that forms under these conditions (FIG. 15A). In an accompanying paper, the inventors isolate a secreted form of S1P-C and show that it is catalytically active in vitro. If S1P-C is formed in the ER, it must be transported quickly to the Golgi since its carbohydrates are endo H-resistant (FIG. 13). S1P-C may be able to cleave only a small amount of SREBP-2 before it leaves the ER.

S1P differs from furin and the prohormone convertases in one major way, namely, the absolute requirement in vivo for an accessory protein, SCAP (Sukai et al., 1998b). It will be important to determine whether SCAP directly activates S1P, or whether its function is to bring SREBPs to the cellular site that houses active S1P. Recent experiments suggest that SCAP cycles between the ER and Golgi in sterol-deprived cells and that sterols cause SCAP to be retained in the ER (Nohturfft et al., 1998). This finding supports a model in which SCAP escorts SREBPs to a cleavage site that is located in some compartment intermediate between the ER and Golgi where active S1P resides.

Example 11

Generation and Purification of a Soluble, Truncated Form of S1P That Retains its Enzymatic Activity

MATERIALS AND METHODS

The inventors obtained serum-free CHO-S-SFM II medium from Life Technologies (Rockville, Md.); Pefabloc® SC, phenylmethylsulfonyl fluoride (PMSF), (4-amidinophenyl)-methancsulfonyl fluoride (APMSF), leupeptin, and pepstatin from Boehringer Mannheim (Indianapolis, Ind.); N-acetyl-leucinal-leucinal-norleucinal (ALLN) from Calbiochem; and aprotinin and 1,10-phenanthroline from Sigma (St Louis, Mo.). Ac-Ser-Gly-Arg-Ser-Val-Leu-MCA (SEQ ID NO:39) and Boc-Arg-Val-Arg-Arg-MCA (SEQ ID NO:40) were purchased from Peptide International, Inc. (Louisville, Ky.) and Peninsula Laboratories, Inc. (Belmont, Calif.), respectively. Peptides Ac-Val-Phe-Arg-Ser-Leu-Lys-MCA (SEQ ID NO:13), Ac-Val-Phe-Ala-Ser-Leu-Lys-MCA (SEQ ID NO:41), Ac-Val-Phe-Arg-Ser-Arg-Arg-MCA (SEQ ID NO:42), Ac-Ser-Gly-Ser-Gly-Arg-Ser-Val-Leu-MCA (SEQ ID NO:43), Ac-Arg-Ser-Leu-Lys-MCA (SEQ ID NO:18), and Ac-Arg-Ser-Val-Leu-MCA (SEQ ID NO:11) were synthesized by Tularik Inc. (South San Francisco, Calif.) by solution coupling of the appropriate fully deprotected peptide fragment with Lys-MCA, Arg-MCA, or Leu-MCA followed by reverse-phase HPLC purification. Peptides $NH_2$-Arg-Lys-Val-Phe-Arg-Ser-Leu-Lys-Phe-Ala-Glu-Ser-Asp-Pro-Ile-Val-COOH (SEQ ID NO:56) and $NH_2$-His-Ser-Gly-Ser-Gly-Arg-Ser-Val-Leu-Ser-Phe-Glu-Ser-Gly-Ser-Gly-COOH (SEQ ID NO:55) were synthesized in Dallas using standard FMOC solid phase synthesis chemistry on a Rainin Symphony Multiplex Peptide Synthesizer (Washburn, Mass.). IgG-7D4, a mouse monoclonal antibody directed against the $NH_2$-terminal domain of hamster SREBP-2 (amino acids 32–250), was prepared as previously described (Yang et al., 1995). Other materials were obtained from sources described in Example 6.

Construction of Plasmids pCMV-S1P(1052)-Myc-His encodes an 1102-amino acid fusion protein that contains full-length S1P. It consists of an initiator methionine, amino acids 2–1052 of hamster S1P (Sakai et al., 1998b), three novel amino acids (GGR, SEQ ID NO:12) encoded by the sequence of the NotI restriction site, three tandem copies of the 9E10 epitope derived from the human c-Myc protein (EQKLISEEDLGGEQKLISEEDLGPRFEQKLISEEDL, SEQ ID NO:44), five novel amino acids (DMHTG, SEQ ID NO:45) encoded by linker sequences, and six consecutive histidines (yielding a final carboxy terminal fusion sequence of SEQ ID NO:53). Expression is driven by the CMV promoter/enhancer. pCMV-S1P(1052)-Myc-His was constructed in three steps, as follows. First, an intermediate plasmid (no. 1) was constructed by ligation of three DNA fragments: 1) a 5.4-kb fragment released from the BamHI and NotI digestion of pcDNA3 (Invitrogen); 2) a 4-kb fragment released from the EcoRI and NotI digestion pCMV-S1P (Sakai et al., 1998b); and 3) a ~150-bp fragment released from the BamHI and EcoRI digestion of a PCR™-aamplified product obtained from the pCMV-S1P template using the following primers: 5' primer, 5'-CGGGATCCATGAAGCTCATCAACATCTGGC-3' (SEQ ID NO:46); and 3' primer, 5'-GGAGAATTCCACCTTCAAAGTCAGG-3' (SEQ ID NO:47). Second, an intermediate plasmid (no. 2) was constructed by ligation of the following three fragments: a ~5.5-kb fragment released from a BamHI and NotI digestion of pcDNA3.1/Myc-His(+) B (Invitrogen); 2) a 2.6-kb fragment released from a BamHI and NdeI digestion of intermediate plasmid no. 1; and 3) a ~550-bp fragment released from the NdeI and NotI digestion of a PCR™-amplified product obtained from the pCMV-S1P template using the following primers: 5' primer, 5'-TTCAGTACACATCAT ATGGCGTGAACCCTC-3' (SEQ ID NO:48); and 3' primer, 5'-TAGACTCGAGCGGCCGCCCACTGACGGGGT CCTTGGTGGGTGGGTCTG-3' (SEQ ID NO:49). Third, a pair of complementary oligonucleotides (top strand, 5'-GGCCGCGAACAAAAACTCATCTCAGAAGAGGAT CTGGGTGGTGAGCAGAAGTTGATTTICTGAGG AAGACCTGGGCC-3' (SEQ ID NO:50); bottom strand, 5'-CAGGTCTTCCTCAGAAATCAACTTCTGCTCAC CACCCAGATCCTCTTCTGAGATGAGTTTTT GTTCGC-3') (SEQ ID NO:51) were annealed. These oligonucleotides correspond to two additional copies of the c-Myc 9E10 epitope tag. The annealed oligonticleotides were cloned into the ~8-kb fragment released from the ApaI and NotI digestion of intermediate plasmid no. 2. The plasmid resulting from this ligation is designated pCMV-S1P(1052)-Myc-His. pCMV-S1P(983)-Myc-His encodes the same fusion protein as does pCMV-S1P(1052)-Myc-His, except that the DNA encoding the last 69 amino acids of S1P (residues 984 to 1052 of SEQ ID NO:1) was deleted so as to remove the membrane anchor and COOH-terminal tail. The strategy for the construction of this plasmid was similar to that for pCMV-S1P(1052)-Myc-His except for the second step in which a ~300-bp fragment was amplified from pCMV-S1P using the following primers: 3'primer: 5'-TAGACTCGAGCGGCCGCCCTCTTGGTTGTAGC GGCCAGGCATGATCC-3' (SEQ ID NO:52); and the same 5'-primer as described above. All of the PCR™-amplified fragments and ligation junctions in each step of the above constructions were confirmed by DNA sequencing.

Stable Transfection of SRD-12B Cells with Epitope-tagged S1P

On day 0, cholesterol auxotrophic SRD-12B cells were plated at a density of $5\times10^5$ cells/100-mm dish in medium B (Example 6) supplemented with 5% fetal calf serum, 5 $\mu$g/ml cholesterol, 1 mM sodium mevalonate, and 20 $\mu$M sodium oleate. On day 1, cells were transfected with 5 $\mu$g of either pCMV-S1P(1052)-Myc-His or pCMV-S1P(983)-Myc-His using an MBS Kit (Stratagene, La Jolla, Calif.) and cultured overnight in medium B supplemented with 5% fetal calf serum. On day 2, the medium was switched to medium B supplemented with 5% fetal calf lipoprotein-deficient serum without cholesterol. The medium was changed every second day until individual colonies were visible on day 11. Stable expression of S1P-Myc permitted the growth of SRD-12B cells in the absence of sterols (Sakai et al., 1998a). Single cell clones that stably expressed S1P were isolated by limiting dilution and analyzed for S1P expression by immunoblotting with the anti-Myc (9E10 clone) monoclonal antibody. The resulting cell lines expressing S1P(1052)-Myc-His (TR-3109 cells) and S1P(983)-Myc-His (TR-3117 cells) are designated S1P(1052) and S1P(983) cells, respectively.

Purification of S1P(983)-C

Stock cultures of S1P(983) cells were grown in 850-$cm^2$ roller bottles in medium B (Example 6) supplemented with 5% (v/v) newborn calf lipoprotein-deficient serum and 500 $\mu$g/ml G418. On day 0, 10 roller bottles of S1P(983) cells were seeded at a density of $4\times10^7$ Cells/roller bottle. On day 2, the medium was replaced with 100 ml of serum-free medium CHO-S-SFM II. The medium from each roller bottle was collected daily from day 3 to day 7. The collected medium was pooled, filtered through 0.45-$\mu$m cellulose acetate low-protein binding membrane filter units (Corning Costar) and stored at 4° C. for 0 to 4 days. On day 7, the filtered medium was adjusted to pH 8.0 by addition of Tris-HCl at a final concentration of 25 mM, and then loaded onto four parallel 5-ml Ni-NTA agarose columns (Qiagen, Inc., Chatsworth, Calif.) equilibrated with 20 ml of buffer B (25 mM Tris-HCl at pH 8.0, 10% (v/v) glycerol, 1 mM $CaCl_2$). The chromatography was performed at 4° C. via gravity at ~100 ml/hr. The column was washed with 40 ml of buffer B supplemented with 1 M NaCl followed by 20 ml of buffer B without NaCl. Elution was achieved with 15 ml of buffer B containing 250 mM imidazole, pH 8. The eluate was concentrated with a Centriprep 30 filter followed by a Centricon 30 filter (Amicon, Inc., Beverly, Mass.). The concentrated solution was supplemented with an equal volume of 100% glycerol and stored in multiple aliquots at −20° C. without loss of activity for at least 4 months. Ten roller bottles of cells yielded 1 mg protein.

RESULTS

Figure 20A:
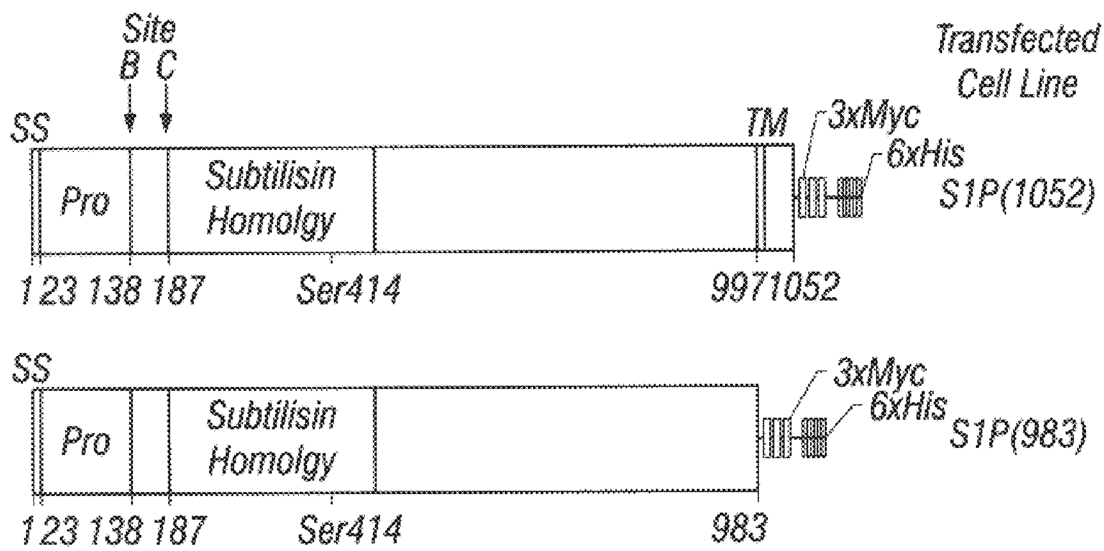
FIG. 20A. The fusion proteins encoded by pCMV-S1P(1052)-Myc-His and pCMV-S1P(983)-Myc-His are shown by the horizontal bars, with the numbers corresponding to the amino acid residues of SEQ ID NO:1. The stable cell lines transfected with these two plasmids are designated as S1P (1052) and S1P(983) cells, respectively. SS denotes signal sequence; Pro denotes the propeptide region of S1P; TM denotes transmembrane domain; Ser414 is the active-site serine residue.

FIG. 20A diagrams the structure of the S1P constructs that were used in these studies. The S1P signal sequence (SS) ends at residue 22. The propeptide cleavage site (Site-B) is after residue 137. Cleavage at this site generates S1P-B. This is followed by a second cleavage after residue 186 to generate S1P-C. The active site serine is at residue 414, and the transmembrane anchor sequence begins at residue 997.

The wild-type protein terminates at residue 1052. The inventors also prepared a cDNA encoding a truncated form of S1P that terminates after residue 983, deleting the transmembrane sequence and the COOH-terminal tail. Numbering of residues is with respect to SEQ ID NO:1. Three copies of a Myc epitope tag and 6 consecutive histidines are added at the COOH-terminus of both proteins (SEQ ID NO:53). cDNAs encoding the proteins illustrated in FIG. 20A were introduced into SRD-12B cells, which lack S1P (Rawson et al., 1998). Permanent cell lines were grown in the absence of cholesterol and oleate, a protocol that selects for cells that express functional S1P. The resulting permanent lines that express full-length and truncated protein are called S1P (1052) and S1P(983), respectively.

Figure 20B:
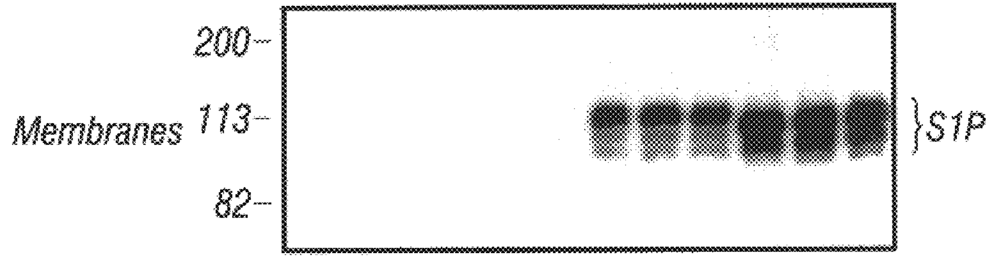
FIG. 20B and FIG. 20C. Immunoblot analysis of the membrane fractions (B) and nuclear (CT) extracts of CHO-7, SRD-12B, S1P(1052), and S1P(983) cells. On day 0, cells were set up for studies at a density of $1\times10^6$ cells/100-mm dish in medium B supplemented with 5% fetal calf serum. On day 2, the cells were switched to medium B containing 5% newborn calf lipoprotein-deficient serum and the indicated addition: none (FIG. 20B and FIG. 20C, lanes 1,4,7,10); 50 μM compactin and 50 μM mevalonate (FIG. 20B and FIG. 20C, lanes 2,5,8,11); 50 μM compactin, 50 μM mevalonate, and a mixture of 1 μg/ml 25-hydroxycholesterol plus 10 μg/ml cholesterol (FIG. 20B and FIG. 20C lanes 3,6,9,12). After incubation for 18 h, the cells were harvested and fractionated as previously described (Sakai et al., 1996).

To quantify expression of the transfected S1P, the cells were homogenized, and a crude membrane pellet was subjected to SDS-PAGE and immunoblotted with an antibody against the Myc tag (FIG. 20B). In order to study the regulation of S1P activity, the inventors incubated the cells in the absence of sterols with or without the HMG CoA reductase inhibitor compactin. S1P is expected to be active under both conditions. The inventors incubated parallel dishes in the presence of compactin plus a mixture of 25-hydroxycholesterol and cholesterol that is known to suppress S1P activity (Sakai et al., 1998a). As expected, membranes from wild-type CHO-7 cells and mutant SRD-12B cells did not contain a protein that reacted with the anti-Myc antibody (FIG. 20B, lanes 1–6). Membranes from the S1P(1052) cells exhibited three bands of immunoreactive protein that corresponded to the sizes expected from S1P-A, -B, and -C (FIG. 20B, lanes 7–9). Membranes from the S1P(983) cells showed two bands that were slightly smaller than the bands in the S1P(1052) cells (FIG. 20B, lanes 10–12). The inventors believe that these represent S1P(983)-A and S1P(983)-B. These proteins were found in the membrane pellet even though they lack a transmembrane anchor. The amounts of the different S1P bands were not altered when the cells were incubated in the presence of compactin plus or minus sterols.

Figure 20C:
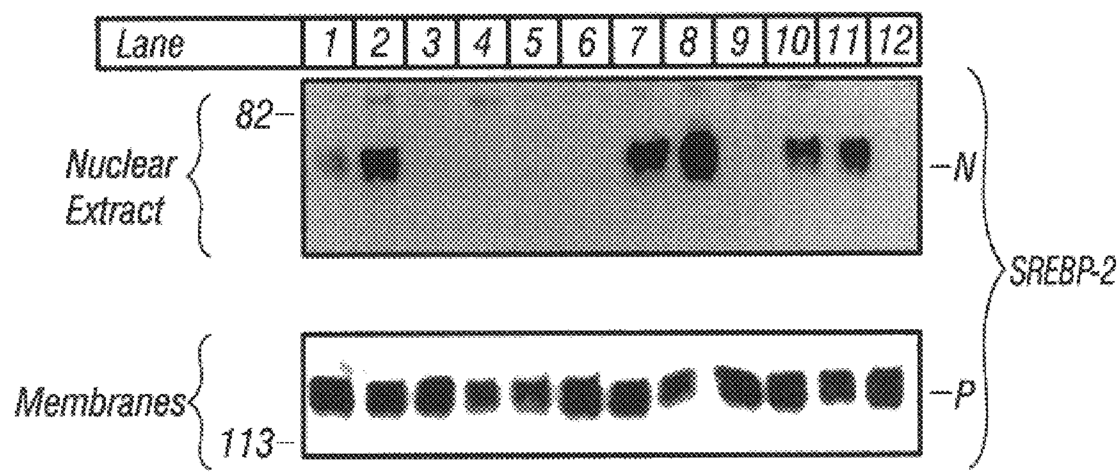

As shown in FIG. 20C, nuclear extracts from CHO-7 cells contained detectable amounts of the $NH_2$-terminal segment of SREBP-2 as determined by immunoblotting when the cells were incubated in the absence of sterols (FIG. 20C, lane 1). The amount was increased when the cells were further deprived of sterols by treatment with compactin (FIG. 20C, lane 2). The band disappeared when the compactin-treated cells were incubated with sterols (FIG. 20C, lane 3). The SRD-12B cells failed to exhibit nuclear SRLBP-2 under any of these conditions (FIG. 20C, lanes 4–6). In the absence of sterols, nuclear SREBP-2 was found in both the S1P(1052) cells and the S1P(983) cells either in the absence or presence of compactin (FIG. 20C, lanes 7,8,10,11). In both cases nuclear SREBP-2 was abolished by addition of sterols (FIG. 20C, lanes 9 and 12). These data indicate that the truncated S1P and the full-length S1P were active and regulated normally by sterols in the transfected cells. The bottom panel of FIG. 20C confirms that membranes from all of the cells contained the precursor form of SREBP-2.

Figure 21A:
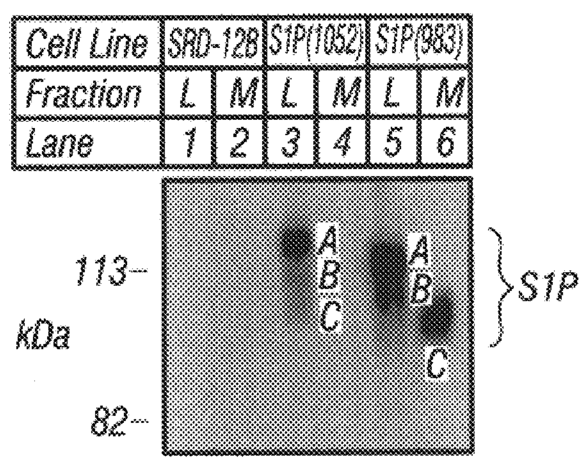
FIG. 21A. Immunoblot analysis of total cell lysate and medium of SRD-12B, S1P(1052), and S1P (983) cells. On day 0, cells were set up for studies at $7\times10^5$ cells/60-mm dish as described in FIG. 20. On day 1, the medium was changed to medium B supplemented with 1% newborn calf lipoprotein-deficient serum. On day 2, the cells were washed and lysed with buffer A as described in the examples above. The medium was treated with cold 80% acetone, and the pellet was resuspended in 1×SDS gel loading buffer. Aliquots of the cell lysate (15 μg protein from 0.1 dish of cells) and the acetone-precipitated proteins from the medium (corresponding to 0.1 dish of cells) were subjected to SDS-PAGE and immunoblotted with 0.5 Vg/ml monoclonal 9E10 anti-Myc antibody. The filter was exposed to film for 1 s. L and M denote cell lysate and medium fractions, respectively. A, B, and C denote three forms of S1P.
Figure 21B:
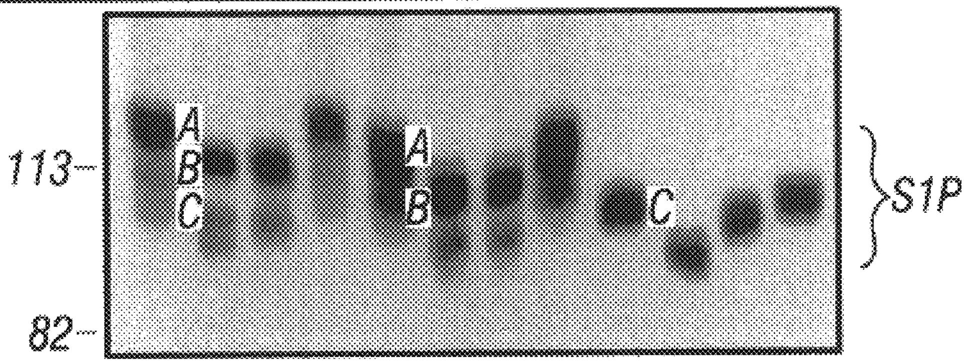
FIG. 21B. Glycosidase treatment of cellular and secreted S1P. Aliquots (10 μl) of total cell lysate and medium fraction (prepared as in FIG. 21A) were boiled and treated with either 0.04 IU of PNGaseF or 0.25 IU of endo H as indicated. The samples were then subjected to SDS-PAGE and immunoblot analysis as described in FIG. 21A. FIG.
Figure 21C:
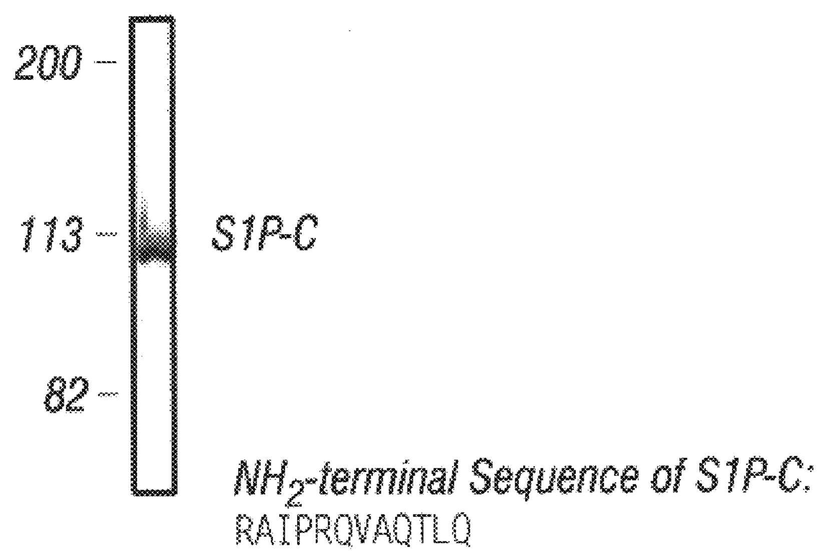
FIGS. 21(A–C). Characterization of S1P(983)-C secreted by S1P(983) cells.

FIG. 21 shows an experiment designed to determine whether the transfected cells secreted S1P and to assess the form of the secreted protein. For this purpose, the cells were incubated in fresh medium for 24 h, after which the medium was removed and the cells were lysed in a detergent buffer. Aliquots of the cell lysate corresponding to 0.1 dish of cells and aliquots of concentrated medium also corresponding to 0.1 dish of cells were subjected to SDS-PAGE and blotted with anti-Myc (FIG. 21A). In the S1P(1052) cells, all imniunoreactive protein was found in the lysate (FIG. 21A , lane 3), and none was in the medium (FIG. 21A, lane 4). The lysate contained three bands corresponding to S1P-A, -B, and -C. In the S1P(983) cells, the lysate contained two bands corresponding to the sizes expected for S1P(983)-A and S1P(983)-B (FIG. 21A, lane 5). The medium contained abundant amounts of a protein corresponding to the expected size of S1P(983)-C (FIG. 21A, lane 6). At the 24 h time point, the total amount of S1P(983)-C in the medium was roughly equal to the amount of S1P(983)-A plus S1P (983)-B in the lysate. Consistent with the findings in the examples, in the S1P(1052) cells, S1P-A, -B, and -C all showed increased mobility after treatment with PNGase F (FIG. 21B, lane 2), indicating that all three forms contain N-linked carbohydrates. Endo H increased the mobility only of S1P-A and S1P-B. Endo H-treated S1P-B overlapped with S1P-C, which was unaffected by endo H (FIG. 21B, lane 3). In lysates from the S1P(983) cells, the A and B forms were both sensitive to endo H as well as to PNGase F. No C form was visible (FIG. 21B, lanes 6 and 7). The medium from these cells contained a protein that corresponded in size to S1P(983)-C (FIG. 21B, lane 9). This protein was sensitive to PNGase F (FIG. 21B, lane 10), but resistant to endo H (FIG. 21B, lane 11). To confirm the identity of this band, the inventors grew the S1P(983) cells in bulk in roller bottles and purified the protein from the medium by nickel affinity chromatography, taking advantage of the 6×His tag. FIG. 21C shows a Coomassie blue stain of an SDS polyacrylamide gel containing this purified protein. A corresponding band was excised from an unstained parallel gel and subjected to Edman degradation, revealing the $NH_2$-terminal sequence shown in FIG. 21C (RAIPRQVAQTLQ, SEQ ID NO:58). This sequence corresponds to the product expected from cleavage at Site-C (see FIG. 14).

Example 12

Development of an In Vitro, Cell-free Assay for S1P

MATERIALS AND METHODS

Fluorogenic Peptide Assay for S1P Activity

S1P activity was measured fluorometrically with MCA-conjugated peptidyl substrates. Each reaction was carried out in 0.2 ml of assay buffer (25 mM Tris, 25 mM Mes, 25 mM acetic acid, and 1 mM $CaCl_2$ adjusted to pH 8.0 with concentrated NaOH). Reactions contained MCA-peptide (final concentration 100 $\mu$M, added in 2 $\mu$l DMSO) and 1.5–5 g of purified S1P(983)-C. After incubation for 0.5–5 h at 37° C., each reaction was terminated by addition of 1 ml of ice-cold 5 mM sodium EDTA. The liberated 7-amino-4-methyl-coumarin (AMC) was measured with a Perkin-Elmer LS-30 luminescence spectrometer (360 nm excitation, 460 nm emission). A standard curve of fluorescence intensity was generated with different concentrations of AMC (Promega).

HPLC Assay for S1P Activity

Each reaction was carried out in a final volume of 40 l of assay buffer (see above) containing a 16-amino acid synthetic peptide (final concentration 300 $\mu$M); and 3 $\mu$g purified S1P(983)-C. After incubation for 4 h at 37° C., the reaction products were separated by reverse-phase HPLC on a 4.6×250-mm RP300 column using a Waters HPLC system. Chromatography was performed in 0.1% (v/v) trifluoroacetic acid at 0.75 ml/min. Elution was achieved with a 50-min gradient of 7–50% (v/v) acetonitrile. Peptide masses were measured by matrix-assisted laser desorption/ionization (MALDI) mass spectrometry using a Voyager DE time-of-flight mass spectrometer from PerSeptive Biosystems (Framingham, Mass.) with α-cyano-4-hydroxycinnamic acid (Aldrich Chemical, Dorset, UK) as the matrix.

RESULTS

To characterize the catalytic activity of the secreted enzyme, the inventors prepared a series of peptides that contain a C-terminal amide of 7-amino-4-methyl-coumarin (AMC) at the COOH-terminus.

Figure 22A:
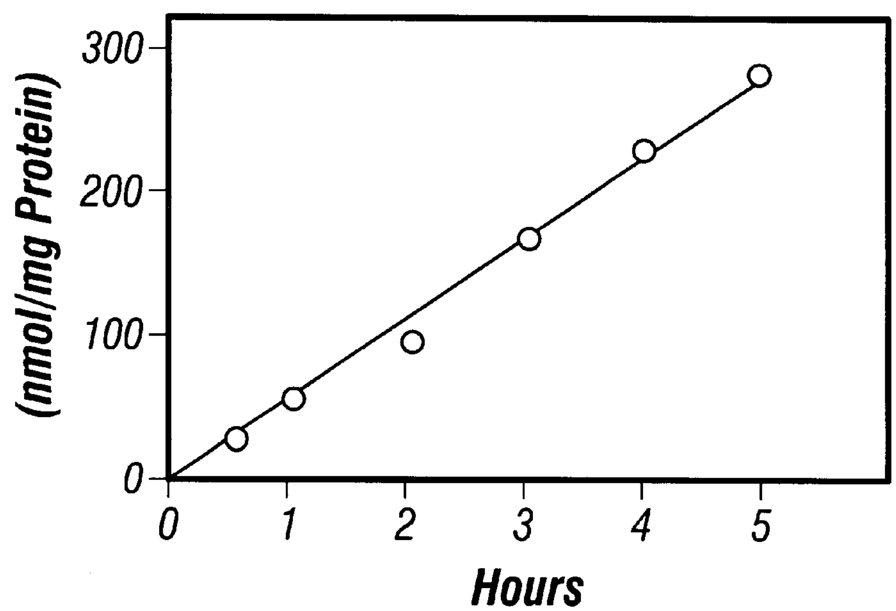
Figure 22B:
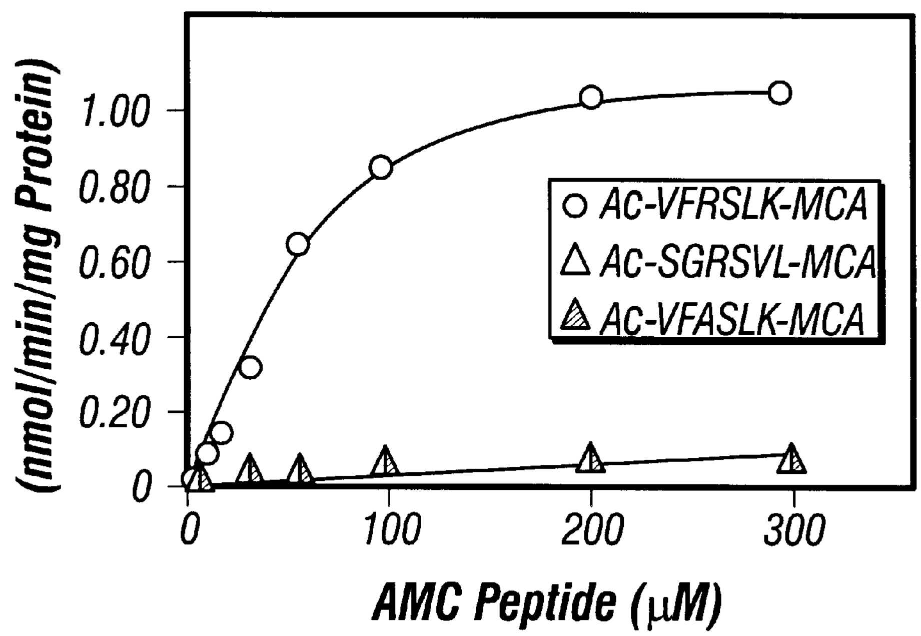
Figures 1, 22B:
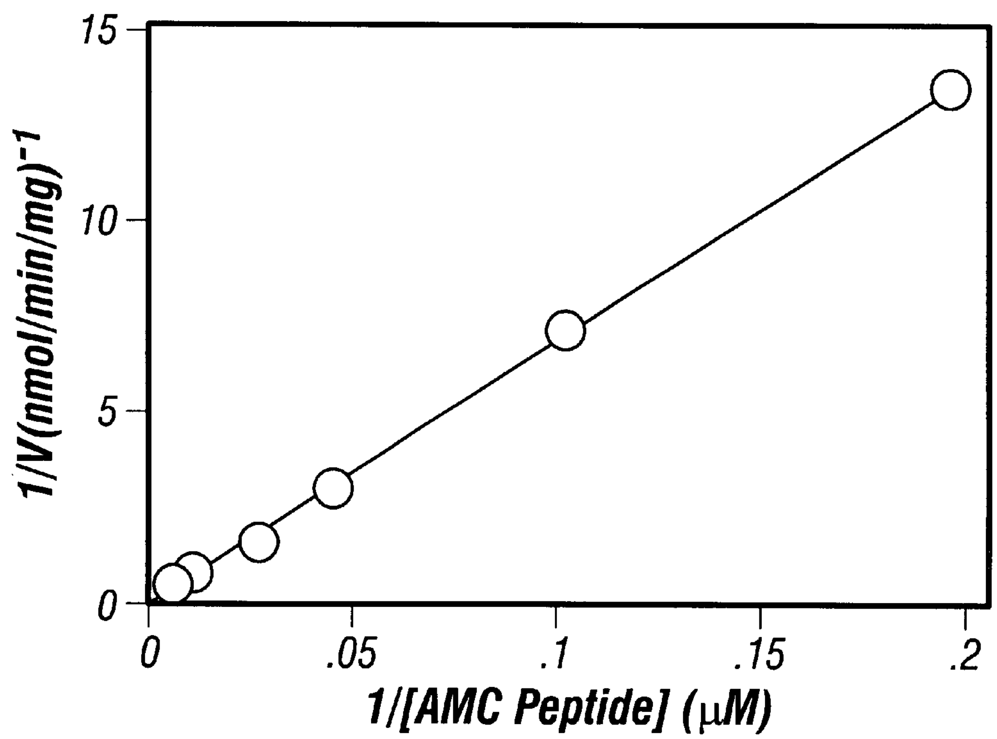
Figure 22C:
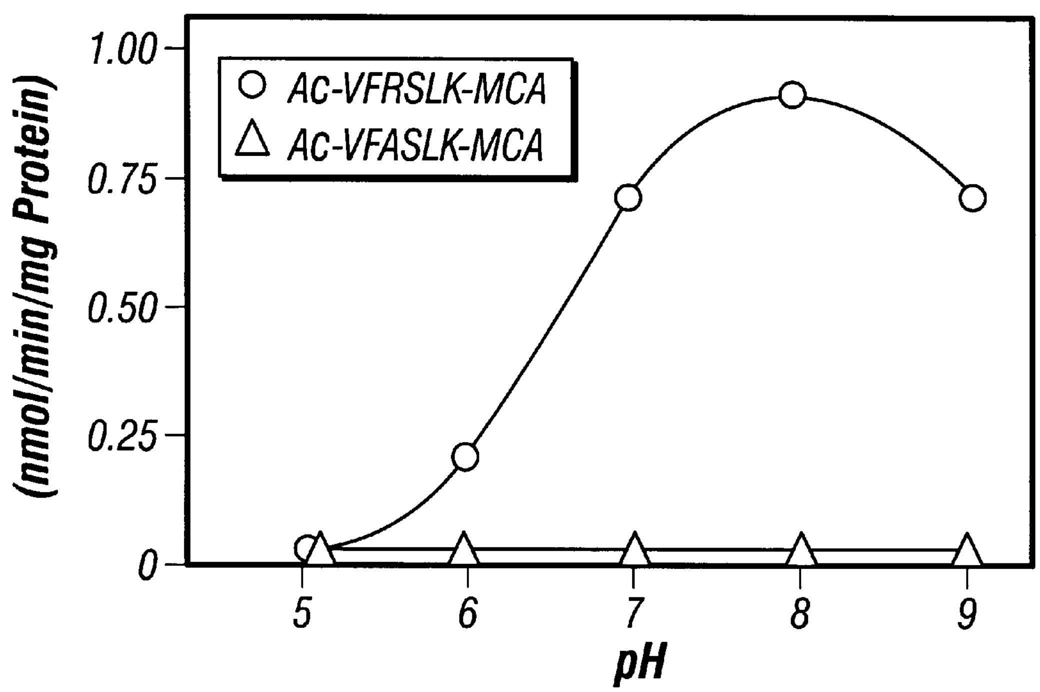

AMC does not show fluorescence at 460 nm unless it has been released from the peptide through proteolysis. Similar substrates have been used to assay furin, prohormone convertases, and other subtilisin-related enzymes (Nakayama, 1997). FIG. 22A shows the fluorescence observed when the peptide Ac-VFRSLK-MCA (SEQ ID NO:13) was incubated with purified secreted S1P(983)-C. The sequence of this peptide corresponds to the sequence at Site-B of S1P, which is known to be cleaved by S1P in an autocatalytic reaction. Fluorescence rose linearly with time for 5 h. FIG. 22B shows a saturation curve with the same substrate performed at the 4-h time point. The inset shows a Iineweaver-Burk plot of these data, which yielded a $K_m$ of 100 $\mu$M and a $V_{max}$ of 1.6 nmol/min/mg protein. The $K_{cat}$ was only 0.16 mol/min/mol of enzyme, which is extremely low, but is sufficient for preliminary characterization. Cleavage was absolutely dependent on the arginine at the P4 position since there was no detectable cleavage of the peptide Ac-VFASLK-MCA (SEQ ID NO:41, FIG. 22B). Surprisingly, the enzyme did not cleave the MCA-peptide corresponding to Site-1 in SREBP-2 (Ac-SGRSVL-NICA, SEQ ID NO:39). The maximal rate of cleavage of Ac-VFRSLK-MCA (SEQ ID NO:13) was observed at pH 8, and there was very little cleavage at pH 6 (FIG. 22C). This differs from the observations with furin and the prohormone convertases, whose pH optima are generally in the range of 6–7 (Nakayama, 1997).

To further explore the recognition requirements for the peptide-MCA assay, the inventors prepared a series of MCA-coupled peptides of varying sequence and incubated them with purified S1P(983)-C. Shortening the Ac-VFRSLK-MCA peptide (SEQ ID NO:13) by two residues reduced its susceptibility to cleavage by about 50% (Table 3). Ac-RSVL-MCA peptides rangring in length from four to eight residues were not cleaved. Importantly, S1P did not cleave MCA peptides that corresponded to the recognition sequence for the prohormone convertases, i.e., Ac-VFRSRR-MCA (SEQ ID NO:42) or Boc-RVRR-MCA (SEQ ID NO:54). The latter peptide has been used for in vitro assays of furin (Molloy et al., 1992).

Like some prohormone convertases (Nakayama, 1997), S1P resisted classic inhibitors of trypsin-like serine proteases, such as PMSF and APMSF (Table 4). It was, however, inhibited by high concentrations of Pefabloc®, which is more water soluble than PMSF. The enzyme was also resistant to leupeptin, pepstatin, aprotinin, and ALLN. It was partially inhibited by EDTA, EGTA, and 1,10-phenantluioline, but only at extremely high concentrations. The same was true of dithiothreitol. The inventors have also demonstrated that the enzyme reaction was not affected by omission of calcium during the purification procedure and in the assay buffer. Moreover, the inventors observed that the reaction was inhibited by calcium concentrations above 3 mM.

TABLE 3

Comparative cleavage of fluorogenic synthetic peptidyl substrates by purified S1P(983)-C

| Substrate | SEQ ID NO's | Relative Activity |
|---|---|---|
| Ac-VFRSLK-MCA | SEQ ID NO:13 | 1.0 |
| Ac-RSLK-MCA | SEQ ID NO:18 | 0.47 |
| Ac-VFASLK-MCA | SEQ ID NO:41 | <0.1 |
| Ac-SGRSVL-MCA | SEQ ID NO:39 | <0.1 |
| Ac-SGSGRSVL-MCA | SEQ ID NO:43 | <0.1 |
| Ac-RSVL-MCA | SEQ ID NO:11 | <0.1 |
| Ac-VFRSRR-MCA | SEQ ID NO:42 | <0.1 |
| Boc-RVRR-MCA | SEQ ID NO:40 | <0.1 |

The indicated fluorogenic peptide-MCA (100 $\mu$M) was incubated with 3 $\mu$g of purified S1P(983)-C at 37° C. for 5 h. The S1P activity of Ac-VFRSLK-MCA (SEQ ID NO:13, 930 pmol per min/mg protein) was set at 1.0, and the activity of the other substrates was expressed relative to this value. Each value represents the average of duplicate incubations, which varied from each other by <10%.

TABLE 4

S1P(983)-C mediated cleavage of Ac-VFRSLK-MCA: Effect of protease inhibitors

| Addition | Concentration mM | AMC Liberated pmol/tube | AMC Liberated % control |
|---|---|---|---|
| None | — | 839 | 100 |
| Pefabloc ® | 1 | 731 | 87 |
| | 3 | 366 | 44 |
| | 10 | 60 | 7 |
| PMSF | 1 | 853 | 102 |
| | 10 | 690 | 82 |
| APMSF | 1 | 793 | 95 |
| PMSF/APMSF | 10/1 | 745 | 89 |
| Leupeptin | 1 | 754 | 90 |
| Pepstatin | 0.01 | 798 | 95 |
| Aprotinin | 0.0003 | 745 | 89 |
| ALLN | 0.1 | 811 | 97 |
| EDTA | 3 | 802 | 96 |
| | 30 | 303 | 36 |
| EGTA | 3 | 609 | 73 |
| | 30 | 305 | 36 |
| 1,10-Phenanthroline | 3 | 361 | 43 |
| | 10 | 253 | 30 |
| EDTA/EGTA/ 1,10-Phenanthroline | 3/3/3 | 163 | 19 |
| Dithiothreitol | 0.1 | 615 | 73 |
| | 1 | 323 | 38 |
| | 10 | 99 | 12 |

Aliquots of the fluorogenic peptide Ac-VFRSLK-MCA (SEQ ID NO:13, 100 $\mu$M) were incubated with 3 $\mu$g of purified S1P(983)-C in the absence or presence of the indicated addition at 37° C. for 5 hours. Each value represents the average of duplicate calculations, which varied from each other by <10%.

The low activity of the purified S1P raised the possibility that the true activity might be attributable to a trace amount of a more active contaminating enzyme that could not be visualized on the Coomassie-stained gels. To rule out this possibility, the inventors performed an immunoprecipitation study (FIG. 23). Purified S1P(983)-C was incubated with agarose beads containing a control antibody or anti-Myc. After centrifugation the supernatant and pellet fractions were subjected to SDS-PAGE and blotted with anti-Myc. As shown in FIG. 23A, anti-Myc, but not the control antibody, precipitated the S1P(983)-C. The supernatant and pellet fractions were also assayed for the ability to cleave Ac-VFRSLK-MCA (SEQ ID NO:13, FIG. 23B). When the material was treated with a control antibody, the enzyme activity was in the supernatant. When anti-Myc was used, the activity was all found in the pellet. These data demonstrate that the cleavage of the peptide substrate in this assay is due to the activity of S1P(983)-C.

The failure of S1P(983)-C to cleave the RSVL-MCA peptides (SEQ ID NO:11) might have been due to an inability of the enzyme to recognize the RSVL sequence (SEQ ID NO:11), or alternatively it might be due to the resistance of the peptide-MCA bond to cleavage. To distinguish between these possibilities, the inventors prepared 16-residue peptides composed of the amino acids surrounding the internal cleavage Site-B in S1P (i. e., RSLK, SEQ ID NO:18) or Site-1 in SREBP-2 (i. e., RSVL, SEQ ID NO:11). The peptides were incubated with or without purified S1P (983)-C, and the products were separated by HPLC. In the absence of S1P, both peptides gave single predominant peaks on the HPLC (FIGS. 5A and 5C). After incubation with S1P(983)-C, these peptides were each cleaved to generate two smaller peptides (FIGS. 5B and 5D). These peptides were examined by mass spectroscopy and the sequences were found to correspond to those predicted from cleavage after RSLK and RSVL, respectively. Thus, S1P (983)-C has the potential to cleave Site-1 in SREBP-2.

DISCUSSION

The current studies demonstrate that a secreted, truncated form of S1P is able to cleave peptide substrates corresponding to Site-1 in SREBP-2 and to the internal propeptide cleavage site within S1P itself. The characteristics of these in vitro reactions differed importantly from the activities previously observed for furin and the prohormone convertases, which are the only subtilisin-like enzymes previously characterized in animal cells.

The studies of secreted S1P were facilitated by the use of SRD-12B cells, whose auxotrophic growth requirements could be overcome by expression of S1P, even when the protein was truncated so as to delete the membrane-spanning and cytosolic domains. After transfecting SRD-12B cells with expression vectors encoding truncated S1P, the inventors were able to select for high-level expression by growing the cells in the absence of cholesterol, oleate, and mevalonate. After incubation of the cells for 5 days in lipoprotcin-deficient medium, the concentration of truncated S1P reached approximately 0.2 mg/liter in the extracellular fluid. The protein contained a hexahistidine tag that allowed purification by nickel affinity chromatography.

Following cleavage by signal peptidase, the S1P proenzyme, designated S1P-A, undergoes two further cleavages to generate S1P-B and S1P-C. Studies with mutant forms of S1P suggests that S1P-A is inactive and that S1P-B is responsible for most of the physiologically relevant cleavage of SREBPs. S1P-C, although catalytically active, may not cleave SREBPs within cells. This conclusion follows from studies performed with cells transfected with cDNAs encoding altered forms of SREBP-2 that contain N-linked glycosylation sites in the luminal loop (Duncan et cl, 1997). These studies show that SREBP-2 is cleaved when the N-linked sugars are still in the endo H-sensitive form, i.e., before the protein has reached the Golgi apparatus. The carbohydrates on S1P-A and S1P-B are also in the endo Insensitive form, indicating that these enzymes are potentially in the same compartment as the substrate SREBPs. In contrast, the carbohydrates on S1P-C are in the endo H-resistant form, indicating that S1P-C is either formed in the Golgi, or else it is transported to the Golgi immediately after it is formed. In either event, most of the S1P-C is not in the compartment where SREBP cleavage takes place.

In the current studies, the inventors found that S1P (983)-C was the only form of truncated S1P that was secreted from transfected cells. Truncated S1P(983)-A and S1P(983)-B were found only within the cells (FIG. 21). These proteins were bound to membranes, even though they lacked membrane anchors. These data suggest that S1P (983)-A and S1P(983)-B contain a sequence that allows them to bind to a membrane protein that retains them in a pre-Golgi compartment. S1P may move to the Golgi only after cleavage at Site-C. A precedent for this finding is observed in the case of furin, where the precursor is retained in a pre-Golgi compartment by a saturable mechanism, which has been suggested to consist of binding to the ER protein calnexin (reviewed in (Nakayama, 1997)). A similar mechanism may be responsible for the retention of S1P-A and S1P-B since immunoprecipitation studies demonstrated that calnexin was brought down from cell extracts by an antibody against epitope-tagged S1P.

Even after the propeptide cleavage reaction has taken place, furin remains inactive because the propeptide remains attached to the enzyme in a noncovalent manner. Furin becomes active only after it reaches an acidic compartment where a further cleavage occurs within the propeptide, allowing its release from the enzyme (Nakayama, 1997). The inventors do not yet know whether the propeptide dissociates from S1P immediately after cleavage at Site-B, or whether it remains attached until some subsequent event occurs.

Although secreted S1P(983)-C had definite catalytic activity toward peptide-MCA conjugates, the rate of cleavage was very slow. The maximal $K_{cat}$ was only 0.16 mol/min per mol of enzyme. This is about one-tenth the value observed by others for furin in a similar assay (1.6 mol/min per mol of enzyme (Molloy et al., 1992)). One reason for this low activity may be the absence of SCAP in the in vitro assay. SCAP binds to SREBPs and is required for Site-1 cleavage in intact cells (Sakai et al., 1998a). S1P differs from furin and the other prohormone convertases in its absolute requirement for SCAP in vivo (Sakai et al., 1998b; Sakai et al., 1998a). The inventors do not know whether SCAP directly activates S1P or whether its only function is to transport SREBPs to the cellular compartment that contains S1P. If SCAP does activate the enzyme, then the inventors may not be able to achieve full enzymatic activity in vitro until the inventors find some way to add purified SCAP into the assay. SCAP interacts with SREBPs primarily on the cytoplasmic side of the membrane through the binding of the WD-repeat segment of SCAP to the COOH-terminal regulatory segment of SREBPs (Sakai et al., 1997). In order to achieve this interaction in vitro, it may be necessary to use full-length SREBP as substrate.

The in vitro peptide cleavage assays revealed several additional aspects in which S1P differs from furin and the prohormone convertases. In addition to the difference in pH optimum furin has an absolute requirement for calcium, and it is totally inhibited by EDTA (Nakayama, 1997, Molloy et al., 1992). S1P did not require calcium in the assay medium, and it was only weakly inhibited by high concentrations of calcium chelators. This difference may rclate to the difference in the compartments in which the two enzymes act. Furin acts in the distal Golgi apparatus and in secretory vesicles where the pH is acidic and the calcium concentration is high. S1P is believed to act in a pre-Golgi compartment which is likely to have a neutral pH and a low calcium concentration.

Purified S1P is also distinctive in its ability to cleave MCA peptides with lysine at the P1 position. Furin and all the known prohormone convertases have an absolute requirement for arginine at the P1 position, and lysine cannot substitute for this arginine (Nakayama, 1997). In contrast. S1P cleaves itself after the lysine of the RSLK sequence (SEQ ID NO:18) to generate the propeptide. S1P also cleaves RSLK-MCA peptide (SEQ ID NO:18) in vitro, but it does not cleave RVRR-MCA (SEQ ID NO:54), which is a classic furin substrate (see Table 2 in (Nakayama, 1997)).

Purified S1P did not cleave the RSVL-MCA peptide (SEQ ID NO:11), which corresponds to Site-1 in SREBP-2, but it did cleave this sequence when it was located at the center of a 16-residue peptide representing the SREBP-2 sequence (SEQ ID NO:55). It is possible that the presence of the MCA group reduces the affinity of S1P for MCA-conjugated peptides when leucine, in contrast to lysine, is at the P1 position. These observations are consistent with the recent report by Seidab et al. (Seidah et al., 1999), who described the cloning of a human subtilisin-related cDNA, called SKI-1, which is identical to S1P. These authors stated that they had obtained preliminary data showing that culture medium from cells infected with a recombinant vaccina virus encoding full-length SKI-1 was unable to cleave the RSVL-MCA peptide (SEQ ID NO:11), but was able to cleave the RSVLS sequence when it was contained in a 27-amino acid synthetic peptide corresponding to the luminal loop sequence of human SREBP-2 (SEQ ID NO:57).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

WO 09/15637

WO 89/01967

WO 90/02580

WO 91/09939

WO 91/10425

WO 91/10470

WO 95/29989

WO 97/26321

WO 97/26334

Akusjarvi, Svensson, Nygard, *Mol. Cell. Biol.*, 7:549–551, 1987.

Anderson, VanSlyke, Thulin. Jean, Thomas, *EMBO*, 16:1508–1518, 1997.

Blobel, "Intracellular protein topogenesis," *Proc. Natl. Acad. Sci. USA*, 77:1496–1500, 1980.

Brown and Goldstein, "The SREBP pathway: Regulation of cholesterol metabolism by proteolysis of a membrane-bound transcription factor," *Cell*, 89:331–340, 1997.

Cao, Goldstein, Brown, "Complementation of mutation in acyl-CoA: cholesterol acyltransferase (ACAT) fails to restore sterol regulation in ACAT-defective sterol-resistant hamster cells," *J. Biol. Chem.*, 271:14642–14648, 1996.

Chen, Andres, Goldstein, Russell, Brown, cDNA cloning and expression of the peptide-binding, β subunit of rat p21$^{ras}$ farnesyltransferase, the counterpart of yeast DPR1/RAM1," *Cell*, 66:327–334, 1991.

Cullen and Malim, "Secreted placental alkaline phosphatase as a eukaryotic reporter gene," *Meth. Enzymol.*, 216:362–368, 1992.

Devereux, Haeberli, Smithies, "A comprehensive set of sequence analysis programs for the VAX," *Nucl. Acids Res.*, 12:387–395, 1984.

Duncan, Brown, Goldstein, Sakai, "Cleavage site for sterol-regulated protease localized to a Leu-Ser bond in lumenal loop of sterol regulatory element binding protein-2," *J. Biol. Chem.,* 272:12778–12785, 1997.

Duncan, Dave, Sakai, Goldstein, Brown, "Second-site cleavage in sterol regulatory element-binding protein occurs at transmembrane junction as determined by cysteine panning," *J. Biol. Chem.*, 273: 17801–17809, 1998.

Goldstein, Basu, Brown, "Receptor-mediated endocytosis of LDL in cultured cells," *Meth. Enzymol.*, 98:241–260, 1983.

Harlow and Lane, *Antibotlies: A Laboratory Manual*, Cold Spring Harbor Laboratory, New York, 1988.

Hasan, Chang, Chang, "Somatic cell genetic biochemical characterization of cell lines resulting from human genomic DNA transfections of Chinese hamster ovary cell mutants defective in sterol-dependent activation of sterol synthesis and LDL receptor expression," *Somatic Cell Mol. Genet.*, 20:183–194, 1994.

Hebert, Simons, Peterson, Helenius, *Cold Spring Harbor Symp. Quant. Biol.*, 60:405–415, 1995.

Hua, Nohturfft, Goldstein, Brown, "Sterol resistance in CHO cells traced to point mutation in SREBP cleavage activating protein (SCAP)," *Cell*, 87:415–426, 1996a.

Hua, Sakai, Brown, Goldstein, "Regulated cleavage of sterol regulatory element binding proteins (SREBPs) requires sequences on both sides of the endoplasmic reticulum membrane," *J. Biol. Chem.*, 271:10379–10384, 1996b.

Hua, Sakai, Ho, Goldstein, Brown, "Hairpin orientation of sterol regulatory element binding protein-2 in cell membranes as determined by protease protection," *J. Biol. Chem.*, 270:29422–29427, 1995.

Kornfeld and Kornfeld, "Assembly of asparagine-linked oligosaccharides," *Ann. Rev. Biochem.*, 54:631–664, 1985.

Kunkel, Roberts, Zakour, "Rapid and efficient site-specific mutagenesis without phenotypic selection," *Meth. Enzymol.*, 154:367–382, 1987.

Kyte and Doolittle, "A simple method for displaying the hydropathic character of a protein," *J. Mol. Biol.* 157:105–132, 1982.

Laemmli, *Nature*, 227:680–685, 1970.

Leduc, Molloy, Thorne, Thomas, *J. Biol. Chem.*, 267:14304–14308, 1992.

Leibrock, Lottspeich, Hohn, Hofer, Hengerer, Masiakowski, Thoenen, Barde, *Nature*, 341:149–152, 1989.

Loftus, Morris, Carstea, Gu, Cummings, Brown, Ellison, Ohno, Rosenfeld, Tagle, Pentchev, Pavan, "Murine model of Niemann-Pick C disease: Mutation in a cholesterol homeostasis gene," *Science*, 277:232–235, 1997.

Marshall, "Glycoproteins," *Annu. Rev. Biochenm.*, 41:673–702, 1972.

Metherall, Goldstein, Luskey, Brown, "Loss of transcriptional repression of three sterol-regulated genes in mutant hamster cells," *J. Biol. Chem.*, 264:15634–15641, 1989.

Molloy, Bresnahan, Leppla, Klimpe, Thomas, *J. Biol. Chem.* 267:16396–16402, 1992.

Nagase, Miyajima, Tanaka, Sazuka, Seki, Sato, Tabata, Ishikawa, Kawarabayasi, Kotani, Nomura, *DNA Research*, 2:37–43, 1995.

Nakayama, "Furin: a mammalian subtilisin/Kex2p-like endoprotease involved in processing of a wide variety of precursor proteins," *Biochem. J.*, 327:625–635, 1997.

Nohturfft, Brown, Goldstein. "Topology of SREBP cleavage-activating protein, a polytopic membrane protein with a sterol-sensing domain," *J. Biol. Chem.*, 273:17243–17250. 1998a.

Nohturfft, Brown, Goldstein, *Proc. Nat. Acad. Sci. USA*, 95:12848–12853, 1998b.

Nohturfft, Hua, Brown, Goldstein, "Recurrent G-to-A substitution in a single codon of SREBP cleavage-activating protein causes sterol resistance in three mutant CHO cell lines," *Proc. Natl. Acad. Sci. USA*, 93:13709–13714, 1996.

Rawson, Cheng, Brown, Goldstein, "Isolation of cholesterol-requiting mutant CHO cells with defects in cleavage of sterol regulatory element binding proteins at Site-1*,*" *J. Biol. Chem.*, 273:28261–28269, 1998.

Rawson, Zelenski, Nijhawan, Ye, Sakai, liasan, Chang, Brown, Goldstein, "Complementation cloning of S2P, a gene encoding a putative metalloprotease required for intramembrane cleavage of SREBPs," *Molecular Cell*, 1:47–57, 1997.

Rosenfeld, Zeni, llaniu, Talvenheimno, Radka, Bennctt, Miller, Welcher, *Prot. Er. Pur.*, 6:465–471, 1995.

Sakai, Duncan, Rawson, Hua, Brown, Goldstein, "Sterol-regulated release of SREBP-2 from cell membranes requires two sequential cleavages, one within a transmembrane segment," *Cell*, 85:1037–1046, 1996.

Sakai, Nohturfft, Cheng, Ho, Brown, Goldstein, "Identification of complexes between the COOH-terminal domains of sterol regulatory element binding proteins (SREBPs) and SREBP Cleavage-Activating Protein (SCAP)," *J. Biol. Chem.*, 272:20213–20221, 1997.

Sakai, Nohturfft, Goldstein, Brown, "Cleavage of sterol regulatory element binding proteins (SREBPs) at site-1 requires interaction with SREBP cleavage-activating protein. Evidence from in vivo competition studies," *J. Biol. Chem.*, 273:5785–5793, 1998a.

Sakai, Rawson, Espenshade, Cheng, Seegmiller, Goldstein, Brown, *Mol. Cell*, 2:505–514, 1998b.

Sambrook, Fritsch, Maniatis, *In: Molecuilar Cloning: A Laboratory Manual*, Cold Spring Harbor Laboratory Press, New York, pp?, 1989.

Sanger, Coulson, Barrell, Smith, Roe, "Cloning in single-stranded bacteriophage as an aid to rapid DNA sequencing," *J. Mol. Biol.*, 143:161–178. 1980.

Seidah, Mowla, Hamelin, Mamarbachi, Benjannet, Touré, Basak, Munzer, Marcinkiewicz, Zhong, Barale, Lazure, Murphy, Chrétien, Marcinkiewicz, *Proc. Natl. Acad. Sci. USA*, 96:1 321–1326, 1999.

Siezen and Leunissen, "Subtilases: The superfamily of subtilisin-like serine proteases," *Prot. Sci.*, 6:501–523, 1997.

Sørensen, Bech, Meldal, Breddam, *Biochem.*, 32:8994–8999, 1993.

Tolleshaug, Goldstein, Schneider, Brown, *Cell*, 30:715–724, 1982.

Usdin et al., "Gastric inhibitory peptide receptor, a member of the secretin-vasoactive intestinal peptide receptor family, is widely distributed in peripheral organs and the brain," *Endocrinology*, 133:2861–2870, 1993.

van Wezel, "Growth of cell-strains and primary cells on microcarriers in homogeneous culture," *Nature*, 216:64–65, 1967.

von Heijne, "Signal sequences. The limits of variation," *J. Mol. Biol.*, 184:99–105, 1985.

Von Melchner, Reddy, and Ruley, "Isolation of cellular promoters by using a retrovirus promoter trap," *Proc. Natl. Acad. Sci. U.S.A.*, 87:3733–3737, 1990.

Waeber et al., "Characterization of the murine high $K_m$ glucose transporter GLUT-2 gene and its transcriptional regulation by (glucose in a differentiated insulin-secreting cell line," *J. Biological Chemistry*, 43:26912–26919, 1994.

Wagner et al., *Science*, 260:1510–1513, 1990.

Walsh et al., "Phenotypic correction of Fanconi anemia in human hematopoietic cells with a recombinant adeno-associated virus vector," *Proc. Natl. Acad. Sci. USA*, 89:7257–7261, 1994;

Wang, Sato, Brown, Hua, Goldstein, *Cell*, 77:53–62, 1994.

Wei et al., "Expression of the human glucocerebrosidase and arylsulfatase A genes in murine and patient primary fibroblasts transduced by an adeno-associated virus vector," *Gene Therapy*, 1:261–268, 1994.

Welsh, Claesson-Welsh, Hallberg, Welsh, Betsholtz, Arkhammar, Nilsson, Heldin and Berggren, *Proc. Natl. Acad. Sci. USA* 87(15):5807–5811, 1990.

Welsh, Welsh, Nilsson, Arkammar, Pepinsky, Steiner and Berggren, *Proc. Natl. Acad. Sci. USA* 85:116–120, 1987.

Whitesell et al., "Transport and metabolism of glucose in an insulin-secreting cell line, BetaTC-1*,*" *Biochemistry*, 30:11560–11566, 1991.

Wong et al., "Appearance of β-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Wyborski and Short, "Analysis of inducers of the *E. coli* lac repressor system in mammalian cells and whole animals," *Nucleic Acids Res.*, 19(17):4647–53, 1991.

Yang et al., "Cellular immunity to viral antigens limits E1-deleted adenoviruses for gene therapy," *P.N.A.S. USA*, 91:4407–4411, 1994.

Yang et al., "In vivo and in vitro gene transfer to mammalian somatic cells by particle bombardment," *Proc. Nat'l Acad. Sci. USA*, 87:9568–9572, 1990.

Yang, Brown, Ho, Goldstein, *J. Biol. Chem.*, 270:12152–12161, 1995.

Yoder, Kang, Zhou, Luo, and Srivastava, "In vivo gene transfer in murine hematopoietic reconstituting stem cells mediated by the adeno-associated virus 2-based vectors," *Blood*, 82 (Supp.): 1:347A, 1994.

Zawalich et al., "Regulation of insulin release by phospholipase C activation in mouse islets: differential effects of glucose and neurohormonal stimulation", *Endocrinology* 136:4903–4909, 1995.

Zawalich, W. S., "Regulation of insulin secretion bv phosphoinositide-specific phospholipase C and protein kinase C activation", *Diabetes Rev*, 4:160–176, 1996.

Zhang, et al., "Insulin secretion and cAMP metabolism in HIT cells. Reciprocal and serial passage-dependent relationships", Diabetes, 38(1):44–8, 1989.

Zhou et al, "Induction by leptin of uncoupling protein-2 and enzymes of fatty acid oxidation", *Proc Natl Acad Sci USA*, 94(12):6386–90, 1997.

Zhou et al., "Adeno-associated virus 2 mediated gene transfer in murine hematopoietic cells, *Exp. Hematol.* (N.Y.), 21:928–933, 1993.

Zhou et al., "Adeno-associated virus 2-mediated high efficiency gene transfer into immature and mature subsets of hematopoietic progenitor cells in human umbilical cord blood," *J.Exp.Med.*, 179:1867–1875, 1994.

What is claimed is:

1. A method of identifying and preparing a modulator of Site-1 protease activity comprising the steps of:

a) identifying a cell that expresses a Site-1 protease comprising the amino acid sequence set forth in Seq. Id. No. 1 or Seq. Id. No. 3;

b) contacting said cell with a candidate modulator in vitro;

c) monitoring said cell for an effect that is not present in the absence of said candidate modulator; and d) formulating a composition comprising said candidate modulator.

2. The method of claim 1, wherein said Site-1 protease is encoded by a transgene comprising the nucleotide sequence of Seq. Id. No. 2.

3. The method of claim 1, wherein the Site-1 protease is encoded by a transgene comprising the nucleotide sequence of Seq. Id. No. 4.

4. The method of claim 1, wherein said effect is cholesterol biosynthesis, fatty acid biosynthesis, or lipid uptake.

5. The method of claim 1, wherein said cell is a mammalian cell.

6. The method of claim 5, wherein said mammalian cell is a human cell, a hamster cell, a cow cell, a goat cell, a sheep cell, a rat cell, or a mouse cell.

7. The method of claim 6, wherein the mammalian cell is a hamster cell.

8. The method of claim 6, wherein the mammalian cell is a human cell.

9. A method for preparing a modulator of Site-1 protease comprising the steps of:

a) preparing a reaction mixture comprising an isolated and purified Site-1 protease comprising the amino acid sequence set forth in Seq. Id. No. 1 or Seq. Id. No. 3, and a target molecule comprising a Site-1 protease cleavage site;

b) mixing a candidate modulator with said reaction mixture in vitro;

c) identifying a modulator by monitoring the cleavage of said target molecule in the presence of said candidate modulator relative to the cleavage of said target molecule in the absence said candidate modulator; and d) preparing a composition comprising a modulator identified in step (c).

10. The method of claim 9, wherein said reaction mixture further comprises a sterol regulatory element binding protein (SREBP) cleavage activating protein.

11. The method of claim 9, wherein said target molecule is an SREBP.

12. A method for preparing a modulator of Site-1 protease activity comprising the steps of:

a) providing a cell that expresses a Site-1 protease comprising the amino acid sequence of Seq. Id. No. 1 or Seq. Id. No. 3, wherein said cell comprises a transgene encoding a fusion protein that comprises a reporter polypeptide and a polypeptide comprising a Site-1 protease target sequence, and wherein said transgene is operably linked to a promoter and is expressed; b) contacting said cell with a candidate modulator in vitro; c) identifying a modulator by monitoring the activity of said Site-1 protease by detecting said reporter polypeptide; and d) preparing a composition comprising a modulator identified in step (c).

13. The method of claim 12, wherein said fusion protein comprising a Site-1 protease target sequence is a sterol regulatory element binding protein (SREBP).

14. The method of claim 12, wherein said cell further comprises a transgene encoding an SREBP cleavage activating protein.

15. The method of claim 12, wherein said reporter polypeptide comprises a transit peptide.

16. The method of claim 15, wherein said transit peptide directs excretion of said reporter polypeptide following cleavage of said Site-1 protease target sequence by said Site-1 protease.

17. The method of claim 15, wherein said monitoring comprises detecting said reporter polypeptide in culture media in which said cell is grown.

18. The method of claim 12, wherein said cell does not express an endogenous, wild-type Site-1 protease and said Site-1 protease is provided by expression of a transgene encoding the amino acid sequences set forth in Seq. Id. No. 1 or Seq. Id. No. 3.

19. The method of claim 12, wherein said cell is a prokaryotic cell.

20. The method of claim 12, wherein said cell is a eukaryotic cell.

21. The method of claim 20, wherein said the eukaryotic cell is a mammalian cell.

22. The method of claim 21, wherein said mammalian cell is a human, hamster, rat, or mouse cell.

23. The method of claim 22, wherein said mammalian cell is a hamster cell.

24. The method of claim 22, wherein said mammalian cell is a human cell.

25. The method of claim 12, wherein said reporter polypeptide is visually detectable.

26. The method of claim 12, wherein said reporter polypeptide is immunologically detectable.

27. The method of claim 12, wherein the reporter polypeptide is an enzyme.

28. The method of claim 27, wherein said enzyme is alkaline phosphatase.

* * * * *

SEQUENCE LISTING

<160> NUMBER OF SEQ ID NOS: 60

<210> SEQ ID NO 1
<211> LENGTH: 1052
<212> TYPE: PRT
<213> ORGANISM: Cricetulus griseus

<400> SEQUENCE: 1

Met Lys Leu Ile Asn Ile Trp Leu Leu Leu Leu Val Val Leu Leu Cys
1 5 10 15

Gly Lys Lys His Leu Gly Asp Arg Leu Gly Lys Lys Ala Phe Glu Lys
20 25 30

Ala Ser Cys Pro Ser Cys Ser His Leu Thr Leu Lys Val Glu Phe Ser
35 40 45

Ser Thr Val Val Glu Tyr Glu Tyr Ile Val Ala Phe Asn Gly Tyr Phe
50 55 60

Thr Ala Lys Ala Arg Asn Ser Phe Ile Ser Ser Ala Leu Lys Ser Ser
65 70 75 80

Glu Val Asp Asn Trp Arg Ile Ile Pro Arg Asn Asn Pro Ser Ser Asp
85 90 95

Tyr Pro Ser Asp Phe Glu Val Ile Gln Ile Lys Glu Lys Gln Lys Ala
100 105 110

Gly Leu Leu Thr Leu Glu Asp His Pro Asn Ile Lys Arg Val Thr Pro
115 120 125

Gln Arg Lys Val Phe Arg Ser Leu Lys Phe Ala Glu Ser Asp Pro Ile
130 135 140

Val Pro Cys Asn Glu Thr Arg Trp Ser Gln Lys Trp Gln Ser Ser Arg
145 150 155 160

Pro Leu Arg Arg Ala Ser Leu Ser Leu Gly Ser Gly Phe Trp His Ala
165 170 175

Thr Gly Arg His Ser Ser Arg Arg Leu Leu Arg Ala Ile Pro Arg Gln
180 185 190

Val Ala Gln Thr Leu Gln Ala Asp Val Leu Trp Gln Met Gly Tyr Thr
195 200 205

Gly Ala Asn Val Arg Val Ala Val Phe Asp Thr Gly Leu Ser Glu Lys
210 215 220

His Pro His Phe Lys Asn Val Lys Glu Arg Thr Asn Trp Thr Asn Glu
225 230 235 240

Arg Thr Leu Asp Asp Gly Leu Gly His Gly Thr Phe Val Ala Gly Val
245 250 255

Ile Ala Ser Met Arg Glu Cys Gln Gly Phe Ala Pro Asp Ala Glu Leu
260 265 270

His Ile Phe Arg Val Phe Thr Asn Asn Gln Val Ser Tyr Thr Ser Trp
275 280 285

Phe Leu Asp Ala Phe Asn Tyr Ala Ile Leu Lys Lys Ile Asp Val Leu
290 295 300

Asn Leu Ser Ile Gly Gly Pro Asp Phe Met Asp His Pro Phe Val Asp
305 310 315 320

Lys Val Trp Glu Leu Thr Ala Asn Asn Val Ile Met Val Ser Ala Ile
325 330 335

Gly Asn Asp Gly Pro Leu Tyr Gly Thr Leu Asn Asn Pro Ala Asp Gln
340 345 350

Met Asp Val Ile Gly Val Gly Gly Ile Asp Phe Glu Asp Asn Ile Ala

-continued

```
        355                 360                 365

Arg Phe Ser Ser Arg Gly Met Thr Thr Trp Glu Leu Pro Gly Gly Tyr
    370                 375                 380

Gly Arg Val Lys Pro Asp Ile Val Thr Tyr Gly Ala Gly Val Arg Gly
385                 390                 395                 400

Ser Gly Val Lys Gly Gly Cys Arg Ala Leu Ser Gly Thr Ser Val Ala
                405                 410                 415

Ser Pro Val Val Ala Gly Ala Val Thr Leu Leu Val Ser Thr Val Gln
            420                 425                 430

Lys Arg Glu Leu Val Asn Pro Ala Ser Val Lys Gln Ala Leu Ile Ala
        435                 440                 445

Ser Ala Arg Arg Leu Pro Gly Val Asn Met Phe Glu Gln Gly His Gly
    450                 455                 460

Lys Leu Asp Leu Leu Arg Ala Tyr Gln Ile Leu Ser Ser Tyr Lys Pro
465                 470                 475                 480

Gln Ala Ser Leu Ser Pro Ser Tyr Ile Asp Leu Thr Glu Cys Pro Tyr
                485                 490                 495

Met Trp Pro Tyr Cys Ser Gln Pro Ile Tyr Tyr Gly Gly Met Pro Thr
            500                 505                 510

Ile Val Asn Val Thr Ile Leu Asn Gly Met Gly Val Thr Gly Arg Ile
        515                 520                 525

Val Asp Lys Pro Glu Trp Arg Pro Tyr Leu Pro Gln Asn Gly Asp Asn
    530                 535                 540

Ile Glu Val Ala Phe Ser Tyr Ser Ser Val Leu Trp Pro Trp Ser Gly
545                 550                 555                 560

Tyr Leu Ala Ile Ser Ile Ser Val Thr Lys Lys Ala Ala Ser Trp Glu
                565                 570                 575

Gly Ile Ala Gln Gly His Ile Met Ile Thr Val Ala Ser Pro Ala Glu
            580                 585                 590

Thr Glu Ala Lys Asn Gly Ala Glu His Thr Ser Thr Val Lys Leu Pro
        595                 600                 605

Ile Lys Val Lys Ile Ile Pro Thr Pro Pro Arg Ser Lys Arg Val Leu
    610                 615                 620

Trp Asp Gln Tyr His Asn Leu Arg Tyr Pro Pro Gly Tyr Phe Pro Arg
625                 630                 635                 640

Asp Asn Leu Arg Met Lys Asn Asp Pro Leu Asp Trp Asn Gly Asp His
                645                 650                 655

Val His Thr Asn Phe Arg Asp Met Tyr Gln His Leu Arg Ser Met Gly
            660                 665                 670

Tyr Phe Val Glu Val Leu Gly Ala Pro Phe Thr Cys Phe Asp Ala Thr
        675                 680                 685

Gln Tyr Gly Thr Leu Leu Met Val Asp Ser Glu Glu Glu Tyr Phe Pro
    690                 695                 700

Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
            740                 745                 750

Ala Asn Ile Pro Ala Leu Asn Glu Leu Leu Ser Val Trp Asn Met Gly
        755                 760                 765

Phe Ser Asp Gly Leu Tyr Glu Gly Glu Phe Ala Leu Ala Asn His Asp
    770                 775                 780
```

```
Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
            820                 825                 830

Ile Pro Ala Glu Gly Gly Gly Arg Ile Val Leu Tyr Gly Asp Ser Asn
        835                 840                 845

Cys Leu Asp Asp Ser His Arg Gln Lys Asp Cys Phe Trp Leu Leu Asp
    850                 855                 860

Ala Leu Leu Gln Tyr Thr Ser Tyr Gly Val Asn Pro Pro Ser Leu Ser
865                 870                 875                 880

His Ser Gly Asn Arg Gln Arg Pro Pro Ser Gly Ala Gly Leu Ala Pro
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

His Leu Ser Trp Ala Lys Pro Gln Pro Leu Asn Glu Thr Ala Pro Ser
    930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
        995                 1000                1005

Gly Ala Met Val Ala Leu Ala Phe Phe Val Val Gln Ile Ser Lys Ala
   1010                1015                1020

Lys Ser Arg Pro Lys Arg Arg Arg Pro Arg Ala Lys Arg Pro Gln Leu
1025               1030                1035                1040

Thr Gln Gln Thr His Pro Pro Arg Thr Pro Ser Val
               1045                1050


<210> SEQ ID NO 2
<211> LENGTH: 4198
<212> TYPE: DNA
<213> ORGANISM: Cricetulus griseus

<400> SEQUENCE: 2

tgttcgcggc agaggcgccg ttcccccggg cccgccgacc tcgagcctga ggcggacgca      60

ggtcggccct cagagtggtt tcttgggcat ccccactaga tttgggtctg tggtgcaaat     120

ggagtctagg actcagtcga ctctgcccta atgagagaag cccctgtcca agatggagaa     180

gaagcggaga aagaaatgaa agcctctttt tgggccaagc tgtgggtgac catgggactg     240

aggttttctt tacgttggac aagtctgtag gatggctgat cagtaaggtt gcagctttta     300

gccaaaacag aaattcactt ctgatcaagg aagaacctag tgcgatttga atttatgcaa     360

ttttatgacc atattcactt aggaccatga agctcatcaa catctggctt cttctgctgg     420

tggttttgct ctgtggaaag aagcatctgg gtgacaggct ggggaagaaa gcgtttgaaa     480

aggcatcatg ccctagctgt tcccacctga ctttgaaggt ggaattctcc tcaactgtgg     540

tggaatatga atatattgtg gctttcaacg gatacttcac agccaaagct agaaactcat     600
```

-continued

```
ttatttcaag tgctctgaaa agcagtgaag tagacaactg gagaattata cctcggaaca    660
acccatccag tgactaccct agtgattttg aggtgattca gataaaagag aagcagaagg    720
ccgggctgct cacacttgaa gatcatccaa acatcaagcg ggtgacacct caacgcaaag    780
tctttcgttc cttgaagttt gctgaatctg accccattgt gccatgtaat gaaactcggt    840
ggagccagaa gtggcagtca tcacgacccc tgagaagagc cagtctctcc ctgggctctg    900
gattctggca tgcaacagga agacattcaa gccggcgatt gctgagagcc attcctcgac    960
aggttgccca gacattgcag gcagatgtgc tgtggcagat gggatacaca ggtgctaatg   1020
tcagggttgc tgtttttgat actgggctca gtgagaagca tccacacttc aagaatgtga   1080
aggagagaac caactggacc aatgagcgga ccctggatga tgggctgggc catggcacat   1140
ttgtcgcagg tgtgattgcc agcatgaggg agtgccaggg atttgcccca gatgcagagc   1200
tgcacatctt ccgggtcttt accaacaatc aggtgtctta cacatcttgg tttttggacg   1260
ctttcaacta tgccatccta aagaagattg atgttctaaa ccttagcatc ggcgggcctg   1320
acttcatgga tcatcccttt gttgacaagg tgtgggaatt aacagctaac aatgtaatca   1380
tggtttctgc tatcggcaat gatggacctc tttatggcac tctgaataac ccagctgatc   1440
agatggatgt gattggagtg ggtggcattg actttgaaga taacatcgcc cgcttttctt   1500
ccaggggaat gactacctgg gaactaccag gaggctatgg tcgcgtgaaa cctgacattg   1560
tcacctatgg tgccggagtg cggggttccg gtgtgaaagg gggctgccgg gcactctcag   1620
ggaccagtgt cgcttcccca gtggttgctg ggctgtcac cttgttagta agcacagtgc    1680
agaagcggga gctagtgaat cctgccagtg tgaagcaagc cctgattgca tcagcccgga   1740
ggcttcctgg tgttaacatg ttcgagcaag gccatggcaa gctggatctg ctgcgagcct   1800
atcagatcct cagcagctac aaaccacagg cgagcttgag tcctagctac atcgacctga   1860
ctgagtgtcc ctacatgtgg ccttactgtt ctcagcccat ctactatgga ggaatgccaa   1920
caattgttaa tgtcaccatc ctcaatggca tgggagtcac aggaagaatt gtggataagc   1980
ctgagtggcg gccctattta ccacagaatg gagacaacat tgaagtggcc ttctcctact   2040
cctcagtgtt atggccttgg tcaggctacc tggccatctc catttctgtg accaagaagg   2100
cagcttcctg ggaaggcatt gcacagggtc acatcatgat cacggtggct tccccagcag   2160
agacggaagc aaaaaatggt gccgagcata cttccacagt gaagcttccc attaaggtga   2220
agatcattcc caccctcct cggagcaaga gagtcctctg ggaccagtat cacaacctcc    2280
gctacccccc aggctacttt cccagggaca acttgcggat gaagaatgat cctttagact   2340
ggaatggcga ccatgtccac accaatttca gggacatgta ccagcacctg cgcagcatgg   2400
gctacttcgt ggaggtgctc ggtgccccat tcacgtgctt tgatgctaca cagtatggca   2460
ctttgctcat ggtggatagt gaagaagagt acttcccaga ggagattgcc aagctgagga   2520
gggacgtgga caatggcctt tccctcgtca tcttcagtga ctggtacaac acttctgtta   2580
tgagaaaagt gaagttttac gatgaaaaca caaggcagtg gtggatgcca gatactggag   2640
gagccaacat cccagctctg aacgagctgc tgtctgtgtg gaacatgggg ttcagcgatg   2700
gcctttatga aggggagttt gccctggcga atcatgacat gtattatgca tcgggatgca   2760
gcatcgccaa gtttccagaa gatggtgttg tgatcacaca gactttcaag gaccaaggat   2820
tggaggtctt aaaacaagag acagcagttg ttgaaaatgt tcccattttg gggctttatc   2880
agattccagc tgaaggtggg ggccggatcg tgttgtatgg agattccaat tgcttggatg   2940
```

-continued

```
acagtcacag acagaaggat tgcttttggc ttctggatgc actccttcag tacacatcat   3000

atggcgtgaa ccctcccagc ctcagccatt cagggaaccg gcagcgccca cccagtggag   3060

ctggcttggc cctcctgaa aggatggaag gaaaccacct tcatcgatac tccaaggttc   3120

ttgaggccca tctgggagac ccaaaacctc ggcctcttcc agcctgtcca cacttgtcat   3180

gggccaagcc acagcctttg aatgagactg cgcccagtaa tctttggaaa catcagaagc   3240

tgctctccat tgacctggac aaagtagtgt tacccaactt tcgatcgaat cgccctcaag   3300

tgagaccttt gtcccctgga gaaagtggtg cctgggacat tcctggaggg atcatgcctg   3360

gccgctacaa ccaagaggtg ggccagacca tccctgtctt tgccttcctc ggagccatgg   3420

tggccctggc cttctttgtg gtacagatca gcaaggccaa aagccggccg aagcggagga   3480

ggcccagggc aaagcgtcca cagcttacac agcagaccca cccaccaagg accccgtcag   3540

tgtgatcatc acagtggcca gccacagaag ccaacaagcc ttggaccact ctgatggcca   3600

cacagggcat cagaagagca tcctgggagg tgcctatttc caagggaccc catctccagc   3660

ttgtggctgg gttagtgtgt tctccccagg catctctgag ttacatcctg aagtacctca   3720

ctgtgctggg ctcttgacag gaggtgctca gtagctcagc ctccagtggt gtcagcaggc   3780

ccagtgacag tgcaccaaag acacagagcc tggaagggct gtcgggacac actttctaca   3840

taaagcttac aatcctgacc aagcgaagaa atgcttgtta caggctattt tctatattta   3900

ttgtggggag agtcacttta aagacttgta ctgtttggaa gcaaagctgt tgtgtttgtc   3960

agttgagtgc agttttctgc agtgacatca taaggagtca gatcccatga ccttttttgat   4020

gagaggacag actgaactga agggcatgtg cacagatctg ggaaatgcaa gccttcgctt   4080

tatttttata agtatcaact gccatcatgt tttgtaattt ggggtcttga tttcaccatt   4140

gttggtgaaa gaaattttca ataaatatgc ataaccttaa aaaaaaaaaa aaaaaaa      4198
```

<210> SEQ ID NO 3
<211> LENGTH: 1052
<212> TYPE: PRT
<213> ORGANISM: Human

<400> SEQUENCE: 3

```
Met Lys Leu Val Asn Ile Trp Leu Leu Leu Leu Val Val Leu Leu Cys
  1               5                  10                  15

Gly Lys Lys His Leu Gly Asp Arg Leu Glu Lys Lys Ser Phe Glu Lys
             20                  25                  30

Ala Pro Cys Pro Gly Cys Ser His Leu Thr Leu Lys Val Glu Phe Ser
         35                  40                  45

Ser Thr Val Val Glu Tyr Glu Tyr Ile Val Ala Phe Asn Gly Tyr Phe
     50                  55                  60

Thr Ala Lys Ala Arg Asn Ser Phe Ile Ser Ser Ala Leu Lys Ser Ser
 65                  70                  75                  80

Glu Val Asp Asn Trp Arg Ile Ile Pro Arg Asn Asn Pro Ser Ser Asp
                 85                  90                  95

Tyr Pro Ser Asp Phe Glu Val Ile Gln Ile Lys Glu Lys Gln Lys Ala
            100                 105                 110

Gly Leu Leu Thr Leu Glu Asp His Pro Asn Ile Lys Arg Val Thr Pro
        115                 120                 125

Gln Arg Lys Val Phe Arg Ser Leu Lys Tyr Ala Glu Ser Asp Pro Thr
    130                 135                 140

Val Pro Cys Asn Glu Thr Arg Trp Ser Gln Lys Trp Gln Ser Ser Arg
145                 150                 155                 160
```

-continued

```
Pro Leu Arg Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
            180                 185                 190

Val Ala Gln Thr Leu Gln Ala Asp Val Leu Trp Gln Met Gly Tyr Thr
        195                 200                 205

Gly Ala Asn Val Arg Val Ala Val Phe Asp Thr Gly Leu Ser Glu Lys
    210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
                245                 250                 255

Ile Ala Ser Met Arg Glu Cys Gln Gly Phe Ala Pro Asp Ala Glu Leu
            260                 265                 270

His Ile Phe Arg Val Phe Thr Asn Asn Gln Val Ser Tyr Thr Ser Trp
        275                 280                 285

Phe Leu Asp Ala Phe Asn Tyr Ala Ile Leu Lys Lys Ile Asp Val Leu
    290                 295                 300

Asn Leu Ser Ile Gly Gly Pro Asp Phe Met Asp His Pro Phe Val Asp
305                 310                 315                 320

Lys Val Trp Glu Leu Thr Ala Asn Asn Val Ile Met Val Ser Ala Ile
                325                 330                 335

Gly Asn Asp Gly Pro Leu Tyr Gly Thr Leu Asn Asn Pro Ala Asp Gln
            340                 345                 350

Met Asp Val Ile Gly Val Gly Gly Ile Asp Phe Glu Asp Asn Ile Ala
        355                 360                 365

Arg Phe Ser Ser Arg Gly Met Thr Thr Trp Glu Leu Pro Gly Gly Tyr
    370                 375                 380

Gly Arg Met Lys Pro Asp Ile Val Thr Tyr Gly Ala Gly Val Arg Gly
385                 390                 395                 400

Ser Gly Val Lys Gly Gly Cys Arg Ala Leu Ser Gly Thr Ser Val Ala
                405                 410                 415

Ser Pro Val Val Ala Gly Ala Val Thr Leu Leu Val Ser Thr Val Gln
            420                 425                 430

Lys Arg Glu Leu Val Asn Pro Ala Ser Met Lys Gln Ala Leu Ile Ala
        435                 440                 445

Ser Ala Arg Arg Leu Pro Gly Val Asn Met Phe Glu Gln Gly His Gly
    450                 455                 460

Lys Leu Asp Leu Leu Arg Ala Tyr Gln Ile Leu Asn Ser Tyr Lys Pro
465                 470                 475                 480

Gln Ala Ser Leu Ser Pro Ser Tyr Ile Asp Leu Thr Glu Cys Pro Tyr
                485                 490                 495

Met Trp Pro Tyr Cys Ser Gln Pro Ile Tyr Tyr Gly Gly Met Pro Thr
            500                 505                 510

Val Val Asn Val Thr Ile Leu Asn Gly Met Gly Val Thr Gly Arg Ile
        515                 520                 525

Val Asp Lys Pro Asp Trp Gln Pro Tyr Leu Pro Gln Asn Gly Asp Asn
    530                 535                 540

Ile Glu Val Ala Phe Ser Tyr Ser Ser Val Leu Trp Pro Trp Ser Gly
545                 550                 555                 560

Tyr Leu Ala Ile Ser Ile Ser Val Thr Lys Lys Ala Ala Ser Trp Glu
                565                 570                 575
```

-continued

```
Gly Ile Ala Gln Gly His Val Met Ile Thr Val Ala Ser Pro Ala Glu
            580                 585                 590

Thr Glu Ser Lys Asn Gly Ala Glu Gln Thr Ser Thr Val Lys Leu Pro
        595                 600                 605

Ile Lys Val Lys Ile Ile Pro Thr Pro Pro Arg Ser Lys Arg Val Leu
    610                 615                 620

Trp Asp Gln Tyr His Asn Leu Arg Tyr Pro Pro Gly Tyr Phe Pro Arg
625                 630                 635                 640

Asp Asn Leu Arg Met Lys Asn Asp Pro Leu Asp Trp Asn Gly Asp His
                645                 650                 655

Ile His Thr Asn Phe Arg Asp Met Tyr Gln His Leu Arg Ser Met Gly
            660                 665                 670

Tyr Phe Val Glu Val Leu Gly Ala Pro Phe Thr Cys Phe Asp Ala Ser
        675                 680                 685

Gln Tyr Gly Thr Leu Leu Met Val Asp Ser Glu Glu Glu Tyr Phe Pro
    690                 695                 700

Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
            740                 745                 750

Ala Asn Ile Pro Ala Leu Asn Glu Leu Leu Ser Val Trp Asn Met Gly
        755                 760                 765

Phe Ser Asp Gly Leu Tyr Glu Gly Glu Phe Thr Leu Ala Asn His Asp
    770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
            820                 825                 830

Ile Pro Ala Glu Gly Gly Gly Arg Ile Val Leu Tyr Gly Asp Ser Asn
        835                 840                 845

Cys Leu Asp Asp Ser His Arg Gln Lys Asp Cys Phe Trp Leu Leu Asp
    850                 855                 860

Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Ser Val Thr
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

Arg Leu Ser Trp Ala Lys Pro Gln Pro Leu Asn Glu Thr Ala Pro Ser
    930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
```

```
       995                 1000                1005

Gly Ala Met Val Val Leu Ala Phe Phe Val Val Gln Ile Asn Lys Ala
   1010                1015                1020

Lys Ser Arg Pro Lys Arg Arg Lys Pro Arg Val Lys Arg Pro Gln Leu
1025                1030                1035                1040

Met Gln Gln Val His Pro Pro Lys Thr Pro Ser Val
               1045                1050


<210> SEQ ID NO 4
<211> LENGTH: 4338
<212> TYPE: DNA
<213> ORGANISM: Human

<400> SEQUENCE: 4

cagggcacgc tgggtcggcg gagctgaggc tcccagctgt gggcctcgct ggcccggtcg     60

cccagtctcg cgagagttgg gagtaaacag ccccgaatgg agtgcccagg cgtgttcgcc    120

gcggaggcgc cgttatcccg ggcccgccgg ccctgagctc ccggcggcgc agattggctc    180

acagtggttg attgatcaac cccattggac gttggttctg tggtacaaat ggagtacagg    240

actcagtcgt cacggcctga gtgagagaag ccttatttcc aagatggaga agaagcggag    300

aaagaaatga aagcctctct tcaggctgaa ccacaaaagg ccatgggatt taacttttat    360

ttatgttggg caagactgta agatggctga tcagtaatgt tgcagctttt agctgaaaca    420

aaaattcact tttaatcaag aagaaaaaag tgtgatttga atatatgcaa ttttatgatc    480

atattcgctt gtgaccatga agcttgtcaa catctggctg cttctgctcg tggttttgct    540

ctgtgggaag aaacatctgg gcgacagact ggaaaagaaa tcttttgaaa aggccccatg    600

ccctggctgt tcccacctga ctttgaaggt ggaattctca tcaacagttg tggaatatga    660

atatattgtg gctttcaatg gatactttac agccaaagct agaaattcat ttatttcaag    720

tgccctgaag agcagtgaag tagacaattg gagaattata cctcgaaaca atccatccag    780

tgactaccct agtgattttg aggtgattca gataaaagaa aaacagaaag cggggctgct    840

aacacttgaa gatcatccaa acatcaaacg ggtcacgccc caacgaaaag tctttcgttc    900

cctcaagtat gctgaatctg accccacagt accctgcaat gaaacccggt ggagccagaa    960

gtggcaatca tcacgtcccc tgcgaagagc cagcctctcc ctgggctctg gcttctggca   1020

tgctacggga aggcattcga gcagacggct gctgagagcc atcccgcgcc aggttgccca   1080

gacactgcag gcagatgtgc tctggcagat gggatataca ggtgctaatg taagagttgc   1140

tgtttttgac actgggctga gcgagaagca tccccacttc aaaaatgtga aggagagaac   1200

caactggacc aacgagcgaa cgctggacga tgggttgggc catggcacat tcgtggcagg   1260

tgtgatagcc agcatgaggg agtgccaagg atttgctcca gatgcagaac ttcacatttt   1320

cagggtcttt accaataatc aggtatctta cacatcttgg tttttggacg ccttcaacta   1380

tgccatttta aagaagatcg acgtgttaaa cctcagcatc ggcggcccgg acttcatgga   1440

tcatccgttt gttgacaagg tgtgggaatt aacagctaac aatgtaatca tggtttctgc   1500

tattggcaat gacggacctc tttatggcac tctgaataac cctgctgatc aaatggatgt   1560

gattggagta ggcggcattg actttgaaga taacatcgcc cgcttttctt caaggggaat   1620

gactacctgg gagctaccag gaggctacgg tcgcatgaaa cctgacattg tcacctatgg   1680

tgctggcgtg cggggttctg gcgtgaaagg ggggtgccgg gccctctcag ggaccagtgt   1740

tgcttctcca gtggttgcag gtgctgtcac cttgttagtg agcacagtcc agaagcgtga   1800
```

-continued

```
gctggtgaat cccgccagta tgaagcaggc cctgatcgcg tcagcccgga ggctccccgg   1860
ggtcaacatg tttgagcaag gccacggcaa gctcgatctg ctcagagcct atcagatcct   1920
caacagctac aagccacagg caagtttgag ccccagctac atagatctga ctgagtgtcc   1980
ctacatgtgg ccctactgct cccagcccat ctactatgga ggaatgccga cagttgttaa   2040
tgtcaccatc ctcaacggca tgggagtcac aggaagaatt gtagataagc ctgactggca   2100
gccctatttg ccacagaacg gagacaacat tgaagttgcc ttctcctact cctcggtctt   2160
atggccttgg tcgggctacc tggccatctc catttctgtg accaagaaag cggcttcctg   2220
ggaaggcatt gctcagggcc atgtcatgat cactgtggct tccccagcag agacagagtc   2280
aaaaaatggt gcagaacaga cttcaacagt aaagctcccc attaaggtga agataattcc   2340
tactcccccg cgaagcaaga gagttctctg ggatcagtac cacaacctcc gctatccacc   2400
tggctatttc cccagggata atttaaggat gaagaatgac cctttagact ggaatggtga   2460
tcacatccac accaatttca gggatatgta ccagcatctg agaagcatgg gctactttgt   2520
agaggtcctc ggggcccct tcacgtgttt tgatgccagt cagtatggca ctttgctgat   2580
ggtggacagt gaggaggagt acttccctga agagatcgcc aagctccgga gggacgtgga   2640
caacggcctc tcgctcgtca tcttcagtga ctggtacaac acttctgtta tgagaaaagt   2700
gaagttttat gatgaaaaca caaggcagtg gtggatgccg gataccggag gagctaacat   2760
cccagctctg aatgagctgc tgtctgtgtg gaacatgggg ttcagcgatg gcctgtatga   2820
aggggagttc accctggcca accatgacat gtattatgcg tcagggtgca gcatcgcgaa   2880
gtttccagaa gatggcgtcg tgataacaca gactttcaag gaccaaggat tggaggtttt   2940
aaagcaggaa acagcagttg ttgaaaacgt ccccattttg ggactttatc agattccagc   3000
tgagggtgga ggccggattg tactgtatgg ggactccaat tgcttggatg acagtcaccg   3060
acagaaggac tgcttttggc ttctggatgc cctcctccag tacacatcgt atggggtgac   3120
accgcctagc ctcagtcact ctgggaaccg ccagcgccct cccagtggag caggctcagt   3180
cactccagag aggatggaag gaaaccatct tcatcggtac tccaaggttc tggaggccca   3240
tttgggagac ccaaaacctc ggcctctacc agcctgtcca cgcttgtctt gggccaagcc   3300
acagccttta aacgagacgg cgcccagtaa cctttggaaa catcagaagc tactctccat   3360
tgacctggac aaggtggtgt tacccaactt tcgatcgaat cgccctcaag tgaggccctt   3420
gtcccctgga gagagcggcg cctgggacat tcctggaggg atcatgcctg gccgctacaa   3480
ccaggaggtg ggccagacca ttcctgtctt tgccttcctg ggagccatgg tggtcctggc   3540
cttctttgtg gtacaaatca acaaggccaa gagcaggccg aagcggagga agcccagggt   3600
gaagcgcccg cagctcatgc agcaggttca cccgccaaag acccccttcgg tgtgaccggc   3660
agcctggctg accgtgaggg ccagagagag ccttcacgga cggcgctggt gggtgagccg   3720
agctgtggtg gcggctggtt taaaagggat ccagtttcca gctgcaggtt tgttagagtc   3780
tgttctacat gggcctgccc tcctgtgatg ggcagaggct cctggtacat cgagaagatt   3840
cctgtggatc ccgtcaggag ggacttagtg gctctgccgc cagtgagact tcccgccggc   3900
agctgtgcgc accaaagact cgggagaact ggaaaggctg tctggggtct tctgactgca   3960
ggggaaggat gtactttcca aacaaatgat acaaccctga ccaagctaaa agacgcttgt   4020
taaaggctat tttctatatt tattgttggg aaaagtcact ttaaagactt gtgctatttg   4080
gaagcaaagc tatttttttt gtcagtggaa tgcagttttt ttactattcc atcatgagga   4140
acaacataga ttccatgatc tttttaatga cagtacagac tgagatttga aggaaacatg   4200
```

```
cacaaatctg taaaacatag accttcgctt tatttttgta agtatcacct gccaccatgt   4260

tttgtaattt gaggtcttga tttcaccatt gtcggtgaag aaaattttca ataaatatgt   4320

attacccgtc tgaagctt                                                 4338


<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 5

Ser Glu Gln Lys Leu Ile Ser Glu Glu Asp Leu Asn Gly Glu Gln Lys
  1               5                  10                  15

Leu Ile Ser Glu Glu Asp Leu Asn Gly Glu Gln Lys Leu Ile Ser Glu
             20                  25                  30

Glu Asp Leu Asn Ser Ser Gly
         35


<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 6

gtggtgcaaa tggagtctag g                                               21


<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 7

cacagaaatg gagatggcca g                                               21


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 8

accaagaagg cagcttcctg g                                               21


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 9

ttcccagatc tgtgcacatg c                                               21
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 10

Arg Ser Val Leu Ser
  1               5


<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 11

Arg Ser Val Leu
  1


<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 12

Gly Gly Arg
  1


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 13

Val Phe Arg Ser Leu Lys
  1               5


<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 14

Arg Lys Val Phe Arg Ser Leu Lys
  1               5


<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE
```

<400> SEQUENCE: 15

Phe Ala Glu Ser Asp Pro Ile Val
1 5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 16

Ser Phe Glu Ser Gly Ser Gly
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 17

His Ser Gly Ser Gly Arg Ser Val Leu
1 5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 18

Arg Ser Leu Lys
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 19

Arg Arg Leu Leu
1

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 20

Arg Gly Leu Thr Ser
1 5

<210> SEQ ID NO 21
<211> LENGTH: 4
<212> TYPE: PRT

-continued

```
<213> ORGANISM: Artificial Sequence
<220> FEATURE:
<223> OTHER INFORMATION: Description of Artificial Sequence:  SYNTHETIC
      PEPTIDE

<400> SEQUENCE: 21

Ala Ala Ala Ala
  1


<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 22

Arg Arg Leu Leu Arg
  1               5


<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 23

Ala Ala Ala Ala Ala
  1               5


<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 24

cctcaacgca aagtctttgc cgcggctgct tttgctgaat ctgaccc                    47


<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 25

ggcagtcatc acgacccctg gttgccgcta gcctctccct gggc                       44


<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 26

aggaagacat tcaagcgccg cggctgctgc tgccattcct cgacagg                    47


<210> SEQ ID NO 27
```

-continued

```
<211> LENGTH: 48
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 27

agaacctgac tcgaatgact tcagagatct gccagagcct gagtgtgg                48


<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 28

agaacctgac tcgaatgaca gcagccggcg gccagagcct gagtgtgg                48


<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 29

Cys Lys Ala Lys Ser Arg Pro Lys Arg Arg Arg Pro Arg Ala Lys Arg
  1               5                  10                  15


<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 30

Cys Pro Gln Leu Thr Gln Gln Thr His Pro Pro Arg Thr Pro Ser Val
  1               5                  10                  15


<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 31

Asp Arg Leu Gly Lys Lys Ala
  1               5


<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 32

Phe Ala Glu Ser Asp Pro Ile
  1               5
```

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 33

Arg Ala Ile Pro Arg Gln Val
1 5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 34

Asp Gly Lys Asp Asp Asp Met Ile Asp
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 35

Asp Gly His Asp Asp Asp Met Ile Asp
1 5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 36

Glu Glu Glu Asp Lys Lys Glu Asp Val
1 5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 37

Val Ala Ala Ser Leu
1 5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 38

Ala Ser Val Leu
1

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 39

Ser Gly Arg Ser Val Leu
1 5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 40

Arg Val Arg Arg
1

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 41

Val Phe Ala Ser Leu Lys
1 5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 42

Val Phe Arg Ser Arg Arg
1 5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 43

Ser Gly Ser Gly Arg Ser Val Leu
1 5

<210> SEQ ID NO 44
<211> LENGTH: 36

-continued

```
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 44

Glu Gln Lys Leu Ile Ser Glu Glu Asp Leu Gly Gly Glu Gln Lys Leu
  1               5                  10                  15

Ile Ser Glu Glu Asp Leu Gly Pro Arg Phe Glu Gln Lys Leu Ile Ser
             20                  25                  30

Glu Glu Asp Leu
         35


<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 45

Asp Met His Thr Gly
  1               5


<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 46

cgggatccat gaagctcatc aacatctggc                                       30


<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 47

ggagaattcc accttcaaag tcagg                                            25


<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:  SYNTHETIC
      PRIMER

<400> SEQUENCE: 48

ttcagtacac atcatatggc gtgaaccctc                                       30


<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence:  SYNTHETIC
      PRIMER
```

<400> SEQUENCE: 49
tagactcgag cggccgccca ctgacggggt ccttggtggg tgggtctg 48

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: SYNTHETIC PRIMER

<400> SEQUENCE: 50
ggccgcgaac aaaaactcat ctcagaagag gatctgggtg gtgagcagaa gttgatttct 60
gaggaagacc tgggcc 76

<210> SEQ ID NO 51
<211> LENGTH: 68
<212> TYPE: DNA
<213> ORGANISM: Artificial Sequence
<220> FEATURE:
<223> OTHER INFORMATION: Description of Artificial Sequence: SYNTHETIC PRIMER

<400> SEQUENCE: 51
caggtcttcc tcagaaatca acttctgctc accacccaga tcctcttctg agatgagttt 60
ttgttcgc 68

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: SYNTHETIC PRIMER

<400> SEQUENCE: 52
tagactcgag cggccgccct cttggttgta gcggccaggc atgatcc 47

<210> SEQ ID NO 53
<211> LENGTH: 50
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 53

```
Gly Gly Arg Glu Gln Lys Leu Ile Ser Glu Glu Asp Leu Gly Gly Glu
  1               5                  10                  15

Gln Lys Leu Ile Ser Glu Glu Asp Leu Gly Pro Arg Phe Glu Gln Lys
             20                  25                  30

Leu Ile Ser Glu Glu Asp Leu Asp Met His Thr Gly His His His His
         35                  40                  45

His His
     50
```

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 54

```
Arg Val Arg Arg
  1
```

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 55

```
His Ser Gly Ser Gly Arg Ser Val Leu Ser Phe Glu Ser Gly Ser Gly
  1               5                  10                  15
```

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 56

```
Arg Lys Val Phe Arg Ser Leu Lys Phe Ala Glu Ser Asp Pro Ile Val
  1               5                  10                  15
```

<210> SEQ ID NO 57
<211> LENGTH: 27
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 57

```
Gly Gly Ala His Asp Ser Asp Gln His Pro His Ser Gly Ser Gly Arg
  1               5                  10                  15

Ser Val Leu Ser Phe Glu Ser Gly Ser Gly Gly
             20                  25
```

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 58

```
Arg Ala Ile Pro Arg Gln Val Ala Gln Thr Leu Gln
  1               5                  10
```

<210> SEQ ID NO 59
<211> LENGTH: 506
<212> TYPE: PRT
<213> ORGANISM: Human

<400> SEQUENCE: 59

```
Met Leu Leu Leu Leu Leu Leu Leu Gly Leu Arg Leu Gln Leu Ser Leu
  1               5                  10                  15

Gly Ile Ile Leu Val Glu Glu Glu Asn Pro Asp Phe Trp Asn Arg Glu
             20                  25                  30

Ala Ala Glu Ala Leu Gly Ala Ala Lys Lys Leu Gln Pro Ala Gln Thr
```

-continued

```
        35                  40                  45

Ala Ala Lys Asn Leu Ile Ile Phe Leu Gly Asp Gly Val Gly Val Ser
     50                  55                  60

Thr Val Thr Ala Ala Arg Ile Leu Lys Gly Gln Lys Lys Asp Lys Leu
 65                  70                  75                  80

Gly Pro Glu Ile Pro Leu Ala Met Asp Arg Phe Pro Tyr Val Ala Leu
                 85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
    210                 215                 220

Phe Arg Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                245                 250                 255

Lys His Gln Gly Ala Arg Tyr Val Trp Asn Arg Thr Glu Leu Met Arg
            260                 265                 270

Ala Ser Leu Asp Pro Ser Val Ala His Leu Met Gly Leu Phe Glu Pro
        275                 280                 285

Gly Asp Met Lys Tyr Glu Ile His Arg Asp Ser Thr Leu Asp Pro Ser
    290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
        355                 360                 365

Ser Leu Val Thr Ala Asp His Ser His Val Phe Ser Phe Gly Gly Cys
    370                 375                 380

Pro Leu Arg Gly Gly Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
            420                 425                 430

Ser Pro Glu Tyr Arg Gln Gln Ser Ala Val Pro Leu Asp Glu Glu Thr
        435                 440                 445

His Ala Gly Glu Asp Val Ala Val Phe Ala Arg Gly Pro Gln Ala His
    450                 455                 460
```

```
Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly
            500                 505


<210> SEQ ID NO 60
<211> LENGTH: 629
<212> TYPE: PRT
<213> ORGANISM: Human

<400> SEQUENCE: 60

Pro His Ser Gly Ser Gly Arg Ser Val Leu Ser Phe Glu Ser Gly Ser
  1               5                  10                  15

Gly Gly Trp Phe Asp Trp Met Met Pro Thr Leu Leu Leu Trp Leu Val
            20                  25                  30

Asn Gly Val Ile Val Leu Ser Val Phe Val Lys Leu Leu Val His Gly
        35                  40                  45

Glu Pro Val Ile Arg Pro His Ser Arg Ser Ser Val Thr Phe Trp Arg
    50                  55                  60

His Arg Lys Gln Ala Asp Leu Asp Leu Ala Arg Gly Asp Phe Ala Ala
 65                  70                  75                  80

Ala Ala Ala Asn Leu Gln Thr Cys Leu Ala Val Leu Gly Arg Ala Leu
                85                  90                  95

Pro Thr Ser Arg Leu Asp Leu Ala Cys Ser Leu Ser Trp Asn Val Ile
            100                 105                 110

Arg Tyr Ser Leu Gln Lys Leu Arg Leu Val Arg Trp Leu Leu Lys Lys
        115                 120                 125

Val Phe Gln Cys Arg Arg Ala Thr Pro Ala Thr Glu Ala Gly Phe Glu
    130                 135                 140

Asp Glu Ala Lys Thr Ser Ala Arg Asp Ala Ala Leu Ala Tyr His Arg
145                 150                 155                 160

Leu His Gln Leu His Ile Thr Gly Lys Leu Pro Ala Gly Ser Ala Cys
                165                 170                 175

Ser Asp Val His Met Ala Leu Cys Ala Val Asn Leu Ala Glu Cys Ala
            180                 185                 190

Glu Glu Lys Ile Pro Pro Ser Thr Leu Val Glu Ile His Leu Thr Ala
        195                 200                 205

Ala Met Gly Leu Lys Thr Arg Cys Gly Gly Lys Leu Gly Phe Leu Ala
    210                 215                 220

Ser Tyr Phe Leu Ser Arg Ala Gln Ser Leu Cys Gly Pro Glu His Ser
225                 230                 235                 240

Ala Val Pro Asp Ser Leu Arg Trp Leu Cys His Pro Leu Gly Gln Lys
                245                 250                 255

Phe Phe Met Glu Arg Ser Trp Ser Val Lys Ser Ala Ala Lys Glu Ser
            260                 265                 270

Leu Tyr Cys Ala Gln Arg Asn Pro Ala Asp Pro Ile Ala Gln Val His
        275                 280                 285

Gln Ala Phe Cys Lys Asn Leu Leu Glu Arg Ala Ile Glu Ser Leu Val
    290                 295                 300

Lys Pro Gln Ala Lys Lys Lys Ala Gly Asp Gln Glu Glu Glu Ser Cys
305                 310                 315                 320

Glu Phe Ser Ser Ala Leu Glu Tyr Leu Lys Leu Leu His Ser Phe Val
```

-continued

```
                325                 330                 335

Asp Ser Val Gly Val Met Ser Pro Pro Leu Ser Arg Ser Ser Val Leu
            340                 345                 350

Lys Ser Ala Leu Gly Pro Asp Ile Ile Cys Arg Trp Trp Thr Ser Ala
        355                 360                 365

Ile Thr Val Ala Ile Ser Trp Leu Gln Gly Asp Asp Ala Ala Val Arg
    370                 375                 380

Ser His Phe Thr Lys Val Glu Arg Ile Pro Lys Ala Leu Glu Val Thr
385                 390                 395                 400

Glu Ser Pro Leu Val Lys Ala Ile Phe His Ala Cys Arg Ala Met His
            405                 410                 415

Ala Ser Leu Pro Gly Lys Ala Asp Gly Gln Gln Ser Ser Phe Cys His
            420                 425                 430

Cys Glu Arg Ala Ser Gly His Leu Trp Ser Ser Leu Asn Val Ser Gly
        435                 440                 445

Gly Thr Ser Asp Pro Ala Leu Asn His Val Val Gln Leu Leu Thr Cys
    450                 455                 460

Asp Leu Leu Leu Ser Leu Arg Thr Ala Leu Trp Gln Lys Gln Ala Ser
465                 470                 475                 480

Ala Ser Gln Ala Val Gly Glu Thr Tyr His Ala Ser Gly Ala Glu Leu
            485                 490                 495

Ala Gly Phe Gln Arg Asp Leu Gly Ser Leu Arg Arg Leu Ala His Ser
            500                 505                 510

Phe Arg Pro Ala Tyr Arg Lys Val Phe Leu His Glu Ala Thr Val Arg
        515                 520                 525

Leu Met Ala Gly Gly Ser Pro Thr Arg Thr His Gln Leu Leu Glu His
    530                 535                 540

Ser Leu Arg Arg Arg Thr Thr Gln Ser Thr Lys His Gly Glu Val Asp
545                 550                 555                 560

Ala Trp Pro Gly Gln Arg Glu Arg Ala Thr Ala Ile Leu Leu Ala Cys
            565                 570                 575

Arg His Leu Pro Leu Ser Phe Leu Ser Ser Pro Gly Gln Arg Ala Val
            580                 585                 590

Leu Leu Ala Glu Ala Ala Arg Thr Leu Glu Lys Val Gly Asp Arg Arg
        595                 600                 605

Ser Cys Asn Asp Cys Gln Gln Met Ile Val Lys Leu Gly Gly Gly Thr
    610                 615                 620

Ala Ile Ala Ala Ser
625
```